(12) United States Patent
Trouet

(10) Patent No.: US 10,076,576 B2
(45) Date of Patent: Sep. 18, 2018

(54) MINIMALLY TOXIC PRODRUGS

(71) Applicant: LIFE SCIENCES RESEARCH PARTNERS VZW, Leuven (BE)

(72) Inventor: André Trouet, Leuven (BE)

(73) Assignee: LIFE SCIENCES RESEARCH PARTNERS VZW, Leuven (BE)

( * ) Notice: Subject to any disclaimer, the term of this patent is extended or adjusted under 35 U.S.C. 154(b) by 0 days.

(21) Appl. No.: 14/758,002

(22) PCT Filed: Dec. 27, 2013

(86) PCT No.: PCT/EP2013/078034
§ 371 (c)(1),
(2) Date: Jun. 26, 2015

(87) PCT Pub. No.: WO2014/102312
PCT Pub. Date: Jul. 3, 2014

(65) Prior Publication Data
US 2016/0058880 A1 Mar. 3, 2016

Related U.S. Application Data

(60) Provisional application No. 61/746,621, filed on Dec. 28, 2012.

(51) Int. Cl.
| | |
|---|---|
| *A61K 47/48* | (2006.01) |
| *A61K 45/06* | (2006.01) |
| *B82Y 5/00* | (2011.01) |
| *G01N 33/50* | (2006.01) |
| *A61K 31/337* | (2006.01) |
| *A61K 31/395* | (2006.01) |
| *A61K 31/4745* | (2006.01) |
| *A61K 31/475* | (2006.01) |
| *A61K 31/519* | (2006.01) |
| *A61K 31/537* | (2006.01) |
| *A61K 31/704* | (2006.01) |
| *A61K 39/395* | (2006.01) |

(52) U.S. Cl.
CPC ...... *A61K 47/48338* (2013.01); *A61K 31/337* (2013.01); *A61K 31/395* (2013.01); *A61K 31/475* (2013.01); *A61K 31/4745* (2013.01); *A61K 31/519* (2013.01); *A61K 31/537* (2013.01); *A61K 31/704* (2013.01); *A61K 39/395* (2013.01); *A61K 45/06* (2013.01); *A61K 47/48215* (2013.01); *A61K 47/48361* (2013.01); *B82Y 5/00* (2013.01); *G01N 33/5011* (2013.01)

(58) Field of Classification Search
None
See application file for complete search history.

(56) References Cited

U.S. PATENT DOCUMENTS

| | | |
|---|---|---|
| 7,425,541 B2 | 9/2008 | Dubois et al. |
| 8,034,787 B2 | 10/2011 | Dubois et al. |
| 2002/0142955 A1 | 10/2002 | Dubois et al. |
| 2003/0138432 A1 | 7/2003 | Glazier |
| 2006/0276435 A1 | 12/2006 | Cohen et al. |
| 2006/0281897 A1 | 12/2006 | Trouet et al. |
| 2009/0110753 A1 | 4/2009 | Dubois et al. |

FOREIGN PATENT DOCUMENTS

| | | |
|---|---|---|
| JP | 2003-518000 | 6/2003 |
| JP | 2008-545661 | 12/2008 |
| WO | WO 95/29691 | 11/1995 |
| WO | WO 97/34927 | 9/1997 |
| WO | WO 00/33888 | 6/2000 |
| WO | WO 00/71571 | 11/2000 |
| WO | WO 02/38590 | 5/2002 |
| WO | WO 03/064454 | 8/2003 |
| WO | WO 2008/116053 | 9/2008 |
| WO | WO 2008/120098 | 10/2008 |
| WO | WO 2008/142513 | 11/2008 |

OTHER PUBLICATIONS

Lai et al. Selective fluorescence probes for dipeptidyl peptidase activity-fibroblast activation protein and dipeptidyl peptidase IV. Bioconjug Chem. Jul.-Aug. 2007;18(4):1246-50.*
Beta-alanine. PubChem https://pubchem.ncbi.nlm.nih.gov/compound/beta-alanine.*
Fernandez et al. N-Succinyl-(beta-alanyl-L-leucyl-L-alanyl-L-leucyl)doxorubicin: an extracellularly tumor-activated prodrug devoid of intravenous acute toxicity. J. Med. Chem. 2001, 44, 3750-3753.*
International Search Report for PCT/EP2013/078034 dated Jul. 2, 2014, six pages.
International Search Preliminary Report on Patentability for PCT/EP2013/078034 dated Jun. 2, 2015, thirty pages.
Gigot et al., "New compounds: Peptide derivatives of the antitumor agent N-phosphonoacetyl-l-aspartic acid", Journal of Pharmaceutical Sciences, vol. 73, No. 2, Feb. 1, 1984, pp. 275-277.
Edosada et al. "Peptide substrate profiling defines fibroblast activation protein as an endopeptidase of strict $Gly_2$-$Pro_1$-cleaving specificity" FEBS Lett.5 580:1581-1586 (2006).
Heinis et al. "Engineering a thermostable human prolyl endopeptidase for antibody-directed enzyme prodrug therapy" Biochem. 43:6293-6303 (2004).
Hu et al. "Discovery of matrix metalloproteases selective and activated peptide-doxorubicin prodrugs as anti-tumor agents" Bioorg. Med. Chem. Lett. 20:853-856 (2010).

(Continued)

*Primary Examiner* — Marcela M Cordero Garcia
*Assistant Examiner* — Jia-Hai Lee
(74) *Attorney, Agent, or Firm* — Nixon & Vanderhye P.C.

(57) ABSTRACT

The present invention relates to the field of oligopeptide prodrugs that are intended for the treatment of cancer. The selectivity of these prodrugs requires the presence of an (oligo)peptidic moiety and/or a protective capping group to ensure the prodrug stability in blood. It further in particular relates to the exemplary oligopeptidic moiety ALGP and to prodrugs comprising it. In particular it also relates to the capping group phosphonoacetyl and to prodrugs comprising this capping group.

Figure 1:
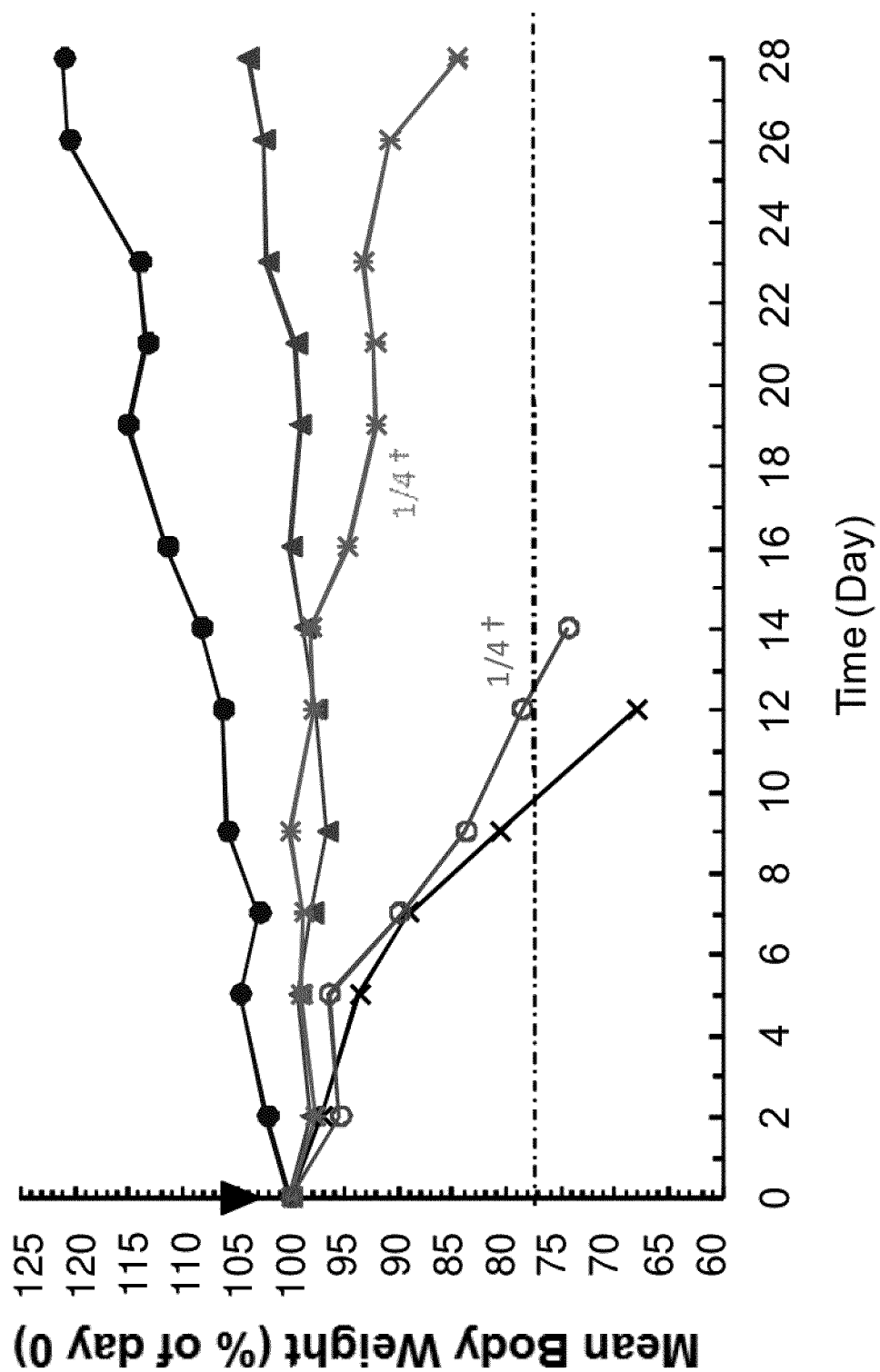

20 Claims, 19 Drawing Sheets
Specification includes a Sequence Listing.

(56) References Cited

OTHER PUBLICATIONS

Ravel et al. "Preclinical toxicity,toxicokinetics, and antitumoral efficacy studies of DTS-201, a tumor-selective peptidic prodrug of doxorubicin" Clin. Cancer Res. 14:1258-1265 (2008).
Shiose et al. "Systematic research of peptide spacers controlling drug release from macromolecular prodrug system, carboxymethyldextran polyalcohol-peptide-drug conjugates" Bioconjugate Chem. 20:60-70 (2009).
Partial translation of JPO Notification of Grounds of Rejections for JP 2015-550080, two pages, dated Nov. 28, 2017.
SIPO search report for CN 2013800678579, four pages, dated Apr. 6, 2017.
Partial translation of SIPO Office Action for CN 2013800678579, seven pages, dated Apr. 6, 2017.

* cited by examiner

MINIMALLY TOXIC PRODRUGS

This application is the U.S. national phase of International Application No. PCT/EP2013/078034 filed 27 Dec. 2013 which designated the U.S. and claims the benefit of U.S. Provisional Application No. 61/746,621 filed 28 Dec. 2012, the entire contents of each of which are hereby incorporated by reference.

FIELD OF THE INVENTION

The present invention relates to the field of oligopeptide prodrugs that are intended for the treatment of cancer. The selectivity of these prodrugs requires the presence of an (oligo)peptidic moiety and/or a protective capping group to ensure the prodrug stability in blood. It further in particular relates to the exemplary oligopeptidic moiety ALGP and to prodrugs comprising it. In particular it also relates to the capping group phosphonoacetyl and to prodrugs comprising this capping group.

BACKGROUND OF THE INVENTION

Therapy of cancer remains one of the major challenges of medicine today. Only a combined therapeutic approach will allow this problem to be mastered. This will involve surgery, classical chemotoxic chemotherapy, molecular targeted drugs and immunotherapy.

The major problem in the use of chemotoxic drugs is their low selectivity for cancer cells resulting in dose limiting and life threatening toxic side effects. The most common acute toxicity is myelotoxicity resulting in a severe leukopenia and thrombocytopenia. Some of the commonly used drugs have also a more specific toxicity. Doxorubicin (Dox), an anthracycline drug, is an 17 of such a chemotoxic drug that induces besides severe myelotoxicity a severe cardiotoxicity. These toxicities restrict its use above a cumulative dose of 500 mg/m$^2$.

Approaches used to increase tumor specificity of a drug are conjugation with (i) a tumor-recognizing molecule (e.g. receptor ligand; see, e.g., Safavy et al. 1999—J Med Chem 42, 4919-4924) or with (ii) a peptide that is cleaved preferentially in the immediate vicinity of tumor cells by proteases preferentially secreted or produced by tumor cells.

Tumor specific oligopeptidic prodrugs, such as prodrugs of doxorubicin, have been developed. In contrast to previous studies, these peptidic prodrugs were designed to be impermeable to cell membranes, to remain stable in the blood while being cleaved into the active drug by peptidases released in the extracellular space of solid tumors. These activating peptidases are not necessarily tumor specific but can increase the drug selectivity to the extent that these peptides are oversecreted in the extracellular space of solid tumors and play an important role in cancer cell invasion and metastasis. The originality of this approach is that it didn't target a single well known enzyme but all enzymatic activity that was found excreted by human tumoral cells maintained in culture. N-succinyl-beta-alanyl-L-leucyl-L-alanyl-L-leucyl-doxorubicin (Suc-βALAL-dox) was selected as such a candidate prodrug (Fernandez et al. 2001, J Med Chem 44:3750-3). Compared with unconjugated doxorubicin this prodrug is, in mice, about 5 times, and in dogs, 3 times less toxic. Chronic treatment with Suc-βALAL-dox proved to be significantly less cardiotoxic than with Dox at doses up to 8-fold higher in rats. The improved activity of Suc-βALAL-dox over Dox was observed in several tumor xenograft models (Dubois et al. 2002, Cancer Res 62:2327-31; Ravel et al. 2008, Clin Cancer Res 14:1258-65). Two enzymes, CD10 (neprilysin or calla antigen) and thimet oligopeptidase (TOP) have been identified later in tumor cell conditioned medium and in tumor cells as activators of Suc-βALAL-dox (Pan et al. 2003, Cancer Res 63:5526-31; Dubois et al. 2006, Eur J Cancer 42:3049-56) but other non-identified proteases may also be involved in the activation process.

A phase I clinical study with Suc-βALAL-dox was initiated by the biopharmaceutical company DIATOS SA. A myelotoxicity occurred at three times higher doses compared with Dox. No drug-related, severe cardiac adverse events were reported, even at very high cumulative doses (2750 mg/m$^2$). A clinical benefit was observed for 59% of evaluable patients (Delord et al., unpublished).

The main limitation of Suc-βALAL-dox is that leukopenia remains as an important toxicity and that experimentally higher antitumoral activity could only be observed at the cost of a still important myelotoxicity. Such myelotoxicity is expected to occur as the result from the sensitivity of the peptidic moiety of Suc-βALAL-dox to the hydrolysis by enzymes present in normal tissues.

WO 02/100353 specifically discloses chemotherapeutic prodrugs designed with a 3- to 6-amino acid oligopeptide cleavable by CD10. WO 02/00263 discloses prodrugs with a 3-amino acid oligopeptide cleavable by TOP and at least 1 prodrug with an amino acid oligopeptide (Leu-Ala-Gly) not cleavable by CD10. WO 00/33888 and WO 01/95945 disclose prodrugs with a 4- to 2O-amino acid oligopeptide comprising a non-genetically encoded amino acid at a fixed position, with said oligopeptide being cleavable by TOP. In WO 01/95945, at least 1 prodrug, with a βAla-Leu-Tyr-Leu oligopeptide, was reported to be resistant to CD10 proteolytic action. WO 01/95943 discloses prodrugs with a 3- to 4-amino acid oligopeptide comprising a fixed isoleucine, said oligopeptide preferably being resistant to TOP; no information on CD10-susceptibility or—resistance is given. A more general concept of a prodrug consisting of a drug linked to an oligopeptide (of at least 2 amino acids) itself linked to a terminal group is disclosed in WO 96/05863 and was later extended in WO 01/91798.

Other polymeric drug-conjugates of which the non-drug moiety is at least comprising a water-soluble polymer and a peptide (comprising 4 to 5 natural or non-natural amino acids) selectively cleavable by action of matrix metalloproteinases (MMPs) are disclosed in WO 02/07770. WO 03/094972 focuses on anti-tumor prodrugs that are activatable by the human fibroblast activation protein (FAPα); the prodrug comprises an oligopeptide of 4 to 9 amino acids with a cyclic amino acid at a fixed position. WO 99/28345 discloses prodrugs that are proteolytically cleavable by prostate-specific antigen in the oligopeptide of less than 10 amino acids present in the prodrug.

WO 97/34927 revealed the FAPα-scissable prodrugs Ala-Pro-7-amino-4-trifluoromethylcoumarin and Lys-Pro-7-amino-4-trifluoromethylcoumarin. WO 00/71571 focuses on FAPα-scissable prodrugs, with some further experimental investigations on proteolytic sensitivity to CD26 (dipeptidylpeptidase IV), the latter being considered as undesirable due to the relative abundance of CD26 also in non-malignant cells.

Other prodrugs activatable by FAPα include promellitin toxin (LeBeau et al. 2009, Mol Cancer Ther 8, 1378-1386), doxorubicin (Huang et al. 2011, J Drug Target 19, 487-496), thapsigargin (Brennen et al. 2012, J Natl Cancer Inst 104, 1320-1334), and a prodrugs comprising an oligopeptide of 4 to 9 amino acids with a cyclic amino acid at a fixed position (WO 03/094972). WO 01/68145 discloses MMP-cleavable but neprilysin (CD10)-resistant doxorubicin prodrugs (see Example 1001 therein) comprising a 3- to 8-amino acid oligopeptide. Metalloproteinase- and plasmin-sensitive doxorubicin prodrugs have been developed, as well as CNGRC-peptide conjugates with doxorubicin (Hu et al. 2010, Bioorg Med Chem Lett 20, 853-856; Chakravarty et al. 1983, J Med Chem 26, 638-644; Devy et al. 2004, FASEB J 18, 565-567; Vanhensbergen et al. 2002, Biochem Pharmacol 63, 897-908).

WO97/12624, WO97/14416, WO98/10651, WO98/18493 and WO99/02175 disclose peptide-comprising prodrugs wherein the peptide is cleavable by the prostate-specific antigen (PSA).

Common to all above prodrugs is the presence of a protecting or capping moiety, usually covalently linked to the N-terminal side of the oligopeptide, which adds to the stability of the prodrug and/or adds to the prevention of internalization of the prodrug into a cell such as a target cell. Such protecting or capping moieties include non-natural amino acids, β-alanyl or -succinyl groups (e.g. WO 96/05863, U.S. Pat. No. 5,962,216). Further stabilizing protecting or capping moieties include diglycolic acid, maleic acid, pyroglutamic acid, glutaric acid, (e.g., WO 00/33888), a carboxylic acid, adipic acid, phthalic acid, fumaric acid, naphthalene dicarboxylic acid, 1,8-naphtyldicarboxylic acid, aconitic acid, carboxycinnamic acid, triazole dicarboxylic acid, butane disulfonic acid, polyethylene glycol (PEG) or an analog thereof (e.g., WO 01/95945), acetic acid, 1- or 2-naphthylcarboxylic acid, gluconic acid, 4-carboxyphenyl boronic acid, polyethylene glycolic acid, nipecotic acid, and isonipecotic acid (e.g., WO 02/00263, WO 02/100353), succinylated polyethylene glycol (e.g., WO 01/91798). A new type of protecting or capping moiety was introduced in WO 2008/120098, being a 1,2,3,4 cyclobutanetetracarboxylic acid. The protecting or capping moiety in WO 02/07770 may be polyglutamic acid, carboxylated dextranes, carboxylated polyethylene glycol or a polymer based on hydroxyprolyl-methacrylamide or N-(2-hydroxyprolyl)methacryloylamide.

BRIEF DESCRIPTION OF THE INVENTION

The prodrugs of the invention have the general structure:

[C$_x$-OP]$_y$-D, wherein C is a capping group;
OP is an oligopeptidic moiety;
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group, and wherein, if y is greater than 1, the multiple OP moieties are individually linked to each other directly or via a linker or spacing group, with one of the OP moieties being linked directly, via a linker or via a spacing group to D. Alternatively, the multiple OP moieties can each be individually linked to D directly, via a linker, or via a spacing group. An intermediate constellation is included wherein some of the multiple OP moieties are individually linked to D directly, via a linker, or via a spacing group, and wherein some of the multiple OP moieties are themselves each individually linked to each other directly or via a linker or spacing group, with one of the OP moieties being linked directly, via a linker or via a spacing group to D;
or a pharmaceutically acceptable salt thereof.

In particular, the oligopeptide moiety in the above structure is a tetrapeptide moiety with the sequence Ala-Leu-Gly-Pro (3-letter code), also referred to as ALGP (1-letter code; SEQ ID NO:1); or Ala-Leu-Ala-Leu (3-letter code), also referred to as ALAL (1-letter code; SEQ ID NO:2), and/or the capping group C in the above structure is a phosphonoacetyl group, and/or the drug in the above structure is doxorubicin (hereinafter also referred to as DOX or Dox). Alternatively, the structure of the tetrapeptide is ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10). Accordingly, in one embodiment the structure of the tetrapeptide in the above general structure is selected from the group consisting of ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), and KLKP (SEQ ID NO:10). In particular the tetrapeptide in the above general structure is selected from ALGP (SEQ ID NO:1), or KLGP (SEQ ID NO:6); even more in particular the tetrapeptide in the above general structure is ALGP (1-letter code; SEQ ID NO:1). When present, said linker or spacing group in the above prodrugs or salts thereof may be a self-eliminating linker or spacing group.

Pharmaceutically acceptable salts of the above prodrug(s) are also part of the inventions.

The invention further relates to compositions comprising one of the above prodrugs or salts thereof, or a combination of any thereof, and at least one of a solvent, diluent or carrier.

The invention encompasses the above prodrug or salt thereof, or the above composition comprising it for use in the treatment of a cancer. Methods of treating a cancer are also part of the invention, said methods comprising administering to a subject having cancer said prodrug or salt thereof or said composition, said administering resulting in the treatment of said cancer. In particular, the effective amounts of said prodrug or salt thereof, or of said composition is not causing severe leukopenia or cardiac toxicity.

Methods of producing the above prodrugs are further part of the invention, said methods comprising the steps of:
(i) obtaining the drug;
(ii) linking the drug to a capped oligopeptidic moiety, resulting in the prodrug; or, alternatively,
(ii') linking the drug to an oligopeptidic moiety followed by linking the capping group to the oligopeptidic moiety, resulting in the prodrug; and
(iii) purifying the prodrug obtained in step (ii) or (ii').

The invention further includes methods of producing and of screening candidate prodrugs, such candidate prodrugs having the general structure

[C$_x$-OP]$_y$-D, wherein C is a capping group;
OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP); in particular OP is a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10);
even more in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group, and wherein, if y is greater than 1, the multiple OP moieties are individually linked to each other directly or via a linker or spacing group and/or are individually linked to D directly or via a linker or spacing group; and wherein said screening method comprises the steps of:
(i) obtaining the drug D;
(ii) conjugating the drug D to a GP-, AP- or KP-dipeptide to obtain a GP-D, AP-D or KP-D as dipeptide-drug intermediate prodrug;
(iii) contacting each of drug D and dipeptide-drug intermediate prodrug GP-D, AP-D or KP-D independently with in vitro cultured cells;
(iv) determining the cytotoxicity of drug D and dipeptide-drug intermediate prodrug GP-D, AP-D or KP-D;
(v) identifying from (iv) a dipeptide-drug intermediate prodrug GP-D, AP-D or KP-D with comparable cytotoxic activity as drug D; and
(vi) selecting $[C_x\text{-OP}]_y\text{-D}$ corresponding to dipeptide-drug intermediate prodrug GP-D, AP-D or KP-D identified in step (v) as candidate prodrug.

Alternatively, in said screening methods are methods of screening candidate prodrugs, the candidates to be tested have the general structure $[C_x\text{-OP}]_y\text{-D},$ wherein C is a capping group;
OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises a carboxy-terminal proline, wherein said proline is linked directly or via a linker or spacing group to the drug D; in particular OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP); more in particular a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); even more in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group, and wherein, if y is greater than 1, the multiple OP moieties are individually linked to each other directly or via a linker or spacing group and/or are individually linked to D directly or via a linker or spacing group; and
wherein said screening method is comprising the steps of:
(i) obtaining the drug D;
(ii) conjugating the drug D to $[C_x\text{-OP}]_y$ to obtain a $[C_x\text{-OP}]_y\text{-D}$ prodrug;
(iii) contacting each of drug D and prodrug $[C_x\text{-OP}]_y\text{-D}$ independently with in vitro cultured cells;
(iv) determining the cytotoxicity of drug D and prodrug $[C_x\text{-OP}]_y\text{-D}$;
(v) identifying from (iv) a prodrug $[C_x\text{-OP}]_y\text{-D}$ with comparable cytotoxic activity as drug D; and
(vi) selecting $[C_x\text{-OP}]_y\text{-D}$ identified in step (v) as candidate prodrug.

In another alternative, said screening are methods of screening candidate prodrugs having the general structure $[C_x\text{-OP}]_y\text{-D},$ wherein C is a capping group;
OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises a carboxy-terminal proline, wherein said proline is linked directly or via a linker or spacing group to the drug D; in particular OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP); more in particular a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); even more in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group, and wherein, if y is greater than 1, the multiple OP moieties are individually linked to each other directly or via a linker or spacing group and/or are individually linked to D directly or via a linker or spacing group;
wherein said method is comprising the steps of:
(i) obtaining the drug D;
(ii) conjugating the drug D to $[C_x\text{-OP}]_y$ to obtain a $[C_x\text{-OP}]_y\text{-D}$ prodrug;
(iii) contacting prodrug $[C_x\text{-OP}]_y\text{-D}$ for 5 h at 37° C. with in vitro cultured cells;
(iv) determining the conversion of prodrug $[C_x\text{-OP}]_y\text{-D}$ into free drug D;
(v) identifying from (iv) a prodrug $[C_x\text{-OP}]_y\text{-D}$ which is converted by at least 50% to D; and
(vi) selecting $[C_x\text{-OP}]_y\text{-D}$ identified in step (v) as candidate prodrug.

In yet another alternative, in said screening methods are methods of screening candidate prodrugs, the candidates to be tested have the general structure $[C_x\text{-OP}]_y\text{-D},$ wherein C is a capping group;
OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP); more in particular a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10);
even more in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group, and wherein, if y is greater than 1, the multiple OP moieties are individually linked to each other directly or via a linker or spacing group and/or are individually linked to D directly or via a linker or spacing group; and wherein said screening method is comprising the steps of:
(i) obtaining the drug D;
(ii) conjugating the drug D to a GP-, AP- or KP-dipeptide to obtain a GP-D, AP-D or KP-D prodrug;
(iii) contacting prodrug GP-D, AP-D or KP-D for 3 h at 37° C. with isolated FAP and/or DPIV peptidases;
(iv) determining the conversion of prodrug GP-D, AP-D or KP-D into free drug D;
(v) identifying from (iv) a prodrug GP-D, AP-D or KP-D which is converted by at least 50% to D; and
(vi) selecting $[C_x\text{-}OP]_y\text{-}D$ corresponding to prodrug GP-D, AP-D or KP-D identified in step (v) as candidate prodrug.

Further envisaged said screening include methods of screening candidate prodrugs having the general structure

wherein C is a capping group;
OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises a carboxy-terminal proline, wherein said proline is linked directly or via a linker or spacing group to the drug D; in particular OP is a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP); more in particular a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); even more in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group, and wherein, if y is greater than 1, the multiple OP moieties are individually linked to each other directly or via a linker or spacing group and/or are individually linked to D directly or via a linker or spacing group;

wherein said screening method is comprising the steps of:
(i) obtaining the drug D;
(ii) conjugating the drug D to $[C_x\text{-}OP]_y$ to obtain a $[C_x\text{-}OP]_y\text{-}D$ prodrug;
(iii) contacting prodrug $[C_x\text{-}OP]_y\text{-}D$ for 3 h to 24 h at 37° C. with isolated CD10 and/or TOP peptidases and with isolated FAP and/or DPIV peptidases;
(iv) determining the conversion of prodrug $[C_x\text{-}OP]_y\text{-}D$ into free drug D;
(v) identifying from (iv) a prodrug $[C_x\text{-}OP]_y\text{-}D$ which is converted by at least 50% to D; and
(vi) selecting $[C_x\text{-}OP]_y\text{-}D$ identified in step (v) as candidate prodrug.

In any of the above alternative screening methods said capping group C may be a phosphonoacetyl group.

In any of the above alternative screening methods said drug D may be selected from the group consisting of maytansine, geldanamycin, paclitaxel, docetaxel, campthothecin, vinblastine, vincristine, vindesine, methothrexate, aminopterin, amrubicin, or a derivative of any thereof.

In the above methods, and when present, said linker or spacing group may be a self-eliminating linker or spacing group.

The invention further relates to kits comprising a container comprising an above-described prodrug or salt thereof or comprising a composition comprising such prodrug or salt thereof.

LEGENDS TO FIGURES

FIG. 1. Effect of PhAc-peptide-Dox conjugates on the body weight of OF-1 normal mice (n=4). Drugs or controls were administered by the i.v. route on day 0. The mice receiving a constant volume (10 μL/g) of either saline (-●-) or of the different dosing solutions: PhAc-ALAL-Dox 80 μmolKg (-▲-) and 160 μmol/kg (-×-); PhAc-ALGP-Dox at 240 μmol/kg (-*-) and 320 μmol/kg (-○-). Results represent the mean body weight evolution.

Figure 2:
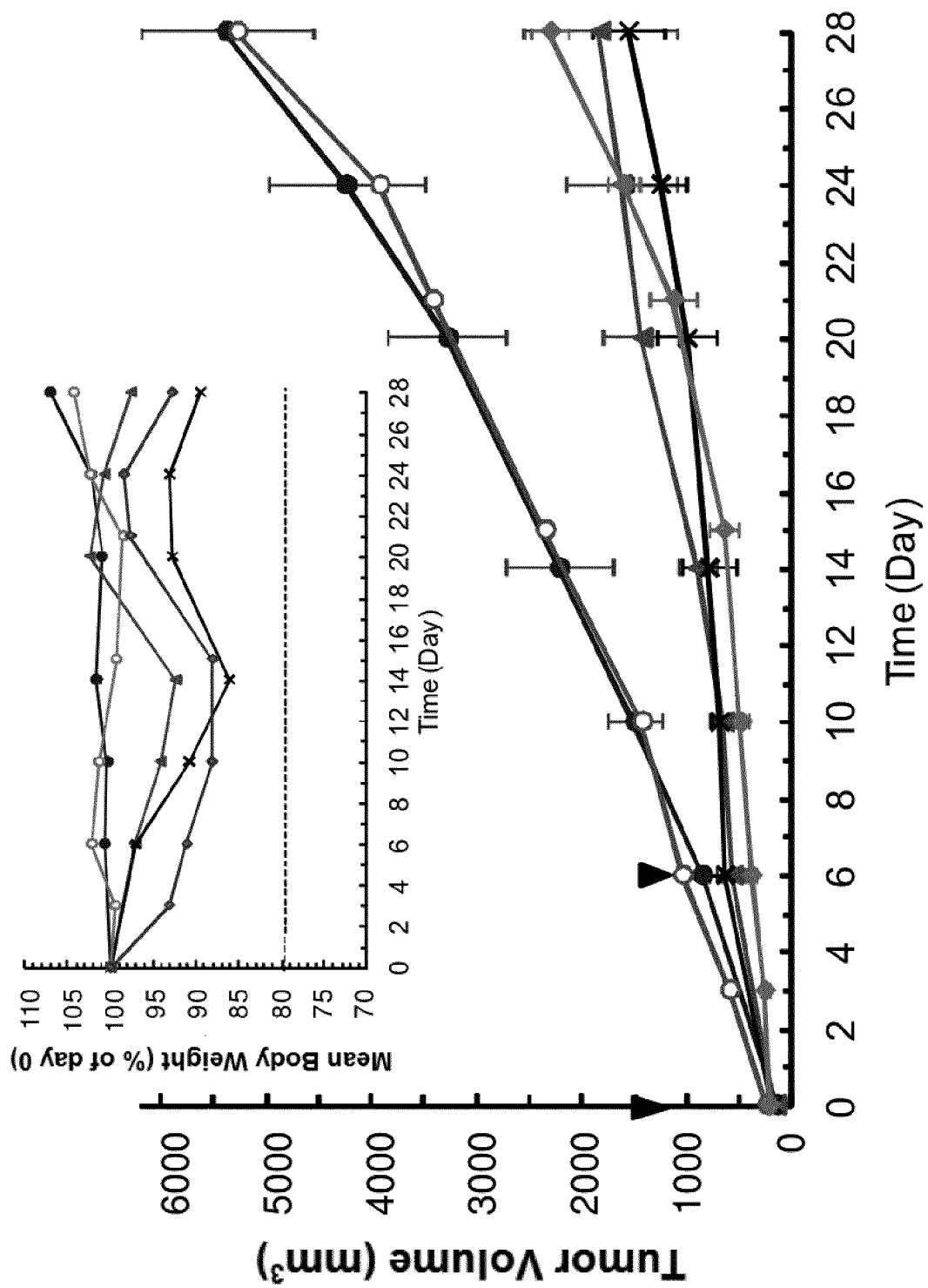

FIG. 2. Efficacy study of PhAc-ALGP-Dox in comparison with free Doxorubicin in NMRI nude mice bearing LS174T colon carcinoma human xenografts. Drugs or controls were administered by the i.v. route on day 0 and day 7. The mice receiving a constant volume (10 μL/g) of either saline (-●-;-○-) or of the different dosing solutions: PhAc-ALGP-Dox 140 μmolKg (-▲-) and 160 μmol/kg (-×-); Dox 15 μmol/kg (-◆-). Results represent the mean body weight and tumor volume evolution±SEM (n=4).

Figure 3:
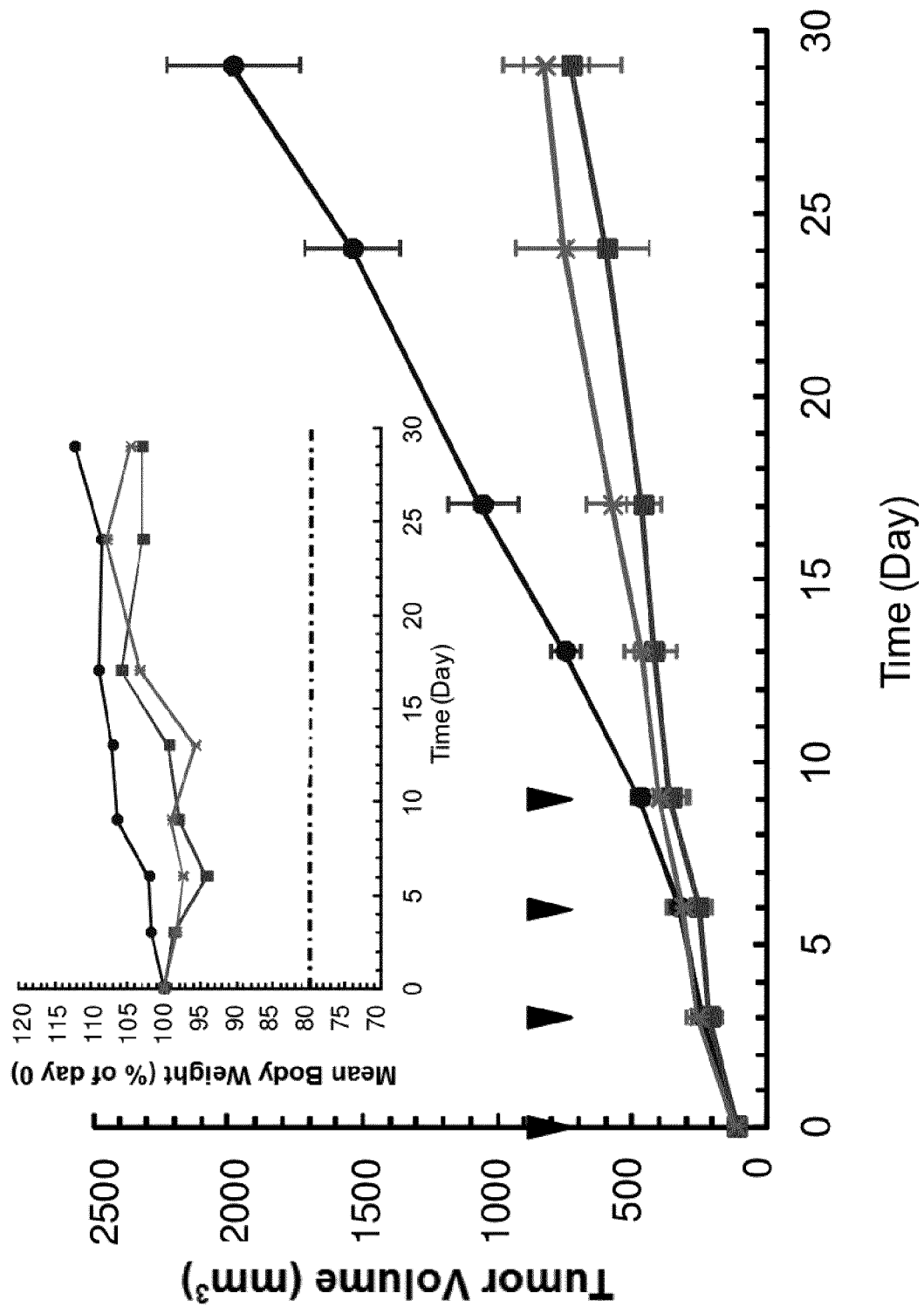

FIG. 3. Efficacy study of PhAc-ALGP-Dox in comparison with free Doxorubicin in NMRI nude mice bearing MX-1 mammary carcinoma human xenografts. Drugs or controls were administered by the i.v. route on day 0, 3, 6 and 9. The mice receiving a constant volume (10 μL/g) of either saline (-●-) or of the different dosing solutions: PhAc-ALGP-Dox 100 μmolKg (-*-); and Dox 8 μmol/kg (-■-). Results represent the mean body weight and tumor volume evolution±SEM (n=4).

Figure 4:
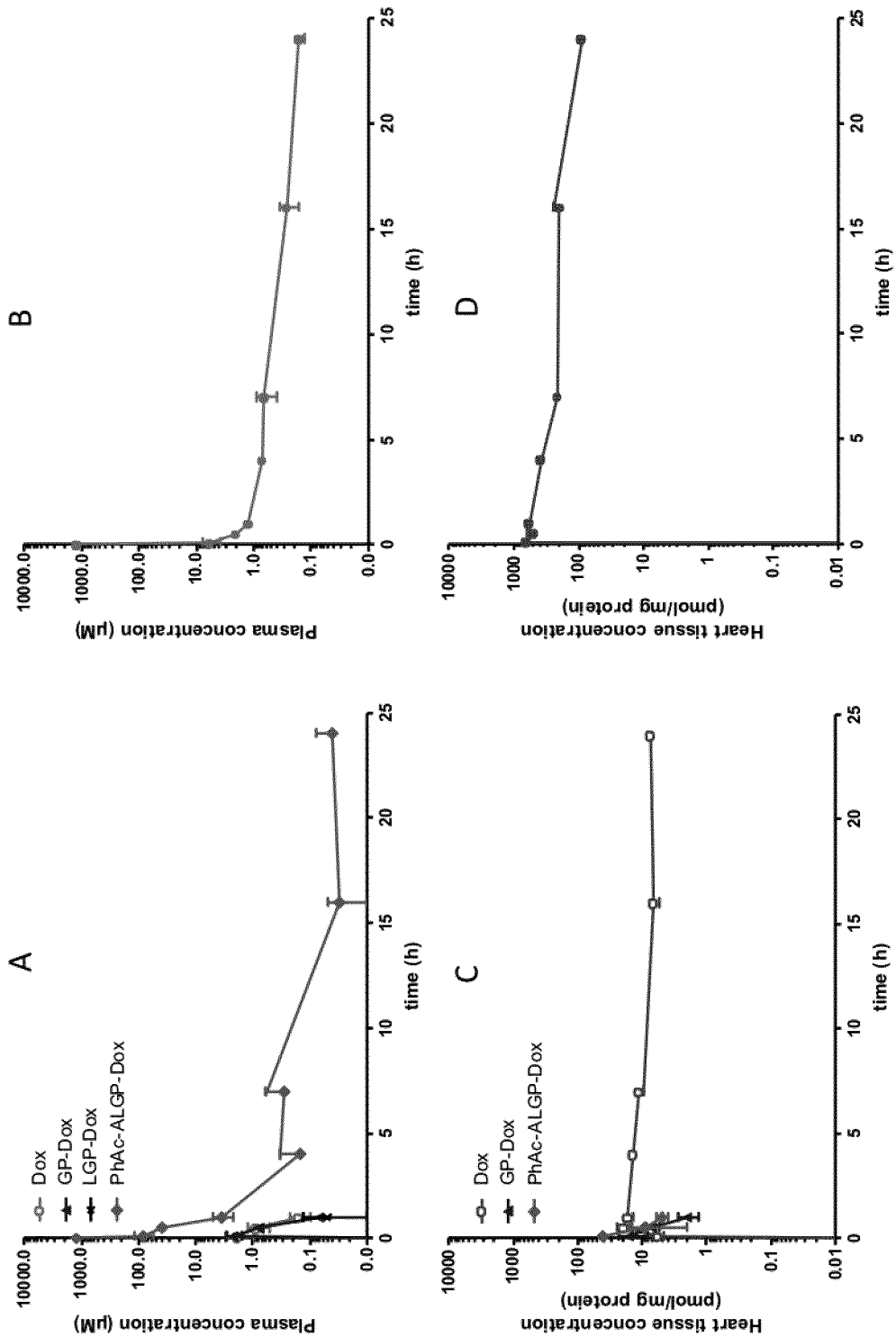

FIG. 4. Time evolution of plasma concentration (A, B) and of cardiac tissue concentration (C, D) of Doxorubicin or PhAc-ALGP-Dox and its metabolites after i.v. bolus injection to OF-1 female wild type mice at the dose of 86.2 μmol/kg. Results represent the mean concentration±SD (n=3).

Figure 5:
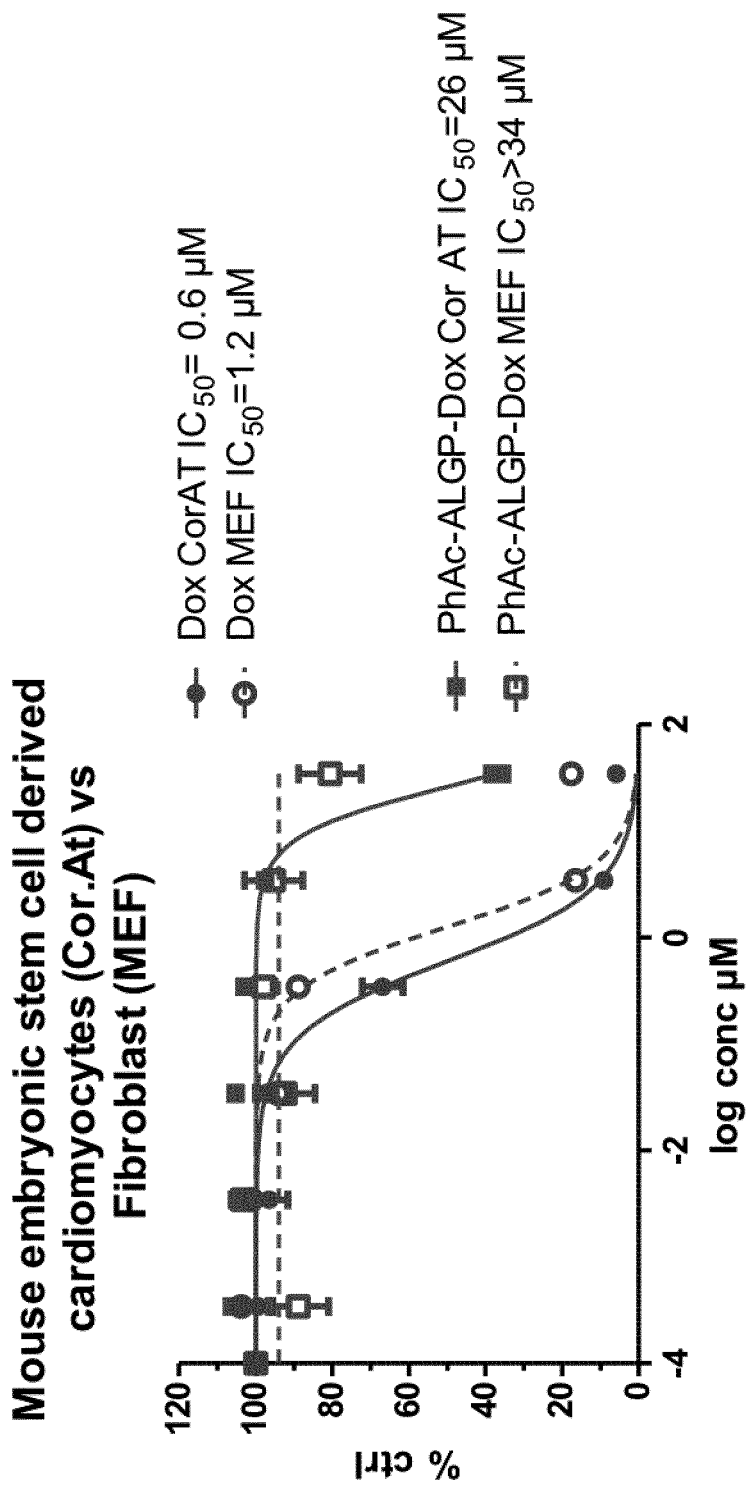

FIG. 5. In vitro cellular toxicity of PhAc-ALGP-Dox and Doxorubicin on Cor.At® cells (mouse embryonic stem cell derived cardiomyocytes). As non-specific control, the test was also performed on inactivated mouse embryonic fibroblasts (MEF). Cells were cultured for 48 h in the presence of drugs and a neutral red uptake test was performed to determine cell viability. Results represent the cytotoxicity curves. The $IC_{50}$ values were calculated from the cytotoxicity curves using the Prism GraphPad software 5.0.

Figure 6:
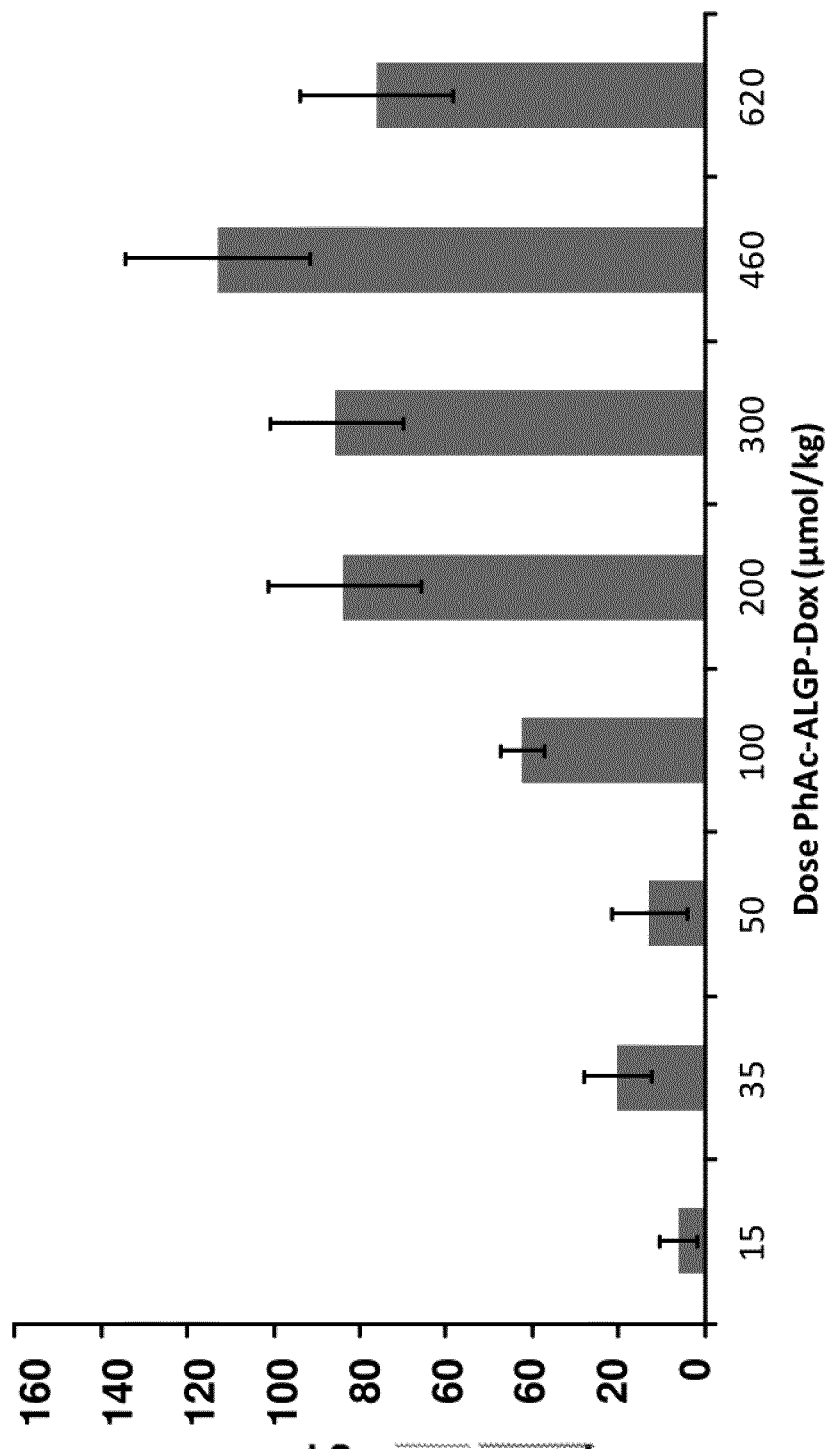

FIG. 6. PhAc-ALGP-Dox was administered at increasing concentrations (15, 35, 50, 100, 200, 300, 460, 620 μmol/kg) by intravenous injection to NMRI nude mice bearing LoVo colon carcinoma xenografts (3 mice per group). After 24 hours, mice were sacrificed and tumors were collected. Doxorubicin tumor concentration was determined after extraction by HPLC analysis. Results represent the average Doxorubicin tumor concentration (pmol/mg protein)±SD.

Figure 7:
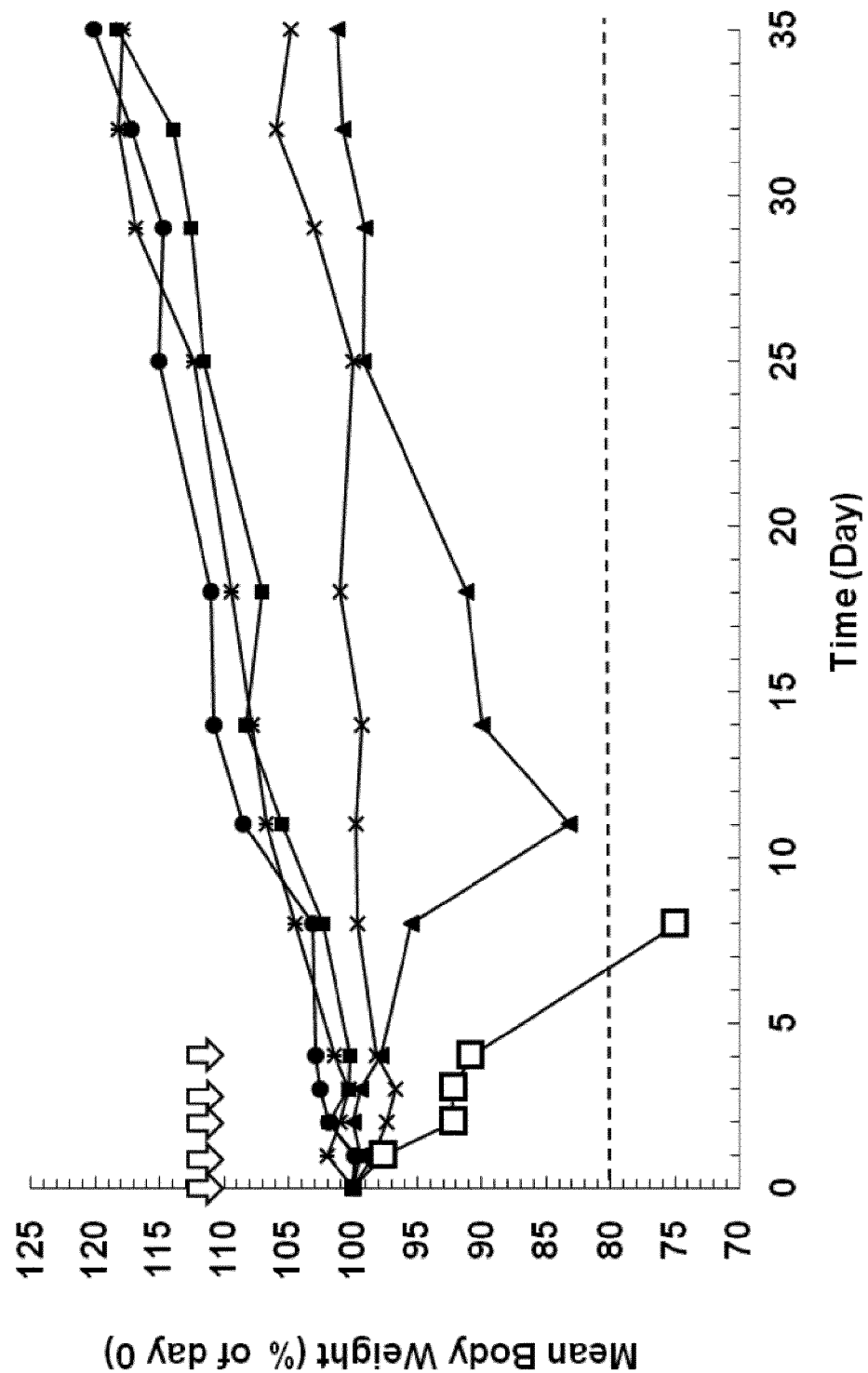

FIG. 7. Toxicity study of PhAc-ALGP-Dox after single and multiple intraperitoneal (ip) injections in OF-1 mice.

Animals were treated with PhAc-ALGP-Dox with different treatment schedules: at 56 μmol/kg 5× (Q1D5 -*-); at 28 μmol/kg 10× (2Q1D5 -■-); at 560 μmol/kg 1× (-□-); at 112 μmol/kg 5× (Q1D5 -▲-); at 56 μmol/kg 10× (2Q1D5 -×-).

Figure 8:
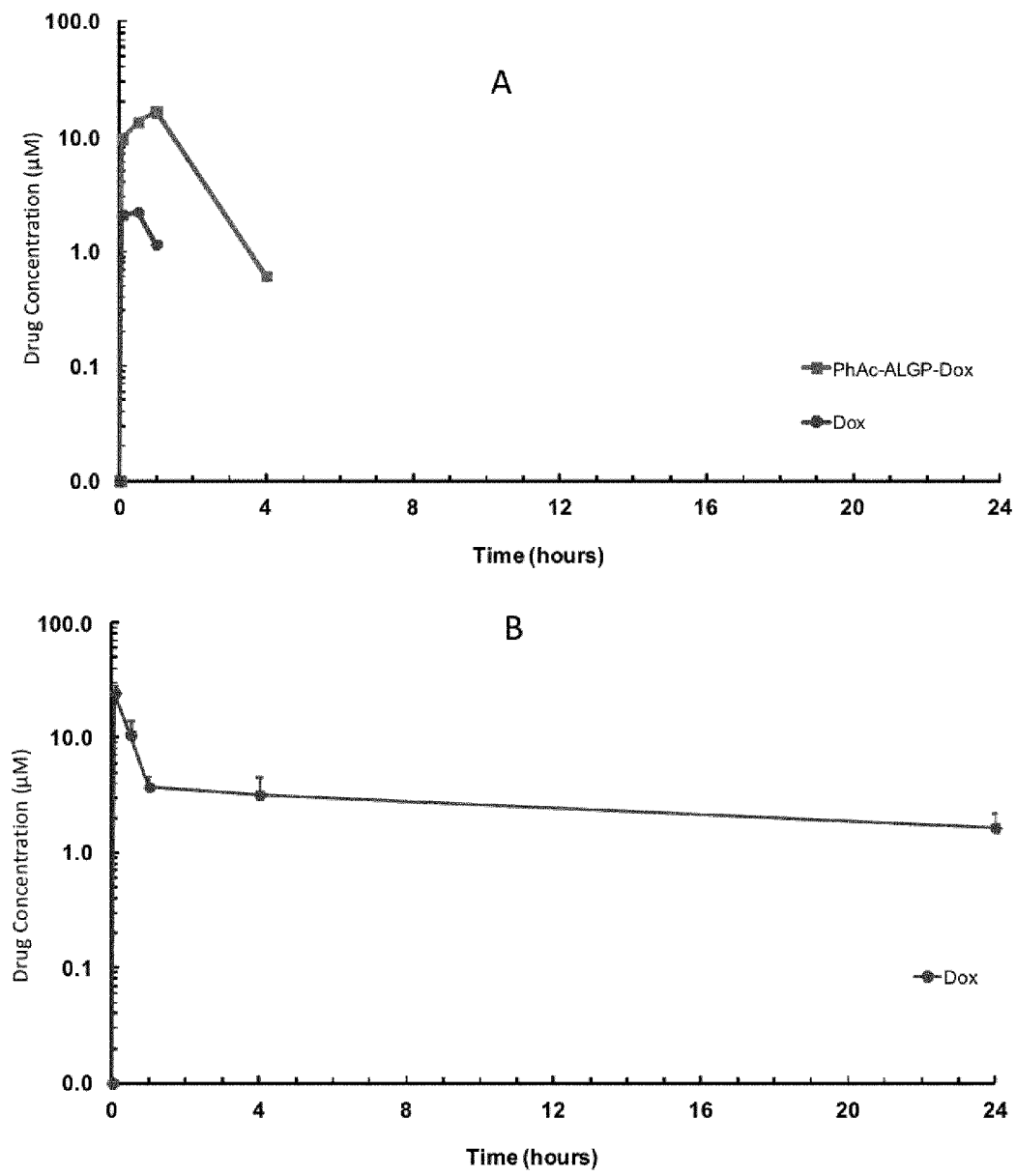

FIG. 8. Time evolution of blood concentration of PhAc-ALGP-Dox and its metabolites (A) or of Doxorubicin (B) after intraperitoneal injection to OF-1 female wild type mice at the equimolar dose of 92 μmol/kg. Results represent the mean concentration±SD (n=3).

Figure 9:
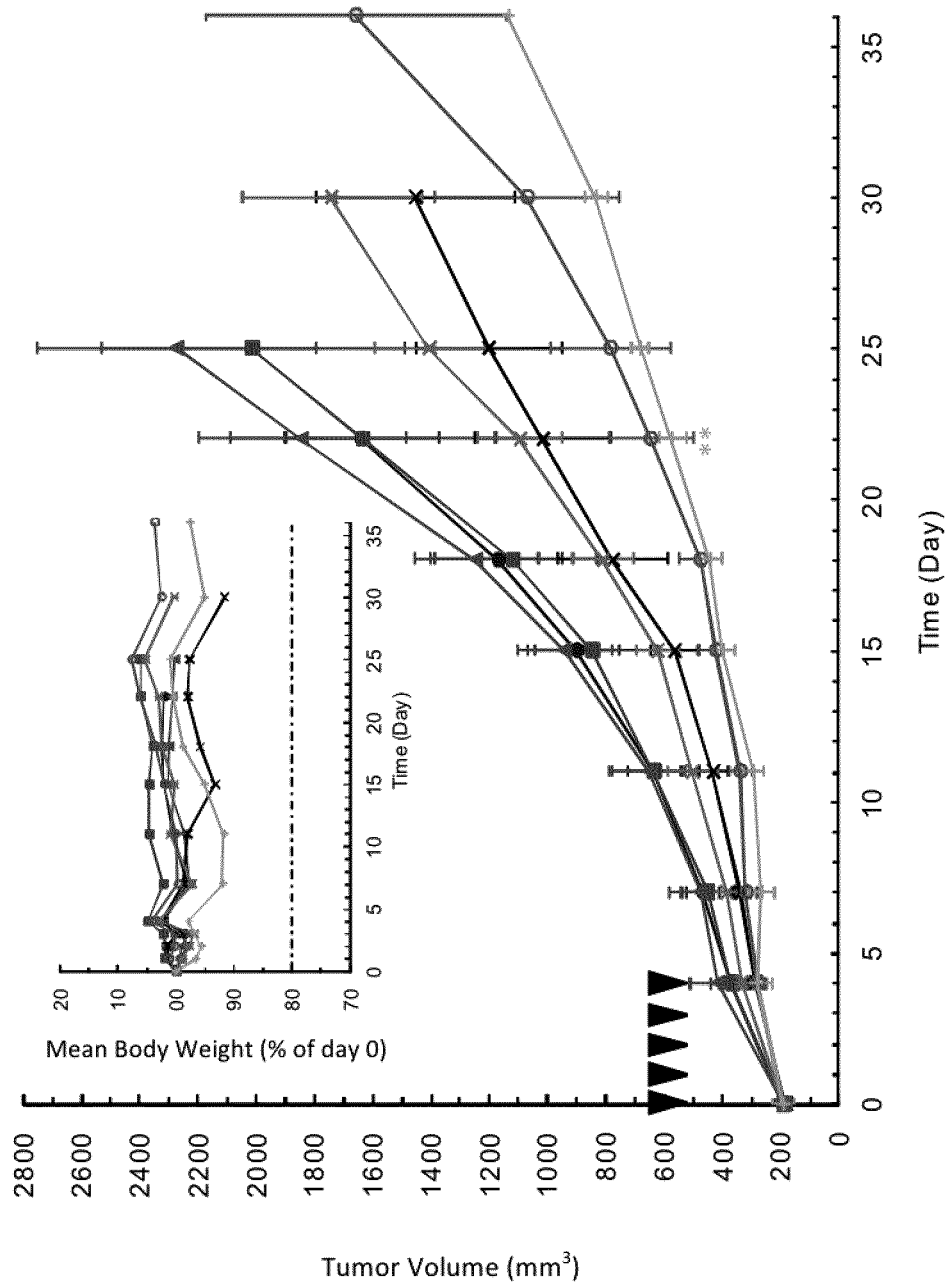

FIG. 9. Efficacy study of PhAc-ALGP-Dox in comparison with free Doxorubicin in NMRI nude mice bearing LoVo colon carcinoma human xenografts. Drugs or controls were administered by the i.p. route twice a day for five consecutive days (arrows). The mice receiving a constant volume (10 μL/g) of either saline (-●-) or of the different dosing solutions: PhAc-ALGP-Dox 25 μmol/kg (*), 35 μmol/kg (○) and 50 μmol/kg (+); Dox 0.5 μmol/kg (■), 1 μmol/kg (▲) and 2 μmol/kg (×). Results represent the mean body weight and tumor volume evolution±SEM (n=4). ** Statistically different with $p<0.05$ from Dox 2 μmol/kg (Mann-Whitney t test of the Graph Pad Prism 5.0 software).

Figure 10:
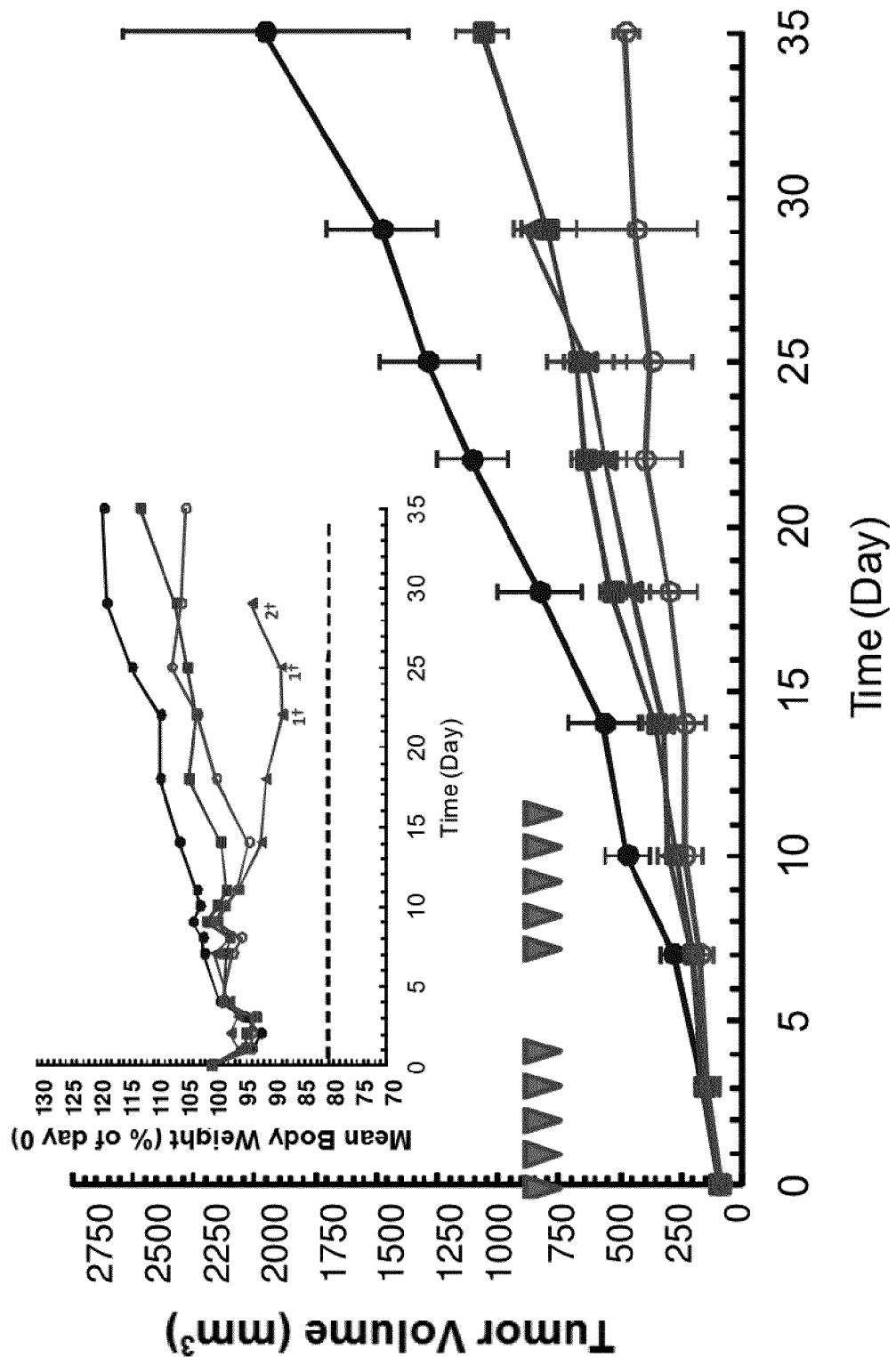

FIG. 10. Efficacy study of PhAc-ALGP-Dox in comparison with free Doxorubicin in NMRI nude mice bearing MX-1 mammary carcinoma human xenografts. Drugs or controls were administered by the i.p. route twice a day for five consecutive days (arrows). Treatment was repeated with 72 hours interval between two cycles. The mice receiving a constant volume (10 μL/g) of either saline (●) or of the different dosing solutions: PhAc-ALGP-Dox 50 μmol/kg (○), Dox 1 μmol/kg (■), and 1.5 μmol/kg (▲). Results represent the mean body weight and tumor volume evolution±SEM (n=6). †=dead mouse.

Figure 11:
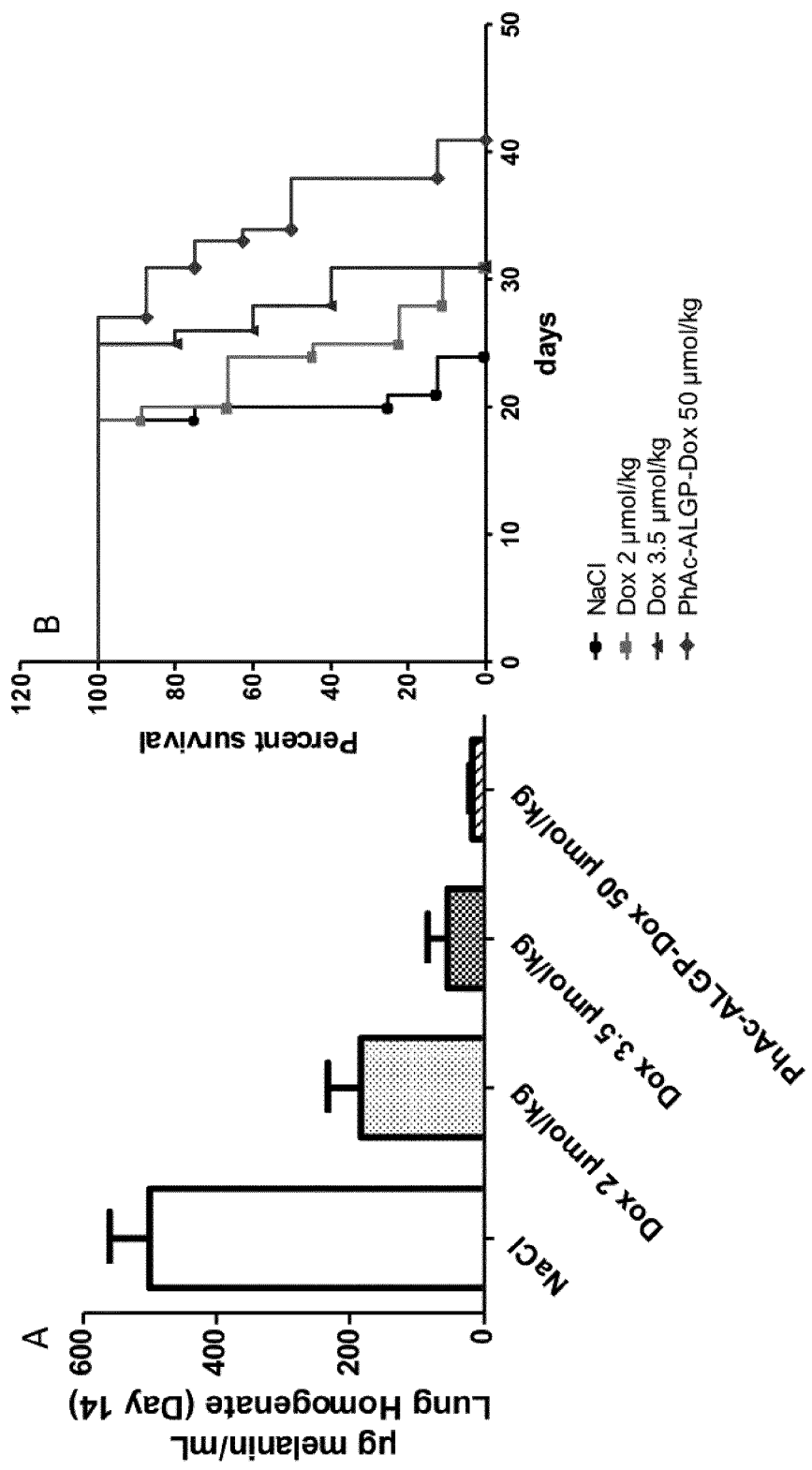

FIG. 11. Evaluation of PhAc-ALGP-Dox efficacy in comparison with Doxorubicin in the B16-F10 lung metastatic melanoma model. Graph on the left side represents quantification of melanin of lung metastasis at day 14 after injection of B16F10 tumor cells. Graph on the right side show the survival curves.

Figure 12:
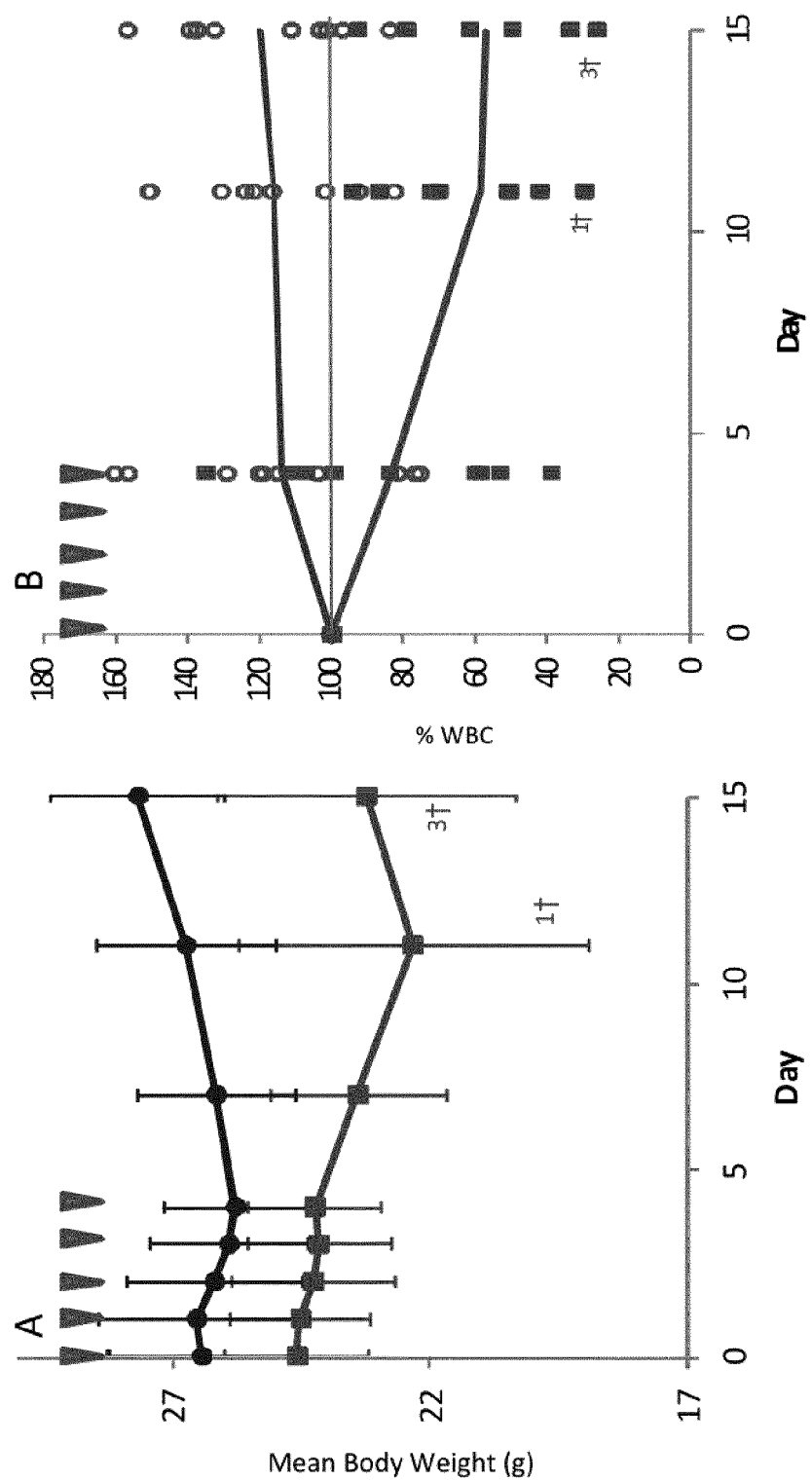

FIG. 12. Evaluation of PhAc-ALGP-Dox leucopenic effect in comparison with Doxorubicin. CD1 mice received twice daily intraperitoneal injections of PhAc-ALGP-Dox 35 μmol/kg (●) or of Doxorubicin 3.5 μmol/kg (■) for five consecutive days. The mice body weight evolution was recorded (A). Blood was collected from the tail vein in heparinised Microvettes tubes (Starsted) at day 4, 11 and 15 after treatment initiation. Peripheral white blood cells (WBC) were counted using the SCILvet abc hematologic analyzer (B). The increase or decrease in WBC is expressed as a percentage of WBC on day 0 (100%) for each mouse. The curves show evolution of the mean percentages.

Figure 13:
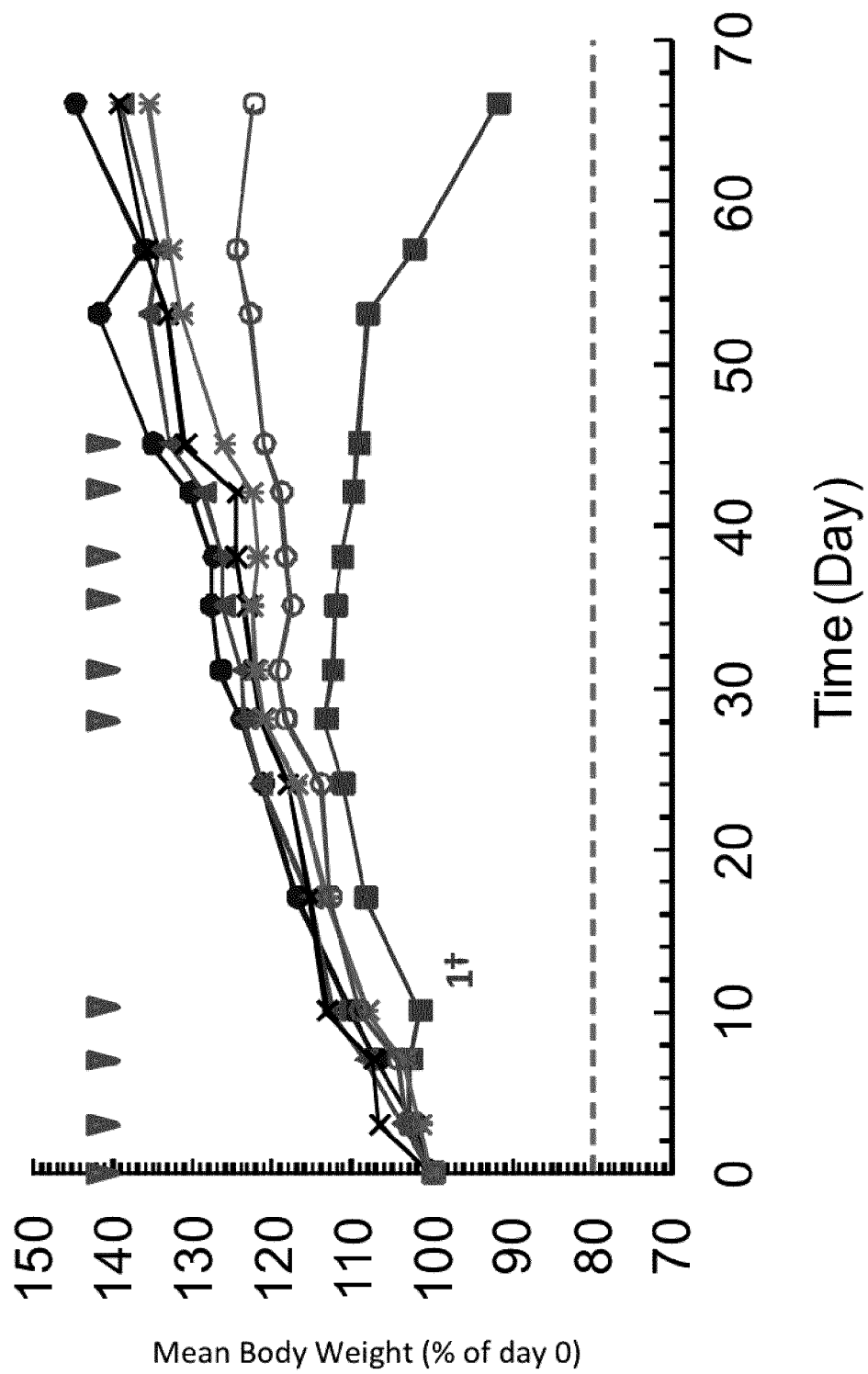

FIG. 13. Evaluation of chronic cardiotoxicity of PhAc-ALGP-Dox in CD-1 mice. Animals received 10 intravenous injections (arrows) of saline (●); Doxorubicin 6.9 μmol/kg (■) or of PhAc-ALGP-Dox at 13.8 (▲), 27.6 (×), 55.2 (*) and 82.8 μmol/kg (○). Results represent the evolution of the average relative body weight (%). †=dead mouse.

Figure 14:
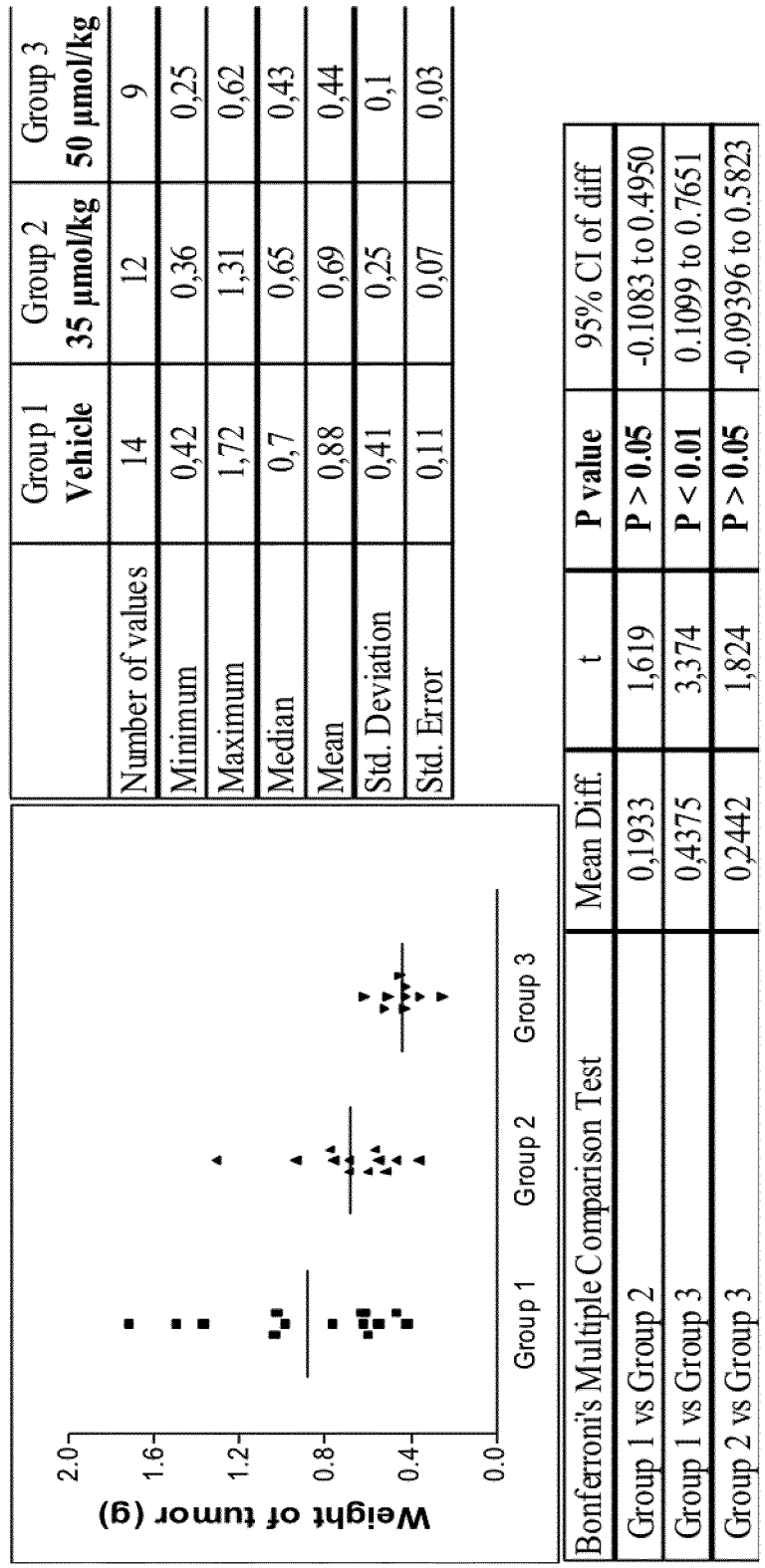

FIG. 14. Evaluation of the antitumor effect of PhAc-ALGP-dox in SCID mice bearing orthotopic HCT116 human colon tumors. SCID mice were injected orthotopically (in the caecum) with human HCT116 colon tumor cells. One group was treated with saline while groups 2 and 3 received 10 intraperitoneal injections (2Q1D5) of 35 and 50 μmol/kg of PhAc-ALGP-doxorubicin. Primary tumor weights were recorded on day 34 post cell inoculation.

Figure 15:
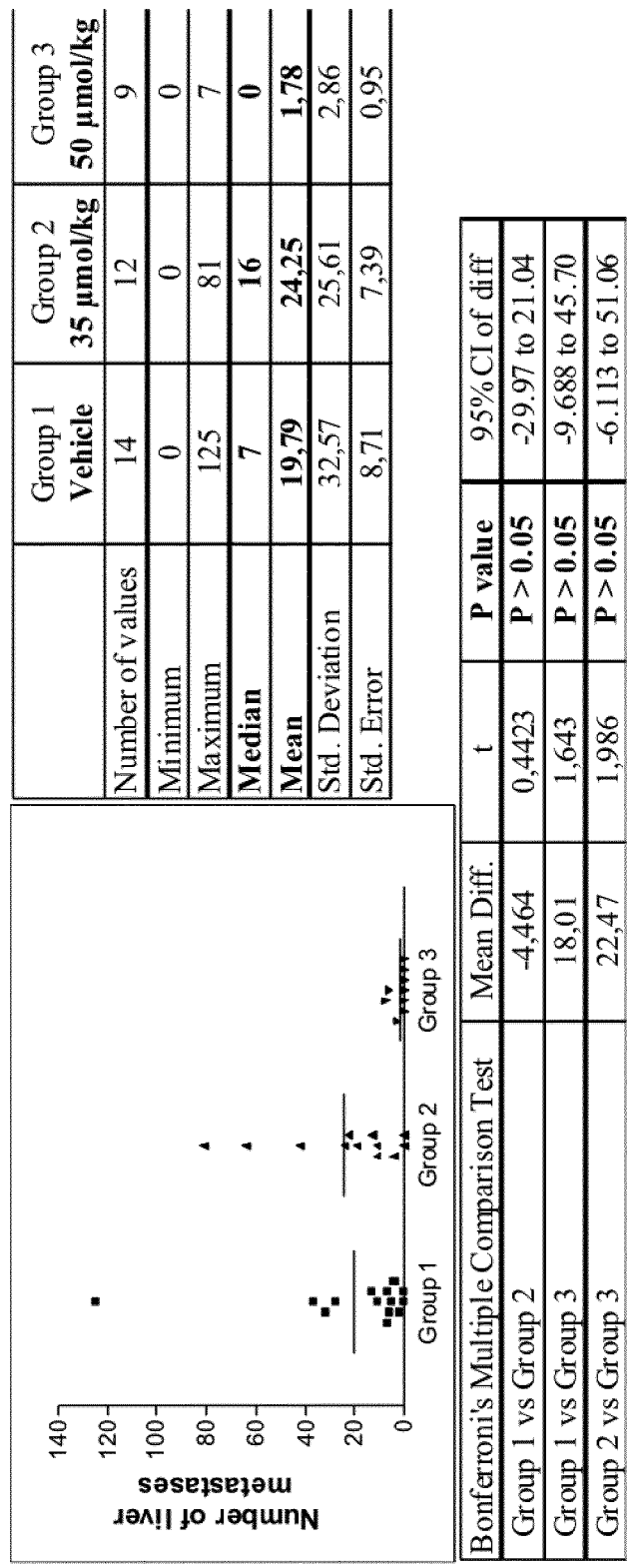

FIG. 15. Evaluation of the antimetastatic effect (in liver) of PhAc-ALGP-dox in SCID mice bearing orthotopic HCT116 human colon tumors. SCID mice were injected orthotopically (in the caecum) with human HCT116 colon tumor cells. One group was treated with saline while groups 2 and 3 received 10 intraperitoneal injections (2Q1D5) of 35 and 50 μmol/kg of PhAc-ALGP-doxorubicin. Liver metastases were recorded on day 34 post cell inoculation.

Figure 16:
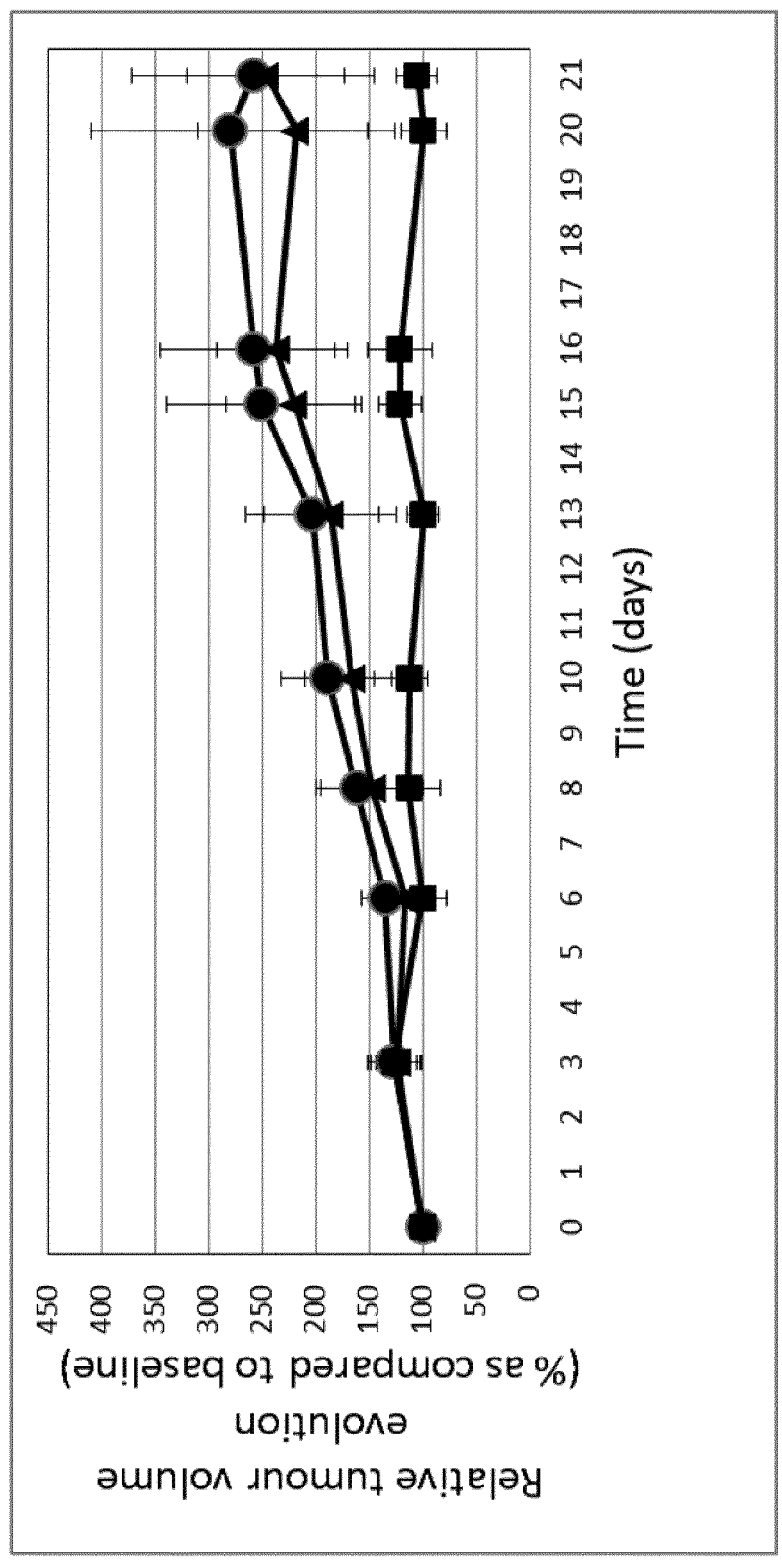

FIG. 16. Effect of PhAc-ALGP on a UZLX-STS3 xenograft model. UZLX-STS3 is a tissue xenograft derived from a patient diagnosed with dedifferentiated liposarcoma (DDLPS). During passaging, ex-mouse tumors revealed the same morphological and molecular features as the original biopsy collected from the patient during the surgery (i.e. MDM2 gene amplification, MDM2 immunopositivity). In previous xenografts not given by perfusion this sarcoma tumor model was completely resistant to free doxorubicin given at its maximum tolerated dose.

A total of 24 mice were bilaterally transplanted with UZLX-STS3 (tissue xenografts of passage 10). Animals were randomly assigned to three different groups: a control group (saline; -●-); A PhAc-ALGP-doxorubicin group (cumulative dose 1.20 mmol/kg; -■-) and a doxorubicin group (cumulative dose 0.03 mmol/kg; -▲-). The drugs were administered intraperitoneally during 7 days by continuous release via an Alzet® osmotic pump, with delivery rate of 0.5 μl/h over 7 days. The experiment lasted 21 days (7 days of treatment+14 days of observation). Tumor volume and mouse body weight were evaluated at baseline and subsequently three times per week until the end of each experiment. After 21 days mice were sacrificed. Tumor volume is recorded 3× weekly by 3-dimensional caliper measurement. Data are presented as the average of the relative tumor volumes per group±standard deviation.

The comparison between the tumor volumes on day zero and the volumes on the last day of the experiments was done by Wilcoxon's matched paired test. The comparisons between different groups were performed using the Mann-Whitney U test (relative tumor volumes, histologic assessment). $P<0.05$ was considered as statistically significantly different. The STATISTICA software (StatSoft, version 12.0) was used for all the calculations.

Figure 17:
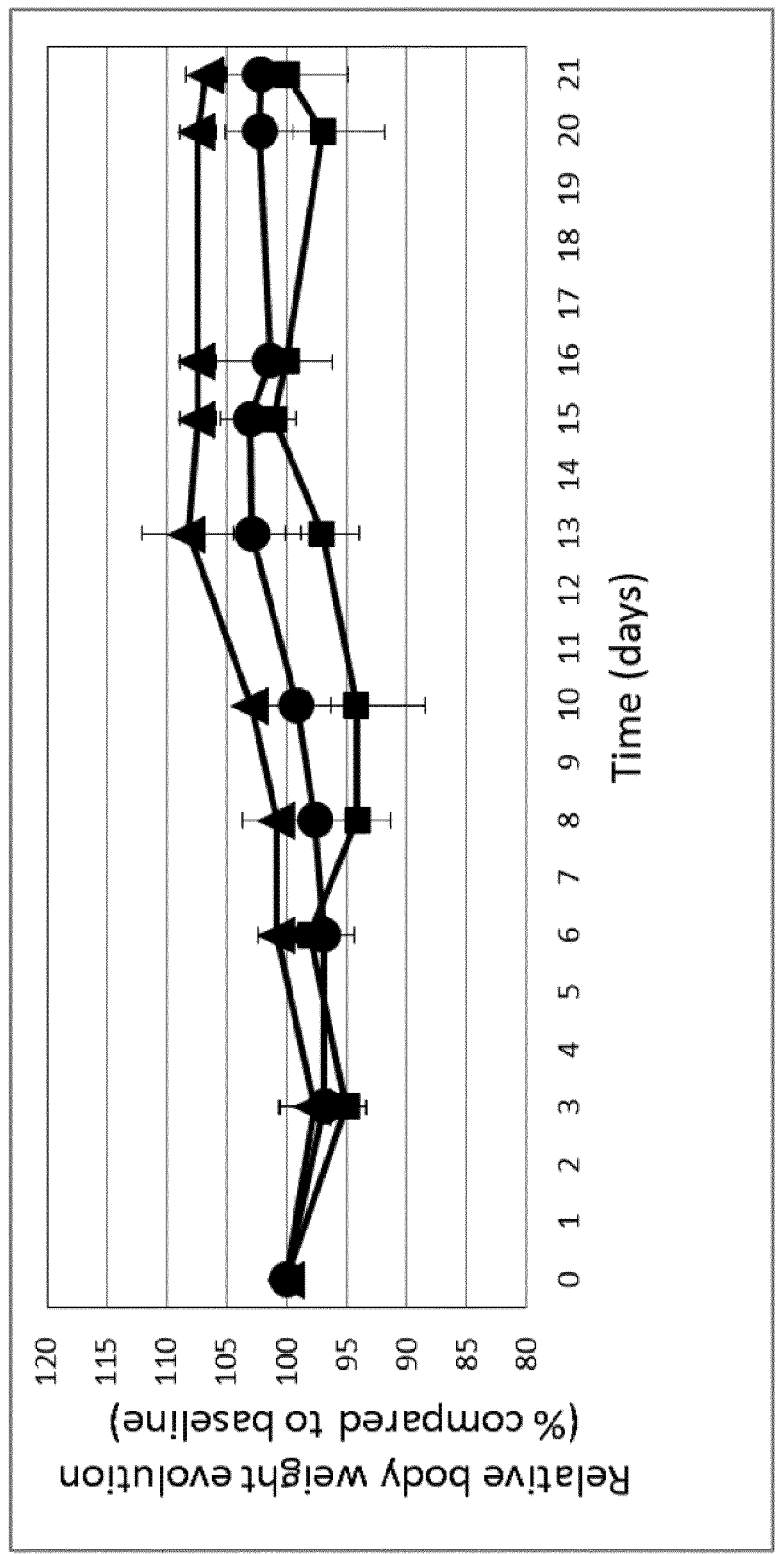

FIG. 17. Relative body weight evolution of the animals of the experiment shown in FIG. 16. Data are presented as the average of the relative body weight of mice in every group±standard deviation. The dashed lines mark the reference values for nu/nu NMRI Mouse strain. PhAc-ALGP-doxorubicin (-■-); Dox (-▲-); and saline (-●-).

Figure 18:
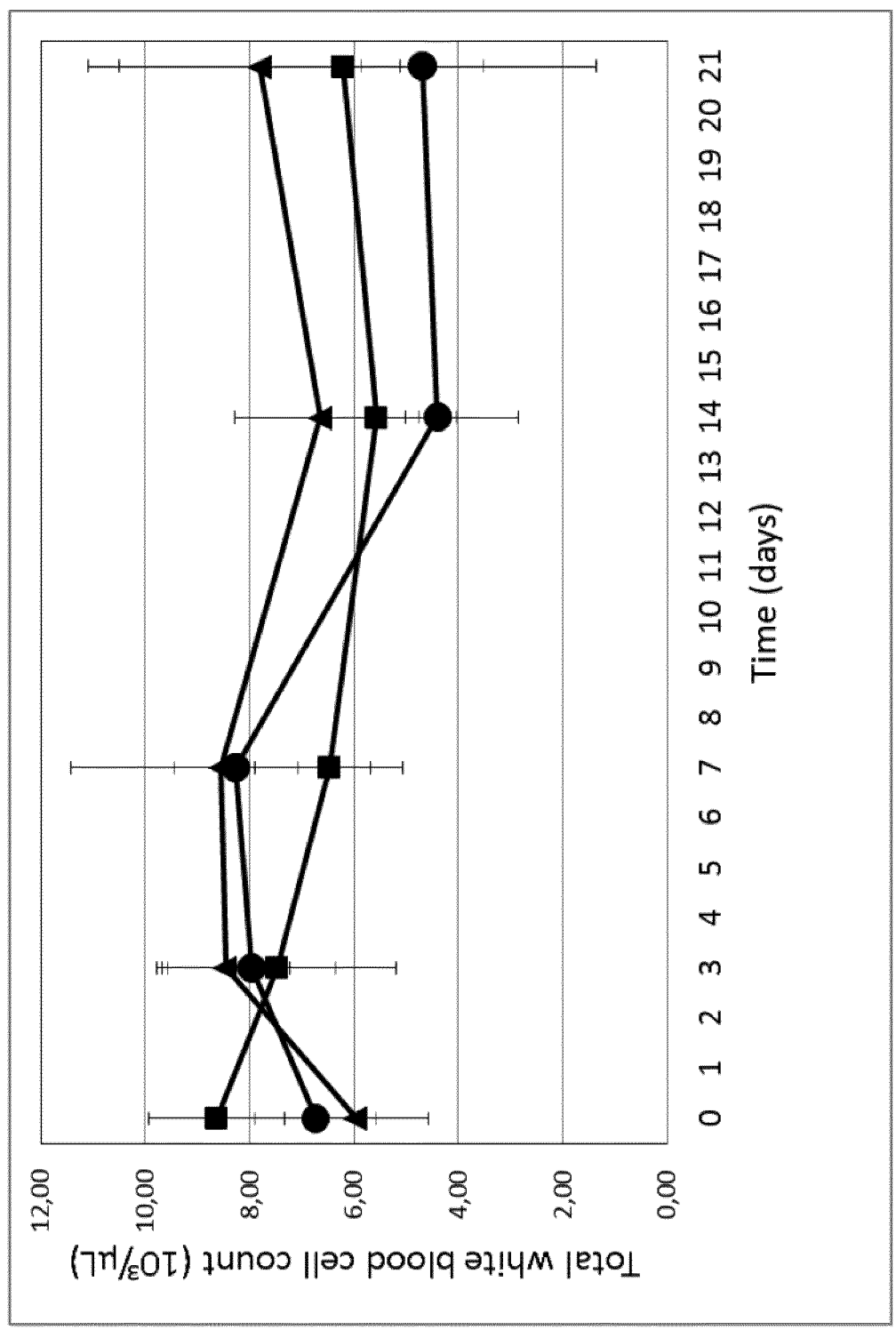

FIG. 18. Total white blood cell count ($10^3$/μL) evolution of the animals of the experiment shown in FIG. 16. Data are presented as the average of the white blood cell count of mice in every group±standard deviation. The dashed lines mark the reference values for nu/nu NMRI mouse strain. PhAc-ALGP-doxorubicin (-■-); Dox (-▲-); and saline (-●-). Total white blood cell count was determined using the CELL-DYN 3500 multiparameter automated hematology analyzer with optimization for murine blood parameters (Abott Diagnostics, Division, Ill., USA)

Figure 19:
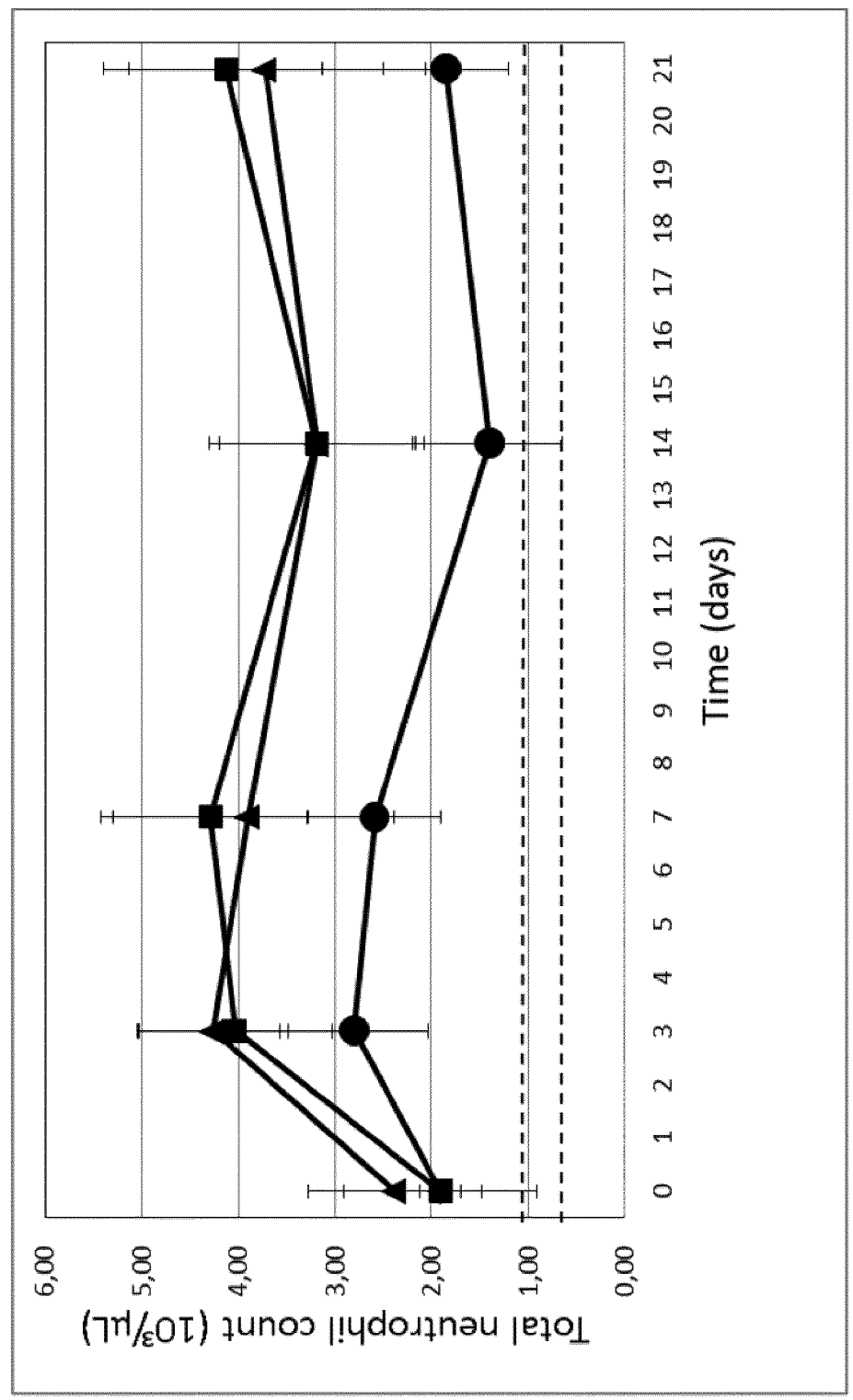

FIG. 19. Total neutrophil count ($10^3$/μL) evolution of the animals of the experiment shown in FIG. 16. Data are presented as the average of the neutrophil count of mice in every group±standard deviation. The dashed lines mark the reference values for nu/nu NMRI mouse strain. PhAc-ALGP-doxorubicin (-■-); Dox (-▲-); and saline (-●-). Neutrophil count was determined using the CELL-DYN 3500 multiparameter automated hematology analyzer with optimization for murine blood parameters (Abott Diagnostics, Division, Ill., USA)

DETAILED DESCRIPTION OF THE INVENTION

In general, the present invention describes new prodrug compounds of therapeutic agents, especially prodrugs comprising an antitumor therapeutic agent, displaying improved therapeutic properties. The improved therapeutic properties include decreased toxicity and increased efficacy. In particular, the prodrugs display a high specificity of action, a reduced toxicity, an improved stability in the serum and blood, and their therapeutic agent is not moving into target cells until the prodrug is finally activated (the activation may involve multiple steps) by (a) target cell associated enzyme(s) such as extracellularly peptidases released from the target cells or such as associated with the extracellular surface of the target cells. Target cells include cancer cells as well as tumor stroma cells. The prodrug compounds of the invention are prodrug forms of a therapeutic agent, in which the therapeutic agent is linked directly or indirectly to an oligopeptide, which in turn, is linked to a stabilizing capping group.

In general, the prodrugs of the invention have the following general structure:

wherein C is a capping group;
OP is an oligopeptidic moiety;
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group, and wherein, if y is greater than 1, the multiple OP moieties are individually linked to each other directly or via a linker or spacing group, with one of the OP moieties being linked directly, via a linker or via a spacing group to D. In other words, multiple OP moieties may be linked together to form a linear or branched structure which is linked to D via one of the OP moieties in the linear or branched structure. Alternatively, the multiple OP moieties are each individually linked to D directly, via a linker, or via a spacing group. An intermediate constellation is included wherein some of the multiple OP moieties are each individually linked to D directly, via a linker, or via a spacing group, and wherein some of the multiple OP moieties are themselves individually linked to each other as described above to form a linear or branched structure of which one of the OP moieties being linked directly, via a linker or via a spacing group to D;
or a pharmaceutically acceptable salt thereof.

For clarification, and without being exhaustive, when y=2 the following prodrugs are included in the general structure: C-OP-D-OP-C; C-OP-OP-D and C-OP-D-OP. The capping group C thus can be present (via direct or indirect linkage as described above) on one or more oligopeptide moieties OP in the case of a prodrug compound/molecule comprising multiple oligopeptide moieties OP.

In one embodiment, the oligopeptidic moiety is a peptide with a minimum length of 4 consecutive amino acids (tetrapeptide) and a maximum length of 8 amino acids (i.e. a peptide with a length of 4, 5, 6, 7 or 8 consecutive amino acids) which comprises a carboxy-terminal proline, wherein said proline is linked directly or via a linker or spacing group to the drug D.

Without being limited thereto, it is our understanding that this oligopeptidic moiety is cleaved/removed from the drug D in a two-step process wherein the first step converts said prodrug to a dipeptide-drug intermediate and wherein the second step converts the dipeptide-drug intermediate to the free drug D. In a particular embodiment the dipeptide remaining in the the dipeptide-drug intermediate has the sequence glycine-proline (GP), alanine-proline (AP), or lysine-proline (KP). It is thus an object of the present invention to provide the produgs with the above-mentioned general formula, wherein OP represents a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP), wherein the proline of said proline comprising dipeptide is linked directly or via a linker or spacing group to the drug D.

In particular, the oligopeptide moiety in the above structure is a tetrapeptide moiety with the sequence Ala-Leu-Gly-Pro (3-letter code), also referred to as ALGP (1-letter code; SEQ ID NO:1); or Ala-Leu-Ala-Leu (3-letter code), also referred to as ALAL (1-letter code; SEQ ID NO:2), and/or the capping group C in the above structure is a phosphonoacetyl group, and/or the drug in the above structure is doxorubicin (hereinafter also referred to as DOX or Dox). Alternatively, the structure of the tetrapeptide is ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10). Accordingly, in one embodiment the structure of the tetrapeptide in the above general structure is selected from the group consisting of ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), and KLKP (SEQ ID NO:10). In particular the tetrapeptide in the above general structure is selected from ALGP (SEQ ID NO:1), or KLGP (SEQ ID NO:6); even more in particular the tetrapeptide in the above general structure is ALGP (1-letter code; SEQ ID NO:1). In a preferred embodiment of the present invention the drug (D) in the above general structure is doxorubicin or a pharmaceutically acceptable salt thereof.

In particular, the prodrug may have the structure of Compound I (see Example 3.1) or may be a pharmaceutically acceptable salt thereof. The capping group phosphonoacetyl provides the advantages of avoiding the use of a non natural amino acids at the terminal end of the oligopeptide. When the drug D is doxorubicin, phosphonoacetyl as capping group C has the further advantage of providing a negatively charge that is important in order to avoid aggregation of oligopeptide derivatives of doxorubicin. In general, the stability of a prodrug of the invention can be defined such that less than 10% of cleavage derivatives are to be obtained upon incubation of the prodrug in human blood for more than 2 hours.

Notwithstanding the above definitions of the capping group C, the oligopeptide moiety OP and the drug, these are not limiting the current invention and other combinations are envisaged by the invention. These combinations include any OP and/or D with the capping group C being a phosphonoacetyl group. Further combinations include any C (any capping group known in the art) and/or any D with the oligopeptide moiety OP being a tetrapeptide moiety with the sequence Ala-Leu-Gly-Pro (3-letter code) or Ala-Leu-Ala-Leu (3-letter code) or ALGP (1-letter code; SEQ ID NO:1) or ALAL (1-letter code; SEQ ID NO:2). Alternatively, the structure of the tetrapeptide is ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10). In a further alternative the structure of the tetrapeptide is ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10). In particular the tetrapeptide in the above general structure is selected from ALGP (SEQ ID NO:1), or KLGP (SEQ ID NO:6); even more in particular the tetrapeptide in the above general structure is ALGP (1-letter code; SEQ ID NO:1).

Depending on the structure/chemical formula of the drug, 1 or more of the oligopeptidic moieties of the invention, of which at least one of them is capped, can be linked to the drug. The oligopeptidic moieties can themselves form a linear or branched structure linked to the drug or, alternatively, multiple oligopeptidic moieties are each individually linked to the drug.

The capping group or protecting or capping moiety is linked to the oligopeptidic moiety of the prodrug and adds to the solubility and/or stability of the prodrug (e.g. in blood of the animal, mammal, human or subject to which the prodrug is administered) and/or adds to the prevention of internalization of the prodrug into a cell such as a target cell.

The linkage between the capping group and the oligopeptide and/or between the oligopeptide and the therapeutic agent or drug may be direct, e.g. via the N-terminal aminogroup of the oligopeptide or the C-terminal carboxylgroup of the oligopeptide, or via a side chain of one of the amino acids of the oligopeptide.

Alternatively, said linkage may be indirect, e.g. by introducing a linker or spacer group between the oligopeptide OP and the drug D. In the case of cytotoxic compounds such as doxorubicin having a free amino ($NH_2$) group, a linker between D and OP is not required per se as enzymatic scission of the amide bond between D and OP ensures the availability of the free $NH_2$-group on the cytoxic drug.

However most of the anticancer cytotoxic drugs D do not have any free $NH_2$-group and cannot as such be linked to OP by an amide bond. Introducing an $NH_2$-group to those molecules may decrease or suppress their cytotoxic activity. For such drugs, a self-immolating (or self-eliminating, self-sacrificing, self-lysing, or self-leaving) spacing group or spacer can be used as linker between the drug D and the oligopeptide OP. OP is linked to the self-immolating spacer by an amide bond sensitive to extracellular enzymes capable of activating the prodrug. After cleavage of the amide bond between OP and the spacer, the self-immolating spacer cleaves itself from the drug leaving it underivatized, i.e., leaving it in its original active form. Self-immolative spacers include para-aminobenzoyloxycarbonyl moieties that are able to connect either —OH, —COOH, —NH, or —SH groups of a drug at the one hand to the carboxy-terminal group of a peptide at the other hand. This type of linker is an electronic cascade spacer. Such bond has been shown to be cleavable by peptidases. After cleavage of the OP-spacer amide bond, the aromatic amine of the self-eliminating spacer becomes electron-donating, which leads to expulsion and release of the free drug and $CO_2$ (Carl et al. 1981, J Med Chem 24, 479-480; Chakravarty et al. 1983, J Med Chem 26, 638-644; de Groot et al. 1999, J Med Chem 42, 5277-5283, King et al. 2002, J Med Chem 45, 4336-4343). Several patents and patent applications describe other self-immolative/self-eliminating spacers, such as heterocyclic ones, releasing a drug from a targeting ligand such as an antibody have been described (e.g. U.S. Pat. No. 6,214,345; US 2003/0130189; US 2003/0096743; U.S. Pat. No. 6,759,509; US 2004/0052793; U.S. Pat. No. 6,218,519; U.S. Pat. No. 6,835,807; U.S. Pat. No. 6,268,488; US 2004/0018194; WO 98/13059; US 2004/0052793; U.S. Pat. No. 6,677,435; U.S. Pat. No. 5,621,002; US 2004/0121940; WO 2004/032828, US 2009/0041791).

Examples of other, not necessarily self-eliminating, linker or spacer groups include aminocaproic acid, a hydrazide group, en ester group, an ether group and a sulphydryl group. A linker or spacer group as described above between the capping group and the oligopeptide and/or between the oligopeptide and the therapeutic agent may be advantageous for reasons such as the following: (i) as a spacer for steric considerations in order to facilitate enzymatic release of the amino acid linked to the therapeutic agent or other enzymatic activation steps; (ii) to provide an appropriate attachment chemistry between the different moieties of the prodrug (and thus providing flexibility to couple any possible drug and/or capping moiety to the oligopeptide of the invention); (iii) to improve the synthetic process of making the prodrug conjugate (e.g., by pre-derivatizing the therapeutic agent or oligopeptide with the linker group before conjugation to enhance yield or specificity); (iv) to improve physical properties of the prodrug; or (v) to provide an additional mechanism for intracellular release of the drug. Whatever the type of linkage, direct or indirect, the linkage should: (1) not or not significantly disturb the functionality of the oligopeptidic moiety, i.e., should not significantly disturb neither the proteolytic scissability by TOP nor the resistance to proteolytic scissability by CD1 and (2) retain the blood stability of the compound. Determination of the functionality of the capped oligopeptidic moiety in the prodrug can be tested easily and in a straightforward way, e.g. as described in the Examples section hereafter. Such testing does not amount to an undue burden for a skilled person.

The phrase "pharmaceutically acceptable salt(s)", as used herein, means those salts of compounds of the invention that are safe and effective for the intended medical use that possess the desired biological activity. Pharmaceutically acceptable salts include salts of acidic or basic groups present in compounds of the invention. Suitable base salts include, but are not limited to, aluminum, calcium, lithium, magnesium, potassium, sodium, zinc, and diethanolamine salts. For a review on pharmaceutically acceptable salts see, e.g., Berge et al. 1977 (J. Pharm. Sci. 66, 1-19) or Handbook of Pharmaceutical Salts: Properties, Selection, and Use (P. H. Stahl, C. G. Wermuth (Eds.), August 2002), incorporated herein by reference.

The drug or therapeutic agent conjugated to the oligopeptide of the invention may be useful for treatment of cancer (e.g. by exerting cytotoxic or antiangiogenic activity), inflammatory disease, or some other medical condition. The drug or therapeutic agent conjugated to the oligopeptide of the invention may be any drug or therapeutic agent capable of entering a target cell. Thus, the therapeutic agent may be selected from a number of classes of compounds including, antibiotics, alkylating agents, antiproliferative agents, tubulin binding agents, *vinca* alkaloids, enediynes, podophyllotoxins or podophyllotoxin derivatives, the pteridine family of drugs, taxanes, anthracyclines, dolastatins, topoisomerase inhibitors, platinum-coordination-complex chemotherapeutic agents, and maytansinoids. More in particular, said drug or therapeutic agent may be one of the following compounds, or a derivative or analog thereof: doxorubicin, daunorubicin, amrubicin, vinblastine, vincristine, calicheamicin, etoposide, etoposide phosphate, CC-1065, duocarmycin, KW 20 2189, methotrexate, methopterin, aminopterin, dichloromethotrexate, docetaxel, paclitaxel, epithiolone, combretastatin, combretastatin A4 phosphate, dolastatin 10. dolastatin 11, dolastatin 15, topotecan, camptothecin, mitomycin C, porfiromycin, 5 fluorouracil, 6-mercaptopurine, fludarabine, tamoxifen, cytosine arabinoside, adenosine arabinoside, colchicine, halichondrin B, cisplatin, carboplatin, mitomycin C, bleomycin, melphalan, chloroquine, cyclosporin A, and maytansine. By derivative is intended a compound that results from reacting the named compound with another chemical moiety (different from the oligopeptidic moiety linked directly or indirectly to the compound), and includes a pharmaceutically acceptable salt, acid, base or ester of the named compound. Other therapeutic agents or drugs include: vindesine, vinorelbine, 10-deacetyltaxol, 7-epi-taxol, baccatin III, 7-xylosyltaxol, isotaxel, ifosfamide, chloroaminophene, procarbazine, chlorambucil, thiophosphoramide, busulfan, dacarbazine (DT1C), geldanamycin, nitroso ureas, estramustine, BCNU, CCNU, fotemustine, streptonigrin, oxaliplatin, methotrexate, aminopterin, raltitrexed, gemcitabine, cladribine, clofarabine, pentostatin, hydroxyureas, irinotecan, topotecan, 9-dimethylaminomethyl-hydroxy-camptothecin hydrochloride, teniposide, amsacrine; mitoxantrone; L-canavanine, THP-adriamycin, idarubicin, rubidazone, pirarubicin, zorubicin, aclarubicin, epiadriamycin (4'epi-adriamycin or epirubicin), mitoxantrone, bleomycins, actinomycins including actinomycin D, streptozotocin, calicheamycin; L-asparaginase; hormones; pure inhibitors of aromatase; androgens, proteasome inhibitors; farnesyl-transferase inhibitors (FTI); epothilones; discodermolide; fostriecin; inhibitors of tyrosine kinases such as STI 571 (imatinib mesylate); receptor tyrosine kinase inhibitors such as erlotinib, sorafenib, vandetanib, canertinib, PKI 166, gefitinib, sunitinib, lapatinib, EKB-569; Bcr-Abl kinase inhibitors such as dasatinib, nilotinib, imatinib; aurora kinase inhibitors such as VX-680, CYC116, PHA-739358, SU-6668, JNJ-7706621, MLN8054, AZD-1152, PHA-680632; CDK inhibitors such as flavopirodol, seliciclib, E7070, BMS-387032; MEK inhibitors such as PD184352, U-0126; mTOR inhibitors such as CCI-779 or AP23573; kinesin spindle inhibitors such as ispinesib or MK-0731; RAF/MEK inhibitors such as Sorafenib, CHIR-265, PLX-4032, CI-1040, PD0325901 or ARRY-142886; bryostatin; L-779450; LY333531; endostatins; the HSP 90 binding agent geldanamycin, macrocyclic polyethers such as halichondrin B, eribulin. For a number of compounds included in the above listing, more experimental guidance is given in Example 16 herein. Amongst the drugs other than doxorubicin covered in this invention is amrubicin which is an anthracycline analogue with a free $NH_2$- group (Hanada et al. 1998, Jpn J Cancer Res 89, 1229-1238) that can be linked to a capped oligopeptide such as PhAc-ALGP by the same method as used for doxorubicin. Addition of (a) polyethylene glycol group(s) to the amino- of the oligopeptidic moiety) may be performed in order to increase the half-life of the prodrug according to the invention in circulation after administration to a mammal. Addition of (a) polyethylene glycol group(s) could also play the role of a capping agent.

A prodrug or salt thereof of the invention can further be present in a composition comprising besides the prodrug or salt thereof any one of a suitable solvent (capable of solubilizing the prodrug to the desired extent), diluent (capable of diluting concentrated prodrug to the desired extent) or carrier (any compound capable of absorbing, adhering or incorporating the prodrug, and of subsequently releasing at any rate the prodrug in the extracellular compartment of the subject's body). Said composition may alternatively comprise multiple (i.e. more than 1) prodrug or salt thereof, or any combination thereof (e.g. prodrug 1+its salt, prodrug 1+prodrug 2, prodrug 1+its salt+prodrug 2, etc.) In particular, said solvent, diluents or carrier is pharmaceutically acceptable, i.e., is acceptable to be administered to a subject to be treated with the composition of the invention. Aiding in formulating a pharmaceutically acceptable composition is e.g. any Pharmacopeia book. The composition may be formulated such that it is suitable for any way of administration including intra-cranial, intra-spinal, enteral and parenteral administration. The regimen by which the prodrug is administered may vary, e.g. depending on whether or not a capping group is present, depending on the formulation, depending on the overall physical condition of a subject to be treated and e.g. depending on the judgment of the treating physician.

The prodrug or salt thereof of the invention, or a composition comprising it, is particularly suitable for treating a disease that is treatable by the released drug. Of particular interest is cancer or tumors such as solid tumors. "Cancer" includes e.g. breast cancers, colorectal cancers, liver cancers, lung cancers such as small cell, non-small cell, bronchic cancers, prostate cancers, ovarian cancers, brain cancers, and pancreatic cancers, colon cancers, head and neck cancers, stomach cancers, bladder cancers, non-Hodgkin's lymphomas, melanomas, leukaemias, neuroblastomas, and glioblastomas. The subject to be treated with the prodrug of the invention can be any mammal in need of such treatment but is in particular a human. The treatment can result in regression of the disease (e.g. in terms of decreasing tumor volume or tumor mass and of metastases), in decreased progression of the disease compared to expected disease progression, or in stabilization of the disease, i.e. neither regression nor progression of the disease. All these are favorable outcomes of the treatment. In particular, the effective amounts of said prodrug or salt thereof, or of said composition is not causing severe leukopenia or cardiac toxicity/cardiotoxicity. A possible definition of severe human leukopenia is WHO-criteria-defined grade 3-(1000-1900 leukocytes/mL) or grade 4-leukopenia (less than 1000 leukocytes/mL).

Inclusion of an anticancer prodrug (or a salt thereof) according to the present invention in combination therapies is also envisaged. This can be in a combined modality chemotherapy, i.e. the use of the anticancer prodrug (or a salt thereof) with other cancer treatments, such as radiation therapy (whether by direct irradiation or via administering an isotope-labeled antibody or antibody fragment) or surgery. This can also be in combination chemotherapy, i.e. treating a patient with a number of different drugs wherein the drugs preferably differ in their mechanism of action and in their side effects. Usually in such combination chemotherapy the drugs are administered simultaneously. An advantage of combination chemotherapy is the minimization of the chance of the development of resistance to any one agent. A further advantage may be that the individual drugs can each be used at a lower dose, thereby reducing overall toxicity.

A prodrug or salt thereof according to the invention, or a composition comprising such prodrug or salt, can thus be used for treatment of a disease (e.g. cancer), as monotherapy, or as part of a combination chemotherapy treatment or a combined modality chemotherapy treatment.

More in general in relation to combination chemotherapy, an anticancer prodrug (or a salt thereof) according to the invention can be combined with one or more alkylating antineoplastic agent(s) and/or one or more anti-metabolite(s) and/or one or more anti-microtubule agent(s) and/or one or more topoisomerase inhibitor(s) and/or one or more cytotoxic antibiotic(s) and/or one or more biological anticancer agent(s) (such as antibodies), wherein one or more of these, when applicable, can also be prodrug(s) (or a salt thereof) according to the present invention.

The drug doxorubicin (also known under the trade names Adriamycin or Rubex) is commonly used to treat multiple types of cancers such as some leukemias and Hodgkin's lymphoma, as well as cancers of the bladder, breast, stomach, lung, ovaries, thyroid, soft tissue sarcoma, multiple myeloma, and others. Doxorubicin is further used in different combination therapies. Doxorubicin-containing therapies include AC or CA (Adriamycin, cyclophosphamide), TAC (Taxotere, AC), ABVD (Adriamycin, bleomycin, vinblastine, dacarbazine), BEACOPP (bleomycin, etoposide, Adriamycin (doxorubicin), cyclophosphamide, Oncovin (vincristine), procarbazine, prednisone), CHOP (cyclophosphamide, Adriamycin, vincristine, prednisolone), FAC or CAF (5-fluorouracil, Adriamycin, cyclophosphamide), MVAC (methothrexate, vincristine, adriamycin, cisplatin), CAV (cyclophosphamide, doxorubicin, vincristine) and CAVE (CAV, etoposide), CVAD (cyclophosphamide, vincristine, adriamycin, dexamethasone), DT-PACE (dexamethasone, thalidomide, cisplatin or platinol, adriamycin, cyclophosphamide, etoposide), m-BACOD (methothrexate, bleomycin, adriamycin, cyclophosphamide, vincristine, dexamethasone), MACOP-B (methothrexate, leucovorin, adriamycin, cyclophosphamide, vincristine, prednisone, bleomycin), Pro-MACE-MOPP (methothrexate, adriamycin, cyclophosphamide, etoposide, mechlorethamine, vincristine, procarbazine, prednisone), ProMACE-CytaBOM (prednisone, doxorubicin, cyclophosphamide, etoposide, cytarabine, bleomycin, vincristine, methothrexate, leucovorin), Stanford V (doxorubicin, mechlorethamine, bleomycin, vinblastine, vincristine, etoposide, prednisone), DD-4A (vincristine, actinomycin, doxorubicin), VAD (vincristine, doxorubicin, dexamethasone), Regimen I (vincristine, doxorubicin, etoposide, cyclophosphamide) and VAPEC-B (vincristine, doxorubicin, prednisone, etoposide, cyclophosphamide, bleomycin). Besides the doxorubicin-comprising combination chemotherapies there is a plethora of other combination chemotherapies such as BEP (Bleomycin, etoposide, platinum agent (cisplatin (Platinol))), CAPDX or XELOX (capecitabine, oxaliplatin), CBV (cyclophosphamide, carmustine, etoposide), FOLFIRI (fluorouracil, leucovorin, irinotecan), FOLFIRINOX (fluorouracil, leucovorin, irinotecan, oxaliplatin), FOLFOX (fluorouracil, leucovorin, oxaliplatin), EC (epirubicin, cyclophosphamide), ICE (ifosfamide, carboplatin, etoposide (VP-16)) and IFL (irinotecan, leucovorin, fluorouracil). Combination of doxorubicin with sirolimus (rapamycin) has been disclosed by Wendel et al. 2004 (Nature 428, 332-337) in treatment of Akt-positive lymphomas in mice. In any of these combination therapies any of the drugs could be substituted by a prodrug (or a salt thereof) according to the present invention.

One can further also envisage combination therapies including an anticancer prodrug (or a salt thereof) according to the invention (whether alone or already part of a combination chemotherapy or of a combined modality therapy) and compounds other than cytostatics. Such other compounds include any compound approved for treating cancer or being developed for treating cancer. In particular, such other compounds include monoclonal antibodies such as alemtuzumab (chronic lymphocytic leukemia), bevacizumab (colorectal cancer), cetuximab (colorectal cancer, head and neck cancer), denosumab (solid tumor's bony metastases), gemtuzumab (acute myelogenous leukemia), ipilimumab (melanoma), ofatumumab (chronic lymphocytic leukemia), panitumumab (colorectal cancer), rituximab (Non-Hodgkin lymphoma), tositumomab (Non-Hodgkin lymphoma) and trastuzumab (breast cancer). Other antibodies include for instance abagovomab (ovarian cancer), adecatumumab (prostate and breast cancer), afutuzumab (lymphoma), amatuximab, apolizumab (hematological cancers), blinatumomab, cixutumumab (solid tumors), dacetuzumab (hematologic cancers), elotuzumab (multiple myeloma), farletuzumab (ovarian cancer), intetumumab (solid tumors), Matuzumab (colorectal, lung and stomach cancer), onartuzumab, parsatuzumab, pritumumab (brain cancer), tremelimumab, ublituximab, veltuzumab (non-Hodgkin's lymphoma), votumumab (colorectal tumors), zatuximab and anti-placental growth factor antibodies such as described in WO 2006/099698. Examples of such combination therapies include for instance CHOP-R (CHOP (see above)+rituximab), ICE-R (ICE (see above)+rituximab), R-FCM (rituximab, fludarabine, cyclophosphamide, mitoxantrone) and TCH (Paclitaxel (Taxol), carboplatin, trastuzumab).

Examples of alkylating antineoplastic agents include nitrogen mustards (for example mechlorethamine, cyclophosphamide, melphalan, chlorambucil, ifosfamide and busulfan), nitrosoureas (for example N-Nitroso-N-methylurea (MNU), carmustine (BCNU), lomustine (CCNU), semustine (MeCCNU), fotemustine and streptozotocin), tetrazines (for example dacarbazine, mitozolomide and temozolomide), aziridines (for example thiotepa, mytomycin and diaziquone (AZQ)), cisplatins and derivatives (for example cisplatin, carboplatin and oxaliplatin), and non-classical alkylating agents (for example procarbazine and hexamethylmelamine)

Subtypes of the anti-metabolites include the anti-folates (for example methotrexate and pemetrexed), fluoropyrimidines (for example fluorouracil, capecitabine and tegafur/uracil), deoxynucleoside analogues (for example cytarabine, gemcitabine, decitabine, Vidaza, fludarabine, nelarabine, cladribine, clofarabine and pentostatin) and thiopurines (for example thioguanine and mercaptopurine).

Anti-microtubule agents include the *vinca* alkaloid subtypes (for example vincristine, vinblastine, vinorelbine, vindesine and vinflunine) and taxane subtypes (for example paclitaxel and docetaxel). Other anti-microtubule agents include podophyllotoxin.

Topoisomerase inhibitors include topoisomerase I inhibitors (for example irinotecan, topotecan and camptothecin) and topoisomerase II inhibitors (for example etoposide, doxorubicin, mitoxantrone, teniposide, novobiocin, merbarone, and aclarubicin).

Cytotoxic antibiotics include anthracyclines (doxorubicin, daunorubicin, epirubicin, idarubicin, pirarubicin, aclarubicin and mitoxantrone) and other drugs including actinomycin, bleomycin, plicamycin and mitomycin.

Any anticancer prodrug (or a salt thereof) according to the invention can (whether alone or already part of a combination chemotherapy or of a combined modality therapy) further be included in an antibody-directed enzyme prodrug therapy (ADEPT), which includes the application of cancer-associated monoclonal antibodies, which are linked, to a drug-activating enzyme. Subsequent systemic administration of a non-toxic agent results in its conversion to a toxic drug, and resulting in a cytotoxic effect which can be targeted at malignant cells (Bagshawe et al. (1995) Tumor Targeting 1, 17-29.)

Further, any anticancer prodrug (or a salt thereof) according to the invention can (whether alone or already part of a combination chemotherapy or of a combined modality therapy) be combined with one or more agent(s) capable of reversing (multi)drug resistance ((M)DR reverser(s) or (M)DR reversing agent(s)) that can occur during chemotherapy. Such agents include for example loperamide (Zhou et al. 2011, Cancer Invest 30, 119-125). Another such combination includes loading the prodrug in nanoparticles such as iron oxide nanoparticles (Kievit et al. 2011, J Control Release 152, 76-83) or liposomes. Examples of drugs loaded into liposomes include doxorubicin (doxorubicin HCL liposomes, also known under the trade names Doxil, Caelyx or Myocet), daunorubicin (known under the trade name DaunoXome) and paclitaxel (Garcion et al. 2006, Mol Cancer Ther 5, 1710-1722).

A prodrug or salt thereof according to the invention, or a composition comprising such prodrug or salt, can thus be used for treatment of a disease (e.g. cancer), as monotherapy, or as part of a combination chemotherapy treatment or a combined modality chemotherapy treatment. Any of such treatments can further be combined with a treatment including a drug resistance reverting agent.

The invention further relates to methods of producing the prodrugs of the invention, said methods comprising the steps of:

(i) obtaining the drug;
(ii) linking the drug to a phosphonoacetyl-capped oligopeptidic moiety, resulting in the prodrug; or, alternatively,
(ii') linking the drug to an oligopeptidic moiety followed by linking the phosphonoacetyl capping group to the oligopeptidic moiety, resulting in the prodrug; and
(iii) purifying the prodrug obtained in step (ii) or (ii').

As described above, said linking of the oligopeptidic moiety with the drug and/or capping group may be direct, or indirect via a linker or spacing group, such as a self-immolating or self-eliminating spacer. The purification strategy of the prodrug will obviously depend on the nature of the drug and/or of the capping group. A skilled person will be able to design a suitable purification strategy for any possible prodrug according to the invention, choosing from a plethora of purification techniques that are available.

Without being bound by any theory or explanation, the picture emerging from the Examples as described herein is one that, for the exemplary prodrug of the invention comprising the ALGP-peptide (SEQ ID NO:1) as OP moiety and doxorubicin as the drug D, the activation of the prodrug is occurring in multiple steps. Whereas such prodrug is stable in blood and plasma, it is converted in a mixture of doxorubicin (Dox), GP-Dox and LGP-Dox when incubated in the presence of LS-174T tumor cells. The latter process can in a first step be mimicked in vitro by proteases such as CD10 (yielding LGP-Dox that can be converted to GP-Dox by common leucine aminopeptidases) and TOP (yielding GP-Dox). The first phase of the activation of the ALGP-doxorubicin is driven by the preferential activity of CD10 and TOP in the vicinity of the tumors compared to their lower abundancy in non-pathological extracellular compartments and tissues. The second step, conversion of GP-Dox to Dox, can be driven by dipeptidyl prolyl peptidases. Two members of this class are of interest in the area of cancer: DPIV, also known as CD26 and FAP or fibroblast activation protein. All these proteases are known to be associated with tumor cells or tumor stromal cells as described hereafter. Such multistep activation of a prodrug of the invention increases the specificity and decreases the unwanted side effects (such as leucopenia and cardiac toxicity) compared to similar prodrugs that are activatable in a single step. An example of the latter is succinyl-βALAL-doxorubicin which is easily converted by e.g. CD10 to L-Dox that can enter the cell on its own (Pan et al. 2003, Cancer Res 63, 5526-5531). The multiple activation steps approach yielded a PhAc-ALGP-doxorubicin prodrug that is about 20 to 40 times less toxic than doxorubicin varying with the mode (IV or IP) of administration, and between 6 and 14 times less toxic than succinyl-β-ALAL-doxorubicin. PhAc-ALGP-doxorubicin is devoid of chronic cumulative cardiotoxicity and does not induce leucopenia and lymphopenia. It is more active than doxorubicin on human tumor xenografts (including a sarcoma) and on an orthotopic colon carcinoma. The prodrugs of the invention therefore are further characterized by being activatable, in vitro or in vivo, in at least two steps, i.e., in a process involving at least two essential proteolytic cleavages by at least two different proteases. An "essential proteolytic cleavage" is herein meant to be a cleavage that is associated with a tumor or a tumor-associated cell such as its stroma, i.e., is specifically occurring in the direct vicinity of a tumor or tumor-associated cells.

Endopeptidases CD10 and TOP

CD10 is a neutral endopeptidase/a zinc dependent cell surface metallopeptidase that cleaves small peptides on the amino-side of hydrophobic amino acids. Besides being present on normal cells such as B cells and epithelial cells of the lung, colon and kidney, it is present in many tumor types (Ravel et al. 2008, Clin Cancer Res 14, 1258-1265), such as pancreatic cancer (Notohara et al. 2000, Am J Surg Pathol 24, 1361-1371), hepatocellular carcinoma (Karabork et al. 2010, Pathol Res Pract 206, 572-577), melanoma (Velazquez et al. 2007, J Transl Med 5, 2), prostate cancer (Song et al. 2004, Prostate 58, 394-405), lung small cell carcinomas (Shipp et al. 1991, Proc Natl Acad Sci USA 88, 10662-10666), renal carcinoma, endometrial sarcoma and rhabdomyosarcoma (Chu et al. 2000, Am J Clin Pathol 113, 374-382). CD10 is expressed in nearly half of the soft tissue sarcomas (histiocytomas, fibrosarcomas, rhabdomyosarcomas, leiomyosarcomas, liposarcomas, malignant peripheral nerve sheat tumors; Deniz et al. 2012, Pathol Res Pract 208, 281-285). Even more interesting and similar to the stromal distribution of FAP, CD10 is found in the stromal cells of colorectal carcinomas (Hirano et al. 2012, Pathol Int 62, 600-611), breast cancer (Desmedt et al. 2012, Clin Cancer Res 18, 1004-1014; Marketsov et al. 20, 84-89), pancreatic endocrine tumors (Deschamps et al. 2006, Hum Path 37, 802-808), gastric carcinoma (Huang et al. 2005, Jpn J Clin Oncol 35, 245-250) and basal cell carcinoma (Yada et al. 2004, Am J Dermatopathol 26, 463-473).

TOP (Thimet Oligo Peptidase) is a thiol-dependent main cytoplasmic metallo-endoprotease distributed throughout many tissues and cell types. It can attain an extracellular location both via secretion of the soluble enzyme and by attachment to the plasma membrane. It is distributed throughout many tissues and cell types. TOP is involved in neuroendocrine signaling and in the extracellular metabolism of neuropeptides (Corie et al. 2002, Endocrine Rev 23, 647-664). It is involved in the metabolism of proteasomes (Saric et al. 2004, J Biol Chem 45, 46723-46732). TOP is involved in neuropeptide processing in prostate and prostate cancer (Swanson et al. 2004, Protein Pept Lett 5, 471-478) and is found in tumor cell conditioned media. It can be released from damaged or necrotic cells. Its activity is reduced in oxygenated media and enhanced in anoxic environments that are very often characteristic of solid tumors. TOP is expressed at the surface of endothelial cells and plays a role in vasoactive peptide metabolism (Norman et al. 2003, Am J Physiol Heart Circ Physiol 284, H1978-1984; Shivakumar et al. 2005, Cell Biochem Funct 23, 195-204). Top is detected by immunostaining in 113 out of 147 breast carcinoma in both tumoral and stromal cells. It is expressed in both carcinoma and stromal cells in 88 prostate carcinoma biopsies out of 98 (Ravel et al. 2008, Clin Cancer Res 14, 1258-1265). TOP is responsible for the extracellular activation of succinyl-β-ALAL-doxorubicin and PhAc-ALGP-doxorubicin (Dubois et al. 2006, Eur J Cancer 17, 3049-3056).

Dipeptidyl Prolyl Peptidases DPIV (CD26) and FAP

DPIV is a dipeptidylprolylpeptidase with a broad spectrum of activity and covers a large number of physiological substrates. It is expressed in epithelial cells of a large number of organs. It is expressed in thymus spleen and lymph nodes as well as lymphocytes. DPIV binds to collagen and fibronectin in experimental conditions (Loster et al. 1995, Biochem Biophys Res Commun 217, 341). It is upregulated in the tumoral T-cell malignancies (Dang et al. 2002, Histol Histopathol 17, 1213-1226) and in different adenocarcinomas, such as in hepatocellular carcinoma (Stecca et al. 1997, J Hepatol 27, 997-945), thyroid carcinoma (Tanaka et al. 1995, Int J Cancer 64, 326-331), in meningiomas (Yu et al. 2010, FEBS Journal 277, 1126-1144; Stremenoova et al. 2010, Int J Oncology 36, 351-358), in esophageal adenocarcinomas (Goscinski et al. 2008, APMIS 116, 823-831), in lung adenocarcinomas (Asada et al. 1993, Histopathology 23, 265-270) and in bone and soft tissue tumors (Dohi et al. 2009, Histopathology 4, 432-440). DPIV is expressed in cancer stem cells of human colorectal cancer and of human mesotheliomas (Pang et al. 2010, Cell Stem Cell 6, 603-615; Yamazaki et al. 2012, Biochem Biophys Res Commun 419, 529-536).

FAP is a dipeptidyl exopeptidase with very narrow specificity restricted to glycine-proline, alanine-proline and lysine-proline dipeptides and is also a type I collagenase. It can however also act as endopeptidase (Siew lai et al. 2007, Bioconj Chem 18, 1245-1250). FAP is absent in normal adult tissues such as epithelial, mesenchymal; neural and lymphoid cells such as lymphocytes. It is absent in non-malignant tumors. More importantly it is upregulated, not in the tumoral cells themselves, but in the reactive fibroblast, stromal and angiogenic cells present in epithelial and sarcoma tumors with the exception of the Ewing sarcoma (Yu et al. 2010, FEBS Journal 277, 1126-1144; Brennen et al. 2012, Mol Cancer Ther 11, 257-269). It plays an important role in colon cancer (Leonard et al. 2007, Clin Cancer Res 13, 1736-1741), melanoma (Fazakas et al. 2011, PLoS one 6, e20758; Artym et al. 2002, Carcinogenesis 23, 1593-1601), pancreatic cancer (Hyung-Ok et al. 2011, BMC Cancer 11, 245; Min et al. 2012, World J Gastroenterol 28, 840-846), gastric cancer (Zhi et al. 2010, J Exp Clin Cancer Res 29, 66; Mori et al. 2004, Oncology 67, 411-419), non-small lung cancer (Bremnes et al. 2011, J Thorac Oncol 1, 209-217), glioma (Menlein 2011, Biol Chem 392, 199-207), skin cancers (Huber et al. 2006, J Cut Pathol 2, 145-155), cervical carcinoma (Jin et al. 2003, Anticancer Res 4, 195-0198), thyroid carcinoma (Nocolini et al. 2011, Biochem Pharmacol 7, 778-780), rectal carcinoma (Saaigusa et al. 2011, Int J Oncol 3, 655-663), esophageal carcinoma (Goscinski et al. 2008, Ultrastruct Pathol 3, 89-96), in breast cancer (Huang et al. 2011, Clin Exp Metastasis 6, 567-579), and in bone and soft tissue tumors (Dohi et al. 2009, Histopathology 4, 432-440). The reactive stromal cells of tumors cells are essential for the growth of the tumoral cells as well as for their invasive and angiogenic capacities (Santos et al. 2009, J Clin Invest 119, 3613-3625; Cheng et al. 2002, Cancer Res 62, 4767-4772; Huang et al. 2004, Cancer Res 64, 2712-2716).

Based on the Examples (see, e.g. Example 16), several methods of screening for candidate prodrugs according to the invention can be envisaged. Such methods include methods of screening candidate prodrugs having the general structure

wherein C is a capping group;
OP is a peptide with a minimum length of 4 consecutive amino acids (tetrapeptide) and a maximum length of 8 amino acids (i.e. a peptide with a length of 4, 5, 6, 7 or 8 consecutive amino acids), which comprises carboxy-terminally a proline comprising dipeptide selected from the group consisting of glycine-proline (GP), alanine-proline (AP), and lysine-proline (KP);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacer group such as a self-immolating or self-eliminating spacer group, and wherein, if y is greater than 1, the multiple OP moieties are individually linked to each other directly or via a linker or spacing group and/or are individually linked to D directly or via a linker or spacing group; and
wherein said screening method is comprising the steps of:
(i) obtaining the drug D;
(ii) conjugating the drug D to a GP-, AP- or KP-dipeptide to obtain a GP-D, AP-D or KP-D as dipeptide-drug intermediate prodrug;
(iii) contacting each of drug D and said dipeptide-drug intermediate prodrug GP-D, AP-D or KP-D independently with in vitro cultured cells;
(iv) determining the cytotoxicity of drug D and dipeptide-drug intermediate prodrug GP-D, AP-D or KP-D;
(v) identifying from (iv) a dipeptide-drug intermediate prodrug GP-D, AP-D or KP-D with comparable cytotoxic activity as drug D; and
(vi) selecting $[C_x\text{-}OP]_y\text{-}D$ corresponding to dipeptide-drug intermediate prodrug GP-D, AP-D or KP-D identified in step (v) as candidate prodrug.

In the above method, the term "corresponding to" is to be understood such that the selected candidate prodrug $[C_x\text{-}OP]_y\text{-}D$ is comprising the same drug D as present in the dipeptide-drug intermediate prodrug GP-D, AP-D or KP-D identified to have comparable cytotoxic activity as drug D. Optionally, the drug D is connected to the oligopeptide moiety OP in the same was as it is connected to the GP-, AP- or KP-dipeptide in the dipeptide-drug intermediate prodrug GP-D, AP-D or KP-D. In other words, the success of the in step (v) identified dipeptide-drug intermediate prodrug GP-D, AP-D or KP-D is indicative or predictive for the success of the candidate prodrug $[C_x\text{-}OP]_y\text{-}D$ wherein OP represents a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP). Such extrapolation is plausible in view of the extensive results described herein as obtained with doxorubicin as drug D. When a dipeptide-drug intermediate prodrug GP-D, AP-D or KP-D has a cytotoxic activity comparable to the cytotoxic activity of drug D, this is a good indication of the successful activation of such prodrug to the free drug D by the cultured cells. The cultured cells used in this type of screening may for instance be a cultured tumor cell line.

In a particular embodiment the peptide OP in the above mentioned general structure is a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10). Thus in said embodiment the present invention provides methods of screening candidate prodrugs having the general structure $[C_x\text{-}OP]_y\text{-}D,$ wherein C is a capping group;
OP is a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacer group such as a self-immolating or self-eliminating spacer group, and wherein, if y is greater than 1, the multiple OP moieties are individually linked to each other directly or via a linker or spacing group and/or are individually linked to D directly or via a linker or spacing group; and
wherein said screening method is comprising the steps of:
(i) obtaining the drug D;
(ii) conjugating the drug D to a GP-, AP- or KP-dipeptide to obtain a GP-D, AP-D or KP-D as dipeptide-drug intermediate prodrug;
(iii) contacting each of drug D and said dipeptide-drug intermediate prodrug GP-D, AP-D or KP-D independently with in vitro cultured cells;
(iv) determining the cytotoxicity of drug D and dipeptide-drug intermediate prodrug GP-D, AP-D or KP-D;
(v) identifying from (iv) a dipeptide-drug intermediate prodrug GP-D, AP-D or KP-D with comparable cytotoxic activity as drug D; and
(vi) selecting $[C_x\text{-}OP]_y\text{-}D$ corresponding to dipeptide-drug intermediate prodrug GP-D, AP-D or KP-D identified in step (v) as candidate prodrug.

Alternatively, said methods are methods of screening candidate prodrugs having the general structure $[C_x\text{-}OP]_y\text{-}D,$ wherein C is a capping group;
OP is a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group such as a self-immolating or self-eliminating spacer, and wherein, if y is greater than 1, the multiple OP moieties are individually linked to each other directly or via a linker or spacing group and/or are individually linked to D directly or via a linker or spacing group;
wherein said method is comprising the steps of:
(i) obtaining the drug D;
(ii) conjugating the drug D to $[C_x\text{-}OP]_y$ to obtain a $[C_x\text{-}OP]_y\text{-}D$ prodrug;
(iii) contacting each of drug D and prodrug $[C_x\text{-}OP]_y\text{-}D$ independently with in vitro cultured cells;
(iv) determining the cytotoxicity of drug D and prodrug $[C_x\text{-}OP]_y\text{-}D$;
(v) identifying from (iv) a prodrug $[C_x\text{-}OP]_y\text{-}D$ with comparable cytotoxic activity as drug D; and
(vi) selecting $[C_x\text{-}OP]_y\text{-}D$ identified in step (v) as candidate prodrug.

In the above mentioned screening methods, the term "comparable cytotoxic activity" is to be understood such that a prodrug, after contact with the in vitro cultured cells (such as cultured tumor cells), exerts at least 50% or at least between 50 and 99% (e.g., at least 55%, at least 60%, at least 65%, at least 70%, at least 75%, at least 80%, at least 55%, at least 90%, at least 95%, at least 99%) of the cytotoxic activity exerted by the free drug contacted with the same in vitro cultured cells under the same conditions.

In another alternative, said methods are methods of screening candidate prodrugs having the general structure $[C_x\text{-}OP]_y\text{-}D,$ wherein C is a capping group;
OP is a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); in particular OP is the tetrapeptide ALGP (SEQ ID NO:1);
D is a drug;
x is an integer being at least 1 when y=1;
y is an integer being at least 1, if y is greater than 1, then at least 1 OP is carrying a capping group; and
wherein the linkage between C and OP and the linkage between OP and D is direct or via a linker or spacing group such as a self-immolating or self-eliminating spacer, and wherein, if y is greater than 1, the multiple OP moieties are individually linked to each other directly or via a linker or spacing group and/or are individually linked to D directly or via a linker or spacing group;
wherein said method is comprising the steps of:
(i) obtaining the drug D;
(ii) conjugating the drug D to $[C_x\text{-}OP]_y$ to obtain a $[C_x\text{-}OP]_y\text{-}D$ prodrug;
(iii) contacting prodrug $[C_x\text{-}OP]_y\text{-}D$ for 5 h at 37° C. with in vitro cultured cells;
(iv) determining the conversion of prodrug $[C_x\text{-}OP]_y\text{-}D$ into free drug D;
(v) identifying from (iv) a prodrug $[C_x\text{-}OP]_y\text{-}D$ which is converted by at least 50% to D; and
(vi) selecting $[C_x\text{-}OP]_y\text{-}D$ identified in step (v) as candidate prodrug.

In yet another alternative, said methods are methods of screening candidate prodrugs having the general structure $[C_x\text{-}OP]_y\text{-}D,$ wherein C is a capping group;

OP is a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); in particular OP is the tetrapeptide ALGP (SEQ ID NO:1);

D is a drug;

x is an integer being at least 1 when y=1;

y is an integer being at least 1, if y is greater than 1, then at least 1 OP is carrying a capping group; and wherein the linkage between C and OP and the linkage between OP and D is direct or via a linker or spacing group such as a self-immolating or self-eliminating spacer, and wherein, if y is greater than 1, the multiple OP moieties are individually linked to each other directly or via a linker or spacing group and/or are individually linked to D directly or via a linker or spacing group;

wherein said method is comprising the steps of:

(i) obtaining the drug D;

(ii) conjugating the drug D to a GP-, AP- or KP-dipeptide to obtain a GP-D, AP-D or KP-D dipeptide-drug intermediate prodrug;

(iii) contacting dipeptide-drug intermediate prodrug GP-D for 3 h at 37° C. with isolated FAP and/or DPIV peptidases;

(iv) determining the conversion of dipeptide-drug intermediate prodrug GP-D, AP-D or KP-D into free drug D;

(v) identifying from (iv) a dipeptide-drug intermediate prodrug GP-D, AP-D or KP-D which is converted by at least 50% to D; and (vi) selecting $[C_x\text{-OP}]_y$-D corresponding to dipeptide-drug intermediate prodrug GP-D, AP-D or KP-D identified in step (v) as candidate prodrug.

In the above method, the term "corresponding to" is to be understood such that the selected candidate prodrug $[C_x\text{-OP}]_y$-D is comprising the same drug D as present in the prodrug GP-D identified to be converted by at least 50% into D under the defined conditions. Optionally, the drug D is connected to the oligopeptide moiety OP in the same was as it is connected to the GP-dipeptide in the prodrug GP-D. In other words, the success of the in step (v) identified prodrug GP-D is indicative or predictive for the success of the candidate prodrug $[C_x\text{-OP}]_y$-D wherein OP is the ALGP-peptide. Such extrapolation is plausible in view of the extensive results described herein as obtained with doxorubicin as drug D.

Further envisaged methods include methods of screening candidate prodrugs having the general structure $[C_x\text{-OP}]_y$-D, wherein C is a capping group;

OP is a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); in particular OP is the tetrapeptide ALGP (SEQ ID NO:1);

D is a drug;

x is an integer being at least 1 when y=1;

y is an integer being at least 1, if y is greater than 1, then at least 1 OP is carrying a capping group; and wherein the linkage between C and OP and the linkage between OP and D is direct or via a linker or spacing group such as a self-immolating or self-eliminating spacer, and wherein, if y is greater than 1, the multiple OP moieties are individually linked to each other directly or via a linker or spacing group and/or are individually linked to D directly or via a linker or spacing group;

wherein said method is comprising the steps of:

(i) obtaining the drug D;

(ii) conjugating the drug D to $[C_x\text{-OP}]_y$ to obtain a $[C_x\text{-OP}]_y$-D prodrug;

(iii) contacting prodrug $[C_x\text{-OP}]_y$-D for 3 h to 24 h at 37° C. with isolated CD10 and/or TOP peptidases and with isolated FAP and/or DPIV peptidases;

(iv) determining the conversion of prodrug $[C_x\text{-OP}]_y$-D into free drug D;

(v) identifying from (iv) a prodrug $[C_x\text{-OP}]_y$-D which is converted by at least 50% to D; and (vi) selecting $[C_x\text{-OP}]_y$-D identified in step (v) as candidate prodrug.

In any of the above screening methods referring to conversion of a prodrug GP-D or of a prodrug $[C_x\text{-OP}]_y$-D to drug D, the conversion percentage used for selecting the candidate prodrug in general lies within at least 50 to 100% (e.g. at least 50%, e.g., at least 55%, at least 60%, at least 65%, at least 70%, at least 75%, at least 80%, at least 55%, at least 90%, at least 95%, at least 99%).

In any of the above alternative screening methods said capping group C may be a phosphonoacetyl group. In a particular embodiment, the OP in any one of the above screening methods is a peptide with a minimum length of 4 consecutive amino acids (tetrapeptide) and a maximum length of 8 amino acids (i.e. a peptide with a length of 4, 5, 6, 7 or 8 consecutive amino acids) which comprises carboxy-terminally a proline comprising dipeptide selected from the group consisting of glycine-proline (GP), alanine-proline (AP), and lysine-proline (KP); more in particular a tetrapeptide with the sequence ALGP (SEQ ID NO:1), ALAP (SEQ ID NO:3), TSGP (SEQ ID NO:4), TSAP (SEQ ID NO:5), KLGP (SEQ ID NO:6), KLAP (SEQ ID NO:7), ALKP (SEQ ID NO:8), TSKP (SEQ ID NO:9), or KLKP (SEQ ID NO:10); even more in particular OP is the tetrapeptide ALGP (SEQ ID NO:1).

In any of the above alternative screening methods said drug D may be selected from the group consisting of doxorubicin, maytansine, geldanamycin, paclitaxel, docetaxel, campthothecin, vinblastine, vincristine, vindesine, methothrexate, aminopterin, amrubicin, or a derivative of any thereof.

The invention further relates to kits comprising a container comprising a prodrug or salt thereof according to the invention or comprising a composition comprising such prodrug or salt thereof. Such kit may further comprise, in the same container (holding a prodrug or salt thereof according to the invention) or in one or more separate containers, one or more further anticancer drugs, such as an antibody or fragment thereof (e.g. as described above). Alternatively, or in addition, such kit may further comprise, in the same container (holding a prodrug or salt thereof according to the invention) or in one or more separate containers, one or more drug resistance reversing agents. Other optional components of such kit include one or more diagnostic agents capable of determining the success of a therapy comprising a prodrug or salt thereof according to the invention; use instructions; one or more containers with sterile pharmaceutically acceptable carriers, excipients or diluents; one or more containers with agents for ADEPT therapy; etc.

All references hereinabove and hereinafter cited are incorporated in their entirety by their reference.

EXAMPLES

Example 1. Synthesis of N-Capped Peptide Prodrug Compounds

1. Synthesis of Fmoc-Peptide-OH
1.1. Synthesis of Fmoc-ALAL-OH

The Fmoc-Leu-Wang resin (5 g, 1 eq) was swollen in dimethylformamide (20 mL) for 30 minutes. The Fluorenylmethyloxycarbonyl (Fmoc)-group was removed by treatment with piperidine (4 mL) in dimethylformamide (16 mL) for 3 minutes, the resin was then filtered, followed by the same treatment for 3 and 7 minutes. The resin was washed with dimethylformamide (20 mL) three times. Fmoc-Ala-OH (2 eq) and 2-(6-chloro-1H-benzotriazole-1-yl)-1,1,3,3-tetramethyluronium hexafluorophosphate (2 eq) were solubilised in dimethylformamide (20 mL) and N,N-diisopropylethylamine (4 eq) was added. The mixture was preactivated during 6 minutes and added to the resin. The resin was then shaken for 60 minutes and washed three times with dimethylformamide (20 mL). The Fmoc group was removed by treatment with piperidine (4 mL) in dimethylformamide (16 mL) for 3 minutes, the resin was then filtered. The same treatment was repeated twice for 3 and 7 minutes. The resin was washed three times with dimethylformamide (20 mL). The same protocol was repeated with Fmoc-Leucine-OH (2 eq) and with Fmoc-Alanine-OH (2eq).

After the last coupling, the resin was washed alternatingly with dimethylformamide (20 mL) and Dichloromethane (20 mL) three times and dried. The Fmoc peptide was cleaved from the resin with a solution of trifluoroaceticacid/triisopropylsilane/water (95:2.5:2.5 v/v/v) (20 mL) during 2 hours. The solvent was evaporated. The product was precipitated in water and filtered. The Fmoc-peptide was dried by lyophilization.

MS (ES$^+$): 609.3 [MH]$^+$; Purity: 90% (determined by HPLC at 214 nm).

1.2. Synthesis of Fmoc-ALG-OH

Prepared as described in paragraph 1.1. starting with a Fmoc-Gly-Wang resin instead of Fmoc-Leu-Wang resin and adding Fmoc-Leu and Fmoc-Ala.

MS (ES$^+$): 482.2 [MH]$^+$; Purity: 92% (determined by HPLC at 214 nm).

1.3. Synthesis of Fmoc-ALPF-OH

Prepared as described in paragraph 1.1. starting with a Fmoc-Phe-Wang resin instead of Fmoc-Leu-Wang resin and adding Fmoc-Pro; Fmoc-Leu and Fmoc-Ala.

MS (ES$^+$): 669 [MH]+; Purity: 98% (determined by HPLC at 214 nm).

1.4. Synthesis of Fmoc-ALAF-OH

Prepared as described in paragraph 1.3. starting with a Fmoc-Phe-Wang resin and adding Fmoc-Ala; Fmoc-Leu and Fmoc-Ala.

MS (ES$^+$): 643 [MH]+; Purity: 90% (determined by HPLC at 214 nm).

1.5. Synthesis of Fmoc-AIG-OH

Prepared as described in paragraph 1.1. starting with a Fmoc-Gly-Wang resin instead of Fmoc-Leu-Wang resin and adding Fmoc-Ile and Fmoc-Ala.

MS (ES$^+$): 482.5 [MH]$^+$; Purity: 60% (determined by HPLC at 214 nm).

1.6. Synthesis of Fmoc-KLG-OH

Prepared as described in paragraph 1.1. starting with a Fmoc-Gly-Wang resin instead of Fmoc-Leu-Wang resin and adding Fmoc-Leu and Fmoc-Lys (IvDde).

MS (ES$^+$): 744 [MH]$^+$ 1.7. Synthesis of Fmoc-GPG-OH

Prepared as described in paragraph 1.1. starting with a Fmoc-Gly-Wang resin instead of Fmoc-Leu-Wang resin and adding Fmoc-Pro and Fmoc-Gly.

MS (ES$^+$): 452 [MH]$^+$

2. Synthesis of Peptide-Doxorubicin Conjugates
2.1. Synthesis of NH$_2$-ALAL-Doxorubicin Doxorubicin (1 eq) was solubilised in dimethylformamide (10 mL). A solution of Fmoc-ALAL-OH (1.2 eq) in dimethylformamide (2 mL) was added to the doxorubicin and the pH was adjusted to pH 8 with N,N-diisopropylethylamine. The solution was stirred at RT and the 2-(6-chloro-1H-benzotriazole-1-yl)-1,1,3,3-tetramethyluronium hexafluorophosphate (1.2 eq) in dimethylformamide (2 mL) was added. The pH of the solution was checked and readjusted to pH 8-8.5. The solution was stirred at room temperature and was checked by HPLC. If the reaction was complete, the Fmoc group was removed by treatment with piperidine (10% final volume) during 5 minutes at RT and the lactate buffer 10% pH 3 was added at 0° C. The mixture was loaded on YMC. The product was recovered with MeOH and the solvent was evaporated. The ALAL-Doxorubicin was purified by HPLC semi-preparative (column Luna, C18).

MS (ES$^+$): 912 [MH]$^+$; Purity: 95% (determined by HPLC at 214 nm).

2.2. Synthesis of NH$_2$-Pro-Doxorubicin and NH$_2$-Gly-Pro-Doxorubicin

Doxorubicin (1 eq) was solubilised in dimethylformamide (10 mL). A solution of Fmoc-Proline-OH (1.2 eq) in dimethylformamide (2 mL) was added to the doxorubicin and the pH was adjusted to pH 8-8.5 with N,N-diisopropylethylamine. The solution was stirred at RT and the 2-(6-chloro-1H-benzotriazole-1-yl)-1,1,3,3-tetramethyluronium hexafluorophosphate (1.2 eq) in dimethylformamide (2 mL) was added. The pH of the solution was checked and readjusted to pH 8-8.5. The solution was stirred at room temperature and was checked by HPLC. If the reaction was complete, the Fmoc group was removed by treatment with piperidine (10% final volume) during 5 minutes at RT and the lactate buffer 10% pH 3 was added at 0° C. The mixture was loaded on YMC. The product was recovered with MeOH and the solvent was evaporated. The Pro-Doxorubicin was purified by HPLC semi-preparative (column Luna, C18). The same protocol was followed with the Fmoc-Glycine-OH (1.2 eq).

P-Dox: MS (ES$^+$): 641 [MH]$^+$; Purity: 99% (determined by HPLC at 214 nm).

GP-Dox: MS (ES$^+$): 698 [MH]$^+$; Purity: 99% (determined by HPLC at 214 nm).

2.3. Synthesis of NH$_2$-ALGP-Doxorubicin Conjugate

Pro-Doxorubicin (1 eq) was solubilised in dimethylformamide (10 mL). A solution of Fmoc-ALG-OH (1.2 eq) in dimethylformamide (2 mL) was added to the doxorubicin and the pH was adjusted to pH 8 with N,N-diisopropylethylamine. The solution was stirred at RT and the 2-(6-chloro-1H-benzotriazole-1-yl)-1,1,3,3-tetramethyluronium hexafluorophosphate (1.2 eq) in dimethylformamide (2 mL) was added. The pH of the solution was checked and readjusted to pH 8-8.5. The solution was stirred at room temperature and was checked by HPLC. If the reaction was complete, the Fmoc group was removed by treatment with piperidine (10% final volume) during 5 minutes at RT and the lactate buffer 10% pH 3 was added at 0° C. The mixture was loaded on YMC. The product was recovered with MeOH and the solvent was evaporated. The ALGP-Doxorubicin was purified by HPLC semi-preparative (column Luna, C18).

MS (ES+): 882 [MH]+; Purity: 99% (determined by HPLC at 214 nm).

2.4. Synthesis of NH$_2$-ALPF-doxorubicin

Prepared as described in 2.1 using Fmoc-ALPF-OH instead of Fmoc-ALAL-OH.

MS (ES$^+$): 971[MH]+; Purity: 97% (determined by HPLC at 214 nm).

2.5. Synthesis of NH$_2$-ALAF-doxorubicin

Prepared as described in 2.1 using Fmoc-ALAF-OH instead of Fmoc-ALAL-OH.

MS (ES$^+$): 947[MH]+Purity: 96% (determined by HPLC at 214 nm).

2.6. Synthesis of NH$_2$-AIGP-doxorubicin

Prepared as described in 2.1 using Fmoc-AIGP-OH instead of Fmoc-ALAL-OH.

2.7. Synthesis of NH$_2$-GPGP-doxorubicin

Prepared as described in 2.1 using Fmoc-GPGP-OH instead of Fmoc-ALAL-OH.

3. Synthesis of PhAc-peptide-doxorubicin 3.1. Synthesis of PhAc-ALGP-doxorubicin NH$_2$-ALGP-Dox (1 eq) was solubilised in dimethylformamide (10 mL). A solution of Phosphonoacetic acid (2.5 eq) in dimethylformamide (2 mL) was added to the peptide-doxorubicin and the pH was adjusted to pH 8 with N,N-diisopropylethylamine. The solution was stirred at RT and the 2-(6-chloro-1H-benzotriazole-1-yl)-1,1,3,3-tetramethyluronium hexafluorophosphate (2 eq) in dimethylformamide (2 mL) was added. The pH of the solution was checked and readjusted to pH 8-8.5. The solution was stirred at room temperature and was checked by HPLC. If the reaction was complete, the mixture was precipitated with diethylether and filtered. The product was recovered with MeOH and the solvent was evaporated. The PhAc-ALGP-Doxorubicin was purified by HPLC semi-preparative (column Luna, C18).

MS (ES+): 1004.4 [MH]+; Purity: 99% (determined by HPLC at 214 nm).

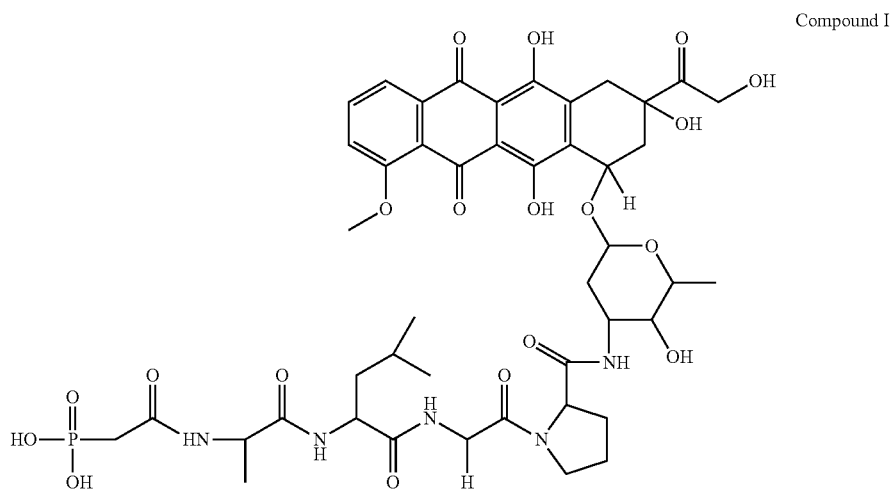 [SMILES: COc1cccc2c1C(=O)c1c(O)c3c(c(O)c1C2=O)CC(O)(C(=O)CO)CC3OC1CC(NC(=O)C2CCCN2C(=O)CNC(=O)C(CC(C)C)NC(=O)C(C)NC(=O)CP(=O)(O)O)C(O)C(C)O1]

Compound I 3.2. Synthesis of PhAc-ALAL-doxorubicin

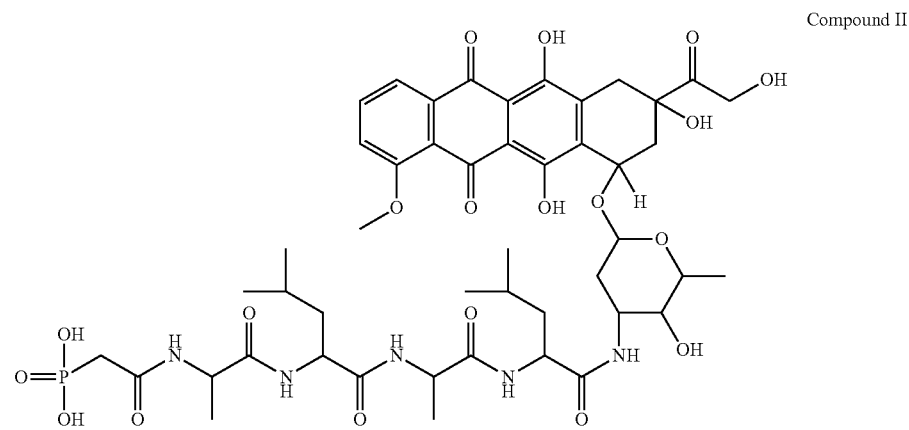 [SMILES: COc1cccc2c1C(=O)c1c(O)c3c(c(O)c1C2=O)CC(O)(C(=O)CO)CC3OC1CC(NC(=O)C(CC(C)C)NC(=O)C(C)NC(=O)C(CC(C)C)NC(=O)C(C)NC(=O)CP(=O)(O)O)C(O)C(C)O1]

Compound II

NH$_2$-ALAL-Dox (1 eq) was solubilised in dimethylformamide (10 mL). A solution of Phosphonoacetic acid (2.5 eq) in dimethylformamide (2 mL) was added to the peptide-doxorubicin and the pH was adjusted to pH 8 with N,N-diisopropylethylamine. The solution was stirred at RT and the 2-(6-chloro-1H-benzotriazole-1-yl)-1,1,3,3-tetramethyluronium hexafluorophosphate (2 eq) in dimethylformamide (2 mL) was added. The pH of the solution was checked and readjusted to pH 8-8.5. The solution was stirred at room temperature and was checked by HPLC. If the reaction was complete, the mixture was precipitated with diethylether and filtered. The product was recovered with MeOH and the solvent was evaporated. The PhAc-ALAL-Doxorubicin was purified by HPLC semi-preparative (column Luna, C18).

MS (ES+): 1034 [MH]+; Purity: 99% (determined by HPLC at 214 nm).

3.3. Synthesis of PhAc-ALPF-doxorubicin

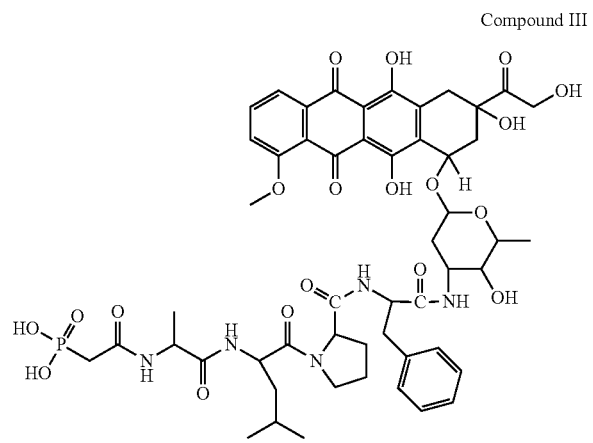 [SMILES: COc1cccc2c1C(=O)c1c(O)c3c(c(O)c1C2=O)CC(O)(C(=O)CO)CC3OC1CC(NC(=O)C(Cc2ccccc2)NC(=O)C2CCCN2C(=O)C(CC(C)C)NC(=O)C(C)NC(=O)CP(=O)(O)O)C(O)C(C)O1]

Compound III

Prepared as described in 3.2 with NH$_2$-ALPF-Dox instead of NH$_2$-ALAL-Dox.

MS (ES$^+$): 1094 [MH]+; Purity: 92% (determined by HPLC at 214 nm).

3.4. Synthesis of PhAc-ALAF-doxorubicin

Prepared as described in 3.2 with NH$_2$-ALAF-Dox instead of NH$_2$-ALAL-Dox.

MS (ES+): 1068[MH]+; Purity: 97% (determined by HPLC at 214 nm).

3.5. Synthesis of PhAc-DLGP-doxorubicin

PhAc-D(Dmab)LGP-doxorubicin was prepared as described in 3.2 with NH2-D(Dmab)LGP-Dox instead of NH2-ALAL-Dox. The protecting group Dmab, also known as 4-{N-[1-(4,4-Dimethyl-2,6-dioxocyclohexylidene)-3-methylbutyl]-amino}benzyl, was removed with hydrazine hydrate 2% during 5 minutes at room temperature. The lactate buffer 10% pH 3 was added at 0° C. and the mixture was loaded on YMC. The product was recovered with MeOH and the solvent was evaporated. The PhAc-DLGP-Doxorubicin was purified by HPLC semi-preparative (column Luna, C18).

MS (ES$^+$): 1048.3 [MH]+; Purity: 99% (determined by HPLC at 214 nm).

3.6. Synthesis of PhAc-TSGP-doxorubicin

PhAc-T(Dmab)SGP-doxorubicin was prepared as described in 3.2 with NH$_2$-T(Dmab)SGP-Dox instead of NH$_2$-ALAL-Dox. The protecting group Dmab was removed with hydrazine hydrate 2% during 5 minutes at room temperature. The lactate buffer 10% pH 3 was added at 0° C. and the mixture was loaded on YMC. The product was recovered with MeOH and the solvent was evaporated. The PhAc-TSGP-Doxorubicin was purified by HPLC semi-preparative (column Luna, C18).

MS (ES): 1008.3 [MH]+; Purity: 99% (determined by HPLC at 214 nm).

3.7. Synthesis of PhAc-AIGP-doxorubicin

Prepared as described in 3.2 with NH$_2$-AIGP-Dox instead of NH$_2$-ALAL-Dox.

MS (ES$^+$): 1004.3[MH]+; Purity: 99% (determined by HPLC at 214 nm).

3.8. Synthesis of PhAc-KLGP-doxorubicin

PhAc-K(IvDde)LGP-doxorubicin was prepared as described in 3.2 with NH2-K(IvDde)LGP-Dox instead of NH$_2$-ALAL-Dox. The protecting group IvDde was removed with hydrazine hydrate 2% during 5 minutes at room temperature. The lactate buffer 10% pH 3 was added at 0° C. and the mixture was loaded on YMC. The product was recovered

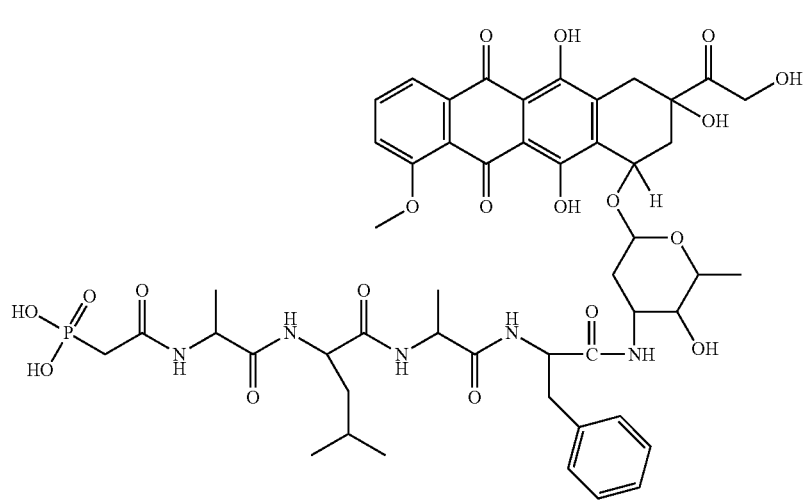

Compound IV with MeOH and the solvent was evaporated. The PhAc-KLGP-Doxorubicin was purified by HPLC semi-preparative (column Luna, C18).

MS (ES$^+$): 1061 [MH]+; Purity: 91.5% (determined by HPLC at 214 nm).

3.9. Synthesis of PhAc-GPGP-doxorubicin

Prepared as described in 3.2 with NH$_2$-GPGP-Dox instead of NH$_2$-ALAL-Dox.

MS (ES$^+$): 974.9[MH]+; Purity: 98% (determined by HPLC at 214 nm).

Similar synthesis procedures as described above were used for the synthesis of PhAc-TSGP-doxorubicin and PhAc-KLGP-doxorubicin 4. Synthesis of succinyl-βALAL-doxorubicin and of succinyl-βALPF-doxorubicin Example 2. In Vitro Evaluation of N-Capped Peptide Prodrugs Stability in Blood and Plasma Method Citrated human blood and plasma from healthy donors (pH 7, Innovative Research) was used to assess the stability of drug conjugates capped with phosphonoacetyl (PhAc-ALAL-Dox, PhAc-ALPF-Dox, PhAc-ALAF-Dox, PhAc-ALGP-Dox, PhAc-DLGP-Dox and PhAc-KLGP-Dox) in comparison with the known Succinyl-βALAL-Dox prodrug conjugate.

The drug conjugates (50 μM) were mixed with human plasma and incubated for 5 hours at 37° C. in a water bath. Fifty μL of samples were collected after 0, 1, 3 or 5 hours and an extraction was performed immediately: 150 μL of acetonitrile was added to the 50 μL samples. Samples were

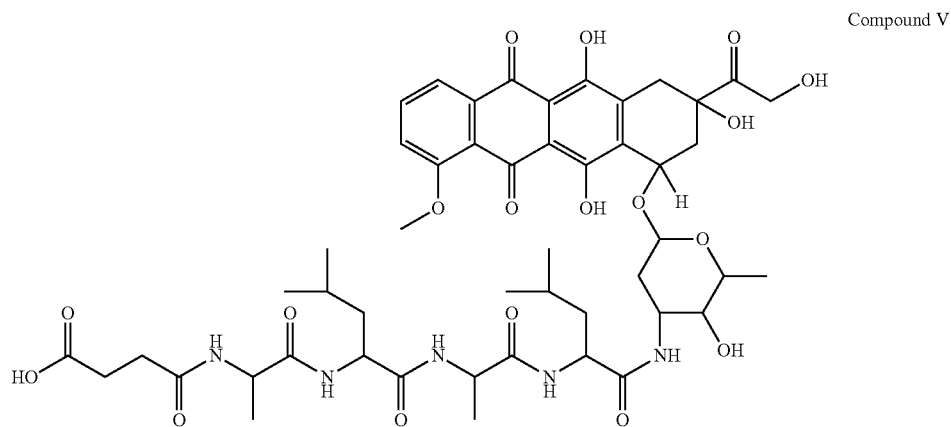 [SMILES: COc1cccc2c1C(=O)c1c(O)c3c(c(O)c1C2=O)CC(O)(C(=O)CO)CC3OC1CC(NC(=O)C(CC(C)C)NC(=O)C(C)NC(=O)C(CC(C)C)NC(=O)C(C)NC(=O)CCC(=O)O)C(O)C(C)O1]

Compound V

Succinyl-βALAL-doxorubicin

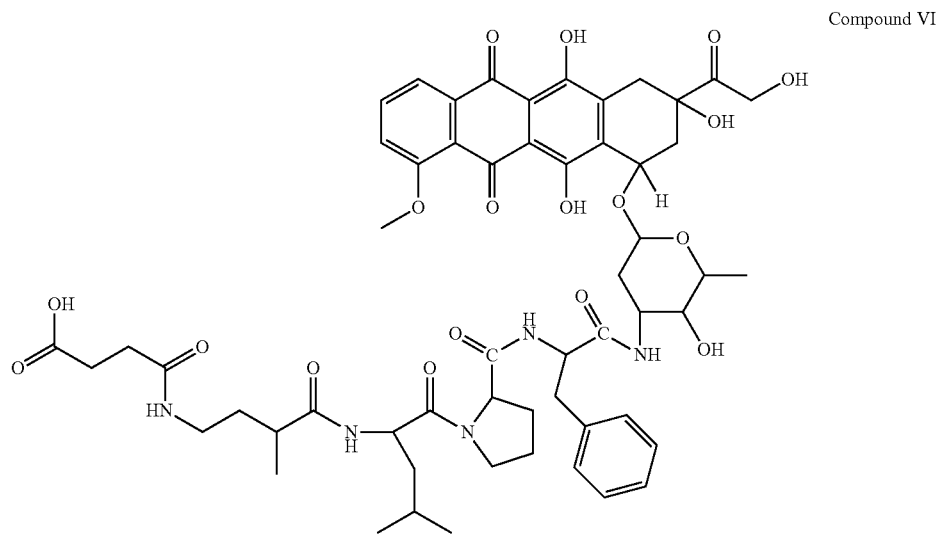 [SMILES: COc1cccc2c1C(=O)c1c(O)c3c(c(O)c1C2=O)CC(O)(C(=O)CO)CC3OC1CC(NC(=O)C(Cc2ccccc2)NC(=O)C2CCCN2C(=O)C(CC(C)C)NC(=O)C(C)CCNC(=O)CCC(=O)O)C(O)C(C)O1]

Compound VI

Succinyl-βALPF-doxorubicin

Succinyl-βALAL-doxorubicin and Succinyl-βALPF-doxorubicin were generated as previously described by Fernandez A M et al., J. Med. Chem., 44:3750-3753 (2001).

vortexed and centrifuged for 10 min at 13 000 rpm at room temperature. Supernatant was collected. Samples were buffered by addition of 200 mM formiate buffer pH 4.5 (1 V sample supernatant+3 V buffer) before HPLC analysis (fluo detection ex=235 nm em=560 nm).

Results

Similarly to Suc-βALAL-Dox, all tested capped conjugates were shown to be stable in human plasma and human blood. After 5 hours of incubation at 37° C. in the presence of blood or plasma, 10% or less of metabolic derivatives of the doxorubicin conjugates were detected in tested samples (Exception: PhAc-ALAL-Dox giving 15% metabolites in blood; data summarized in Table 1 and 2).

TABLE 1

| | % metabolites released after 5 hours incubation at 37° C. in citrated human blood | | | | | | total % |
|---|---|---|---|---|---|---|---|
| Compounds | Dox | L-dox | AL-Dox | GP-dox | F-Dox | P-Dox | metabolites |
| Suc-βALAL-Dox | 2 | 6 | 1 | — | — | — | 9 |
| PhAc-ALAL-Dox | 9 | 6 | 0 | — | — | — | 15 |
| PhAc-ALPF-Dox | 4 | — | — | — | 1 | — | 5 |
| PhAc-ALAF-Dox | 5 | — | — | — | 5 | — | 10 |
| PhAc-ALGP-Dox | 6 | — | — | 3 | — | 0 | 9 |
| PhAc-DLGP-Dox | 2 | — | — | 0 | — | 2 | 4 |
| PhAc-KLGP-Dox | 2 | — | — | 1 | — | 0 | 8 |
| LGP-Dox | 71 | | | 8 | | | |
| GP-Dox | 71 | | | | | | |

TABLE 2

| | % metabolites released after 5 hours incubation at 37° C. in citrated human plasma (pH7) | | | | | | total % |
|---|---|---|---|---|---|---|---|
| Compounds | Dox | L-dox | AL-Dox | GP-dox | F-Dox | P-Dox | metabolites |
| Suc-βALAL-Dox | <1 | 2 | 0 | — | — | — | 2 |
| PhAc-ALAL-Dox | <1 | 2 | 0 | — | — | — | 2 |
| PhAc-ALPF-Dox | 0 | — | — | — | 0 | — | 0 |
| PhAc-ALAF-Dox | 0 | — | — | — | 2 | — | 2 |
| PhAc-ALGP-Dox | 2 | — | — | 0 | — | 0 | 2 |
| PhAc-DLGP-Dox | 2 | — | — | 0 | — | 1 | 3 |
| PhAc-GPGP-Dox | 6 | — | — | 0 | — | 0 | 6 |
| PhAc-TSGP-Dox | 4 | — | — | 4 | — | 0 | 8 |
| LGP-Dox | 63 | | | 2 | | | |
| GP-Dox | 50 | | | | | | |

Example 3. In Vitro Evaluation of N-Capped Peptide Prodrugs Enzymatic Activation 1. Method
1.1. Reactivation Assay in the Presence of Tumor Cell Secreted Peptidases Sub-confluent cultures of LS-174T tumor cells were washed twice with a saline phosphate buffer solution, and fresh culture medium (DMEM-F12 without phenol red) containing 0.02% bovine serum albumin is added (100 µl/cm$^2$). After 24 hours incubation, the conditioned medium is collected, centrifuged for 10 minutes at 300 g, buffered with 1 M Tris-HCl, pH 7.4 (1 volume of buffer+19 volumes of medium) and concentrated 20 times by ultracentrifugation (cutoff threshold of 10 kDa).

Drug compounds (50 µM) were incubated for 0, 1, 3 or 5 hours at 37° C. in the presence of freshly prepared LS174T tumor cell conditioned medium. Fifty µL of sample were collected at each time point and processed as described above for human plasma.
1.2. Reactivation Assay in the Presence of Purified Enzymes (TOP, CD10, CD26, FAP)

CD10 (recombinant human neprilysin, R&D systems, Ref 1182-ZN) was diluted at 20 nM in 0.1M MES pH 6.5 supplemented with 0.2 mg/mL BSA. TOP (recombinant human thimet oligopeptidase, R&D systems, Ref 3439-ZN) was diluted at 10 nM in a solution of 50 mM Tris-HCl pH 7.4/0.5M NaCl/0.1M DTT. CD26 and FAP were diluted at 1 µg/mL in a Tris-HCl pH 7.5 buffer. Reactions were initiated by addition of 50 µM of each compound to enzymes solutions (1 V enzyme solution+1 V 100 µM drug solution). Samples were incubated for 0, 1, or 3 hours at 37° C. in a water bath in the presence of purified enzymes. Fifty µL of sample were collected at each time point and processed as described above for human plasma. Activation of Suc-βALAL-dox was tested in parallel as a reference.
1.3. Results Results of in vitro reactivation assays of N-capped-peptide-Doxorubicin conjugates are presented in Table 3.

Suc-βALAL-Dox is cleaved by CD10 to release 73% of L-Dox. On the contrary, PhAc-ALAL-Dox is not efficiently cleaved by CD10. Less than 5% of L-Dox is released after 3 hours of incubation in the presence of the enzyme. In this example, replacement of the succinyl-A- by the phosphonoacetyl capping group inhibits the peptide-enzyme interaction. PhAc-ALAF-Dox is moderately cleaved by CD10 into F-Dox. Changing the ALAF peptide moiety into ALPF, inhibits cleavage by CD10 whatever the capping group used. PhAc-ALGP-Dox is cleaved by the enzyme into LGP-Dox (25% metabolite released after 3 hours of incubation at 37° C.). PhAc-AIGP-Dox is cleaved by CD10 into IGP-Dox (18% hydrolysis after 3 hours of incubation). PhAc-DLGP-Dox and PhAc-GPGP-Dox, PhAc-KLGP-Dox and PhAc-TSGP-Dox are not or very slightly activated by CD10.

TOP hydrolyses Suc-βALAL-Dox and PhAc-ALAL-Dox to release 64% and 44% of AL-Dox respectively. None of the ALAF-Dox and ALPF-Dox derivatives are cleaved by TOP. TOP activates PhAc-ALGP-Dox, PhAc-KLGP-Dox and PhAc-TSGP-Dox into GP-Dox (72, 31 and 38% of metabolite detected after 3 hours of incubation in the presence of the enzyme). PhAc-DLGP-Dox, PhAc-GPGP-Dox PhAc-AIGP-Dox are not cleaved by TOP.

The sensitivity of the capped tetrapeptidic Dox prodrugs to TOP and CD10 is not contradictory with their blood stability. Most of the blood peptidases are exoproteases for which the capped tetrapeptidic Dox prodrugs are inaccessible as substrates. TOP and CD10 are, however, endoproteases unaffected by the presence of the capping group.

Suc-βALAL-Dox, and PhAc-ALAL-Dox are activated by tumor cell secreted enzymes to release L-Dox and to a lesser extent AL-Dox and Dox. PhAc-ALAF-Dox, PhAc-ALPF-Dox, and Suc-βALPF-Dox are all activated into F-Dox by tumor cell secreted enzymes. PhAc-ALGP-Dox is hydrolyzed in the presence of tumor cell conditioned medium into conversion to Dox after 3 h incubation at 37° C.) and FAP (62% conversion to Dox after 3 h incubation at 37° C.).

Cultured tumor cells are able to convert PhAc-ALGP-Dox to GP-Dox, LGP-Dox to Dox, and GP-Dox to Dox, which indicates the presence of CD10 and/or TOP (PhAc-ALGP-Dox to LGP-Dox or GP-Dox) at the one hand and of CD26 and/or FAP (GP-Dox to Dox) at the other hand. This also confirms a two-step activation process of the prodrug occurring fully extracellularly, i.e., intracellular (lysosomal) processing of the prodrug is not required. This in contrast to L-Dox (released from Suc-βALAL-Dox) that is internalized and further hydrolysed intracellularly into Dox.

TABLE 3

| Compounds | CD10 10 nM | % Metabolites released after 3 h | TOP 5 nM | % Metabolites released after 3 h | LS174T CM20xcc | % Metabolites released after 5 h |
|---|---|---|---|---|---|---|
| Suc-βALAL-Dox | + | 73 ± 17 L-Dox | + | 64 ± 10 AL-Dox | + | 65 ± 17 Dox + AL-Dox + L-Dox |
| Suc-βALPF-Dox | −* | <5 F-Dox | − | 0 | + | 17 ± 2 F-Dox |
| PhAc-ALAL-Dox | −* | <5 L-Dox | + | 44 ± 6 AL-Dox | + | 65 ± 19 Dox + AL-Dox + L-Dox |
| PhAc-ALPF-Dox | − | 0 | −* | <5 F-Dox | + | 11 ± 6 F-Dox |
| PhAc-ALAF-Dox | + | 24 ± 5 F-Dox + LAF-Dox | −* | <5 F-Dox | + | 32 ± 15 F-Dox |
| PhAc-ALGP-Dox | + | 25 ± 4 LGP-Dox | + | 72 ± 14 GP-Dox | + | 81 ± 31 Dox + GP-Dox + LGP-Dox |
| PhAc-DLGP-Dox | − | 0 | − | 0 | − | 0 |
| PhAc-AIGP-Dox | + | 18 ± 3 IGP-Dox | −* | <5 GP-Dox | −* | 3 ± 3 Dox + GP-Dox + IGP-Dox |
| PhAc-KLGP-Dox | −* | <5 LGP-Dox | + | 31 ± 5 GP-Dox | + | 39 ± 13 Dox + GP-Dox |
| PhAc-GPGP-Dox | − | 0 | − | 0 | − | 0 |
| PhAc-TSGP-Dox | − | 0 | + | 38 ± 2 GP-Dox | + | 35 ± 18 Dox + GP-Dox |
| LGP-Dox | − | | − | | + | Dox (23%) + GP-Dox (77%) |
| GP-Dox | | | | | | Dox (28%) |

*less than 5% of metabolites detected

GP-Dox and Dox (56% and 24% of all metabolites detected after 5 hours, respectively), whereas mainly GP-Dox is detected after PhAc-KLGP-Dox and PhAc-TSGP-Dox activation. PhAc-DLGP-Dox, PhAc-AIGP-Dox and PhAc-GPGP-Dox are not activated in the presence of LS174T tumor cells secreted peptidases.

No significant differences between PhAc- and Suc-βA-protecting groups are shown for the ALAL-Dox, and ALPF-Dox derivatives.

In these experiments PhAc-ALAL-Dox and PhAc-ALGP-Dox compounds are better cleaved by tumor cell secreted enzymes and have been selected for further in vivo analysis.

Neither CD26 nor FAP hydrolized either PhAc-ALGP-Dox, Suc-βALAL-Dox or LGP-Dox, in line with these enzymes being exoproteases/dipeptidylproline-proteinases. GP-Dox, however, is a good substrate for both CD26 (97%

Subsequently, the sensitivity of GP-Dox (released from PhAc-ALGP-Dox by TOP) as substrate to the activity of prolyl peptidases was tested in more detail two such enzymes, CD26 (synonym DPIV) and FAP, are emerging as potentially important factors in cancer chemotherapy. CD26 (1 µg/ml) or FAP did not hydrolyze either of PhAc-ALGP-Dox, LGP-Dox (efficiently released from PhAc-ALGP-Dox by TOP) or Suc-βALAL-Dox. However, GP-Dox was shown to be a good substrate for CD26 and FAP and was cleaved into Dox (97% conversion by CD26; 62% conversion by FAP). It is important to notice that in this way, the specificity of PhAc-ALGP-Dox to cancer cells is increased. TOP is involved in the prodrug activation process of Suc-βALAL-Dox or PhAc-ALAL-Dox (releasing AL-Dox) and of PhAc-ALGP-Dox (releasing GP-Dox). While AL-Dox is more generally sensitive to conversion into L-Dox and Dox by cell-secreted peptidases (and with L-Dox being automatically hydrolyzed into Dox intracellularly), GP-Dox seems sensitive to peptidases predominantly released by tumor cells, such as CD26 and FAP. This difference in sensitivity and the difference in enzymes involved in the activation of GP-Dox into Dox (compared to activation of AL-Dox into Dox) are likely to result in differences in toxicities and activities between e.g. PhAc-ALGP-Dox on the one hand and Suc-βALAL-Dox or PhAc-ALAL-Dox on the other hand. Based on this, and as described in the next Example, the in vivo toxicity of PhAc-ALGP-Dox was assessed in comparison with PhAc-ALAL-Dox.

Example 4. Evaluation of the In Vivo Toxicity of PhAc-ALGP-Dox and PhAc-ALAL-Dox Conjugates after Single or Multiple Intravenous Injections in Mice Method PhAc-ALAL-Dox and PhAc-ALGP-Dox were dissolved in saline. Compounds were administered by intravenous bolus injection in the lateral tail vein of OF-1 mice (10 μl/g). The in vivo toxicity was evaluated by monitoring body weight.

Results

Results in FIG. 1 show the high toxicity of PhAc-ALAL-Dox at 160 μmol/kg. No significant body weight loss is observed in the group treated with PhAc-ALAL-Dox at 80 μmol/kg. PhAc-ALGP-Dox injection at the doses of 240 and 320 μmol/kg is well tolerated. A moderate body weight loss with a maximum of 15% at day 28 is recorded in the PhAc-ALGP-Dox 240 μmol/kg treated group showing its lower toxicity in comparison with PhAc-ALAL-Dox. Injection of PhAc-ALGP-Dox at 320 μmol/kg induced a significant body weight loss and one mouse was found dead at day 12. These data indicate that the maximum tolerated dose (MTD) of PhAc-ALGP-Dox after a single iv bolus injection is between 240 and 320 μmol/kg. The toxicity of Dox varies between 30 and 40 μmol/kg indicating that after one intravenous injection PhAc-ALGP-Dox is at least 6 times less toxic.

Example 5. Effectiveness Studies of PhAc-ALGP-Dox after Repeated iv Bolus Injections in Human Xenograft Tumor Models in Nude Mice Method The anti-tumor activity of doxorubicin and PhAc-ALGP-Dox was tested in models of athymic mice (nude/nude NMRI) carrying ectopic xenografts of human LS-174T colon carcinoma or MX-1 mammary carcinoma.

LS174T and MX-1 tumors were established by a subcutaneous implantation of cells ($3\times10^6$ and $10^7$ cells injected respectively) in the right flank of 6 weeks old female NMRI nude mice (Harlan). Treatments were initiated when the tumors had reached a size of 150-200 mm$^3$ (calculated using the following formula: [length×width]/2). The day of the first injection animals were randomly assigned to groups of 4 animals. Doxorubicin, and PhAc-ALGP-Dox were dissolved in saline. Compounds were delivered by bolus intravenous injection (i.v.) in the lateral tail vein at 10 μl/g. During the course of the experiment, clinical signs, body weight and tumor volume were controlled twice a week. Results are presented as the evolution of mean tumor volume as a function of time. Optimal T/C (ratio of mean tumor volume of treated versus control mice) values were used as a measure of treatment efficacy. The optimal T/C % reflects the maximal tumor growth inhibition achieved (TGI=100−(T/C'100)).

Results

As shown in FIG. 2, PhAc-ALGP-Dox was injected twice (once weekly) i.v. at 140 μmole/kg and 160 μmole/kg in nude mice bearing subcutaneously implanted LS174T tumors (colon carcinoma). Their body weight, and the tumor size were followed for 28 days and compared with the Dox (15 μmol/kg) and NaCl treated animals groups. Significant and similar antitumor activity was observed in all treated groups. (Table 4).

These data also confirm the lower toxicity of PhAc-ALGP-Dox since at the doses of 140 μmol/kg and 160 μmol/kg the body weight loss (maximum 10%) was comparable to that induced by Dox given at a 9 times lower dose.

TABLE 4

Tumor Growth Inhibition. Mean RTV and standard deviation were calculated for each group at the end of the study. Drug efficacy was expressed as the percentage tumor growth inhibition (% TGI), calculated using the equation 100 − (T/C'100), where T is the mean RTV of the treated tumor and C is the mean RTV in the control group.

| compound Dose | PhAc-ALGP-Dox 140 μmol/kg | PhAc-ALGP-Dox 160 μmol/kg | Doxorubicin 15 μmol/kg |
|---|---|---|---|
| TGI [% (day)] | 79 (28) | 81 (28) | 55 (28) |

In another experiment, PhAc-ALGP-Dox was injected four times i.v. (at day 0, 3, 6 and 9) at the dose of 100 μmol/kg in nude mice bearing subcutaneously implanted MX-1 tumors (mammary carcinoma). Their body weight and the tumor size were followed for 29 days and compared with the Dox (8 μmol/kg) and NaCl treated animals groups. No significant body weight loss and similar significant antitumor activity (inhibition of tumor growth >60%) were observed for the 2 tested drugs (FIG. 3 and Table 5).

TABLE 5

Tumor Growth Inhibition. Mean RTV was calculated for each group at the end of the study. Drug efficacy was expressed as the percentage tumor growth inhibition (% TGI), calculated using the equation 100 − (T/C'100), where T is the mean RTV of the treated tumor and C is the mean RTV in the control group.

| compound Dose | PhAc-ALGP-Dox 100 μmol/kg | Doxorubicin 8 μmol/kg |
|---|---|---|
| TGI [% (day)] | 60 (29) | 65 (29) |

Example 6. Pharmacokinetic and Tissue Quantification of PhAc-ALGP-Dox and its Metabolites after Single iv Bolus Injection in Mice in Comparison with Doxorubicin at Equimolar Dose Method Pharmacokinetic tissue distribution studies were performed using OF-1 mice. Doxorubicin and PhAc-ALGP-Dox were dissolved in saline at the dose of 8.62 mM and administered to mice by the i.v. route in the lateral tail vein (10 μL/g). At different time points after drug administration (5 min, 30 min, 1 h, 4 h, 7 h, 16 h and 24 h) 3 mice per group were sacrificed by cervical dislocation and blood and heart tissue were collected. Hearts were incised and rinsed carefully in phosphate buffer saline (to eliminate blood in the cardiac cavities), dried on paper and frozen in liquid nitrogen. They were stored until analysis. Blood samples were centrifuged (10 min, 2000 g, 4° C.) to separate the plasma fraction, which was stored for analysis. The hearts were homogenized with an Ultraturrax homogenizer in 1.5 mL water. The protein concentration was measured using the microBCA protein assay (Pierce). The drug tissue quantification was made by HPLC after extraction: 150 µL of acetonitrile was added to the 50 µL samples. Samples were vortexed and centrifuged for 10 min at 13 000 rpm at room temperature. Supernatant was collected. Samples were buffered by addition of 200 mM formiate buffer pH 4.5 (1 V sample supernatant+3 V buffer) before HPLC analysis (fluo detection ex=235 nm em=560 nm).

Results

Doxorubicin and PhAc-ALGP-dox were injected i.v. bolus at the equimolar dose of 86.2 µmol/kg to wild type female OF-1 mice. Evolution of drug and metabolites concentration in plasma and cardiac tissue was determined by HPLC analysis. About 90% of the drug plasma concentration was eliminated in the first five minutes after injection of Dox or PhAc-ALGP-Dox (FIGS. 4 A and B). Less than 1% of the PhAc-ALGP-Dox was rapidly hydrolysed into LGP-Dox, GP-Dox and Dox. These metabolites were no longer detected after 1 hour. The plasma area under curve (AUC) value for Doxorubicin after injection of Doxorubicin is 63 times higher than after injection of PhAc-ALGP-Dox (Table 6).

Since the heart is the target for an important toxicity of Doxorubicin, the cardiac tissue concentration of the free drug was determined. Also determined were the heart AUCs for Doxorubicin after injection of Doxorubicin, and heart AUCs for Dox, GP-Dox and PhAc-ALGP-Dox after administration of PhAc-ALGP-Dox (Table 6). The Dox heart AUC after PhAc-ALGP-Dox administration is 25 times lower than after Dox administration at equimolar dose. Given the clinical cardiotoxic effect of the Dox AUC, these results strongly suggest that PhAc-ALGP-Dox would be significantly less cardiotoxic than Doxorubicin.

TABLE 6

Pharmacokinetic AUC values of PhAc-ALGP-Dox and of its metabolites vs Doxorubicin in cardiac tissue after one i.v. bolus injection to OF-1 mice at the dose of 86.2 µmol/kg

| AUC(area under curve) | Dox | PhAc-ALGP-Dox | | |
|---|---|---|---|---|
| | | Dox | GP-Dox | PhAc-ALGP-Dox |
| Plasma (µM · h) | 63 | 1 | 1 | 97 |
| Heart (pmol · h/mg protein) | 5863 | 235 | 11 | 23 |

Example 7. In Vitro Cytotoxicity Assay of PhAc-ALGP-Dox on Cardiomyocytes

The in vitro cardiotoxicity test was carried out in a relevant and predictive in vitro model for cardiac safety screening in early lead optimization using mouse embryonic stem cell derived cardiomyocytes (Cor.At®, Axiogenesis (Germany)). Cor.At® cardiomyocytes provide a standardized, homogenous and reproducible cell system for the in vitro classification of a compound's cardio-cytotoxic potential. After incubation with test compounds, the neutral red uptake test was used to determine effects which directly affect the viability and integrity of cardiac cells when compared to a non-specific reference cell type, e.g. mouse fibroblasts (MEF).

Results

CorAt cardiomyocytes were incubated in the presence of increasing concentrations of PhAc-ALGP-Dox or of Doxorubicin. Cell viability was determined after 48 h using the neutral red uptake test. Mouse embryonic fibroblasts (MEF) were used as control cells to distinguish cardiac specific toxicity from general cytotoxicity. The dose response curve of PhAc-ALGP-Dox (FIG. 5) did show a moderate toxic effect on Cor.At cardiomyocytes only at the highest concentration tested (20 µg/ml). At this concentration, the effect on MEF is less pronounced (81% viability vs. 37% viability). For the MEF, no IC50 is reached with this compound. At all lower concentrations tested PhAc-ALGP-Dox did not show any toxic effect. The dose response curve of Doxorubicin did show a severe toxic effect on Cor.At cardiomyocytes as well as on MEF at the two highest concentrations tested (20 µg/ml and 2 µg/ml). At 0.2 µg/ml, the compound did show a moderate toxic effect on Cor.At cardiomyocytes, but only a marginal effect on MEF (67% viability of Cor.At cardiomyocytes vs. 89% viability of MEF). Although the effect on Cor.At cardiomyocytes is only slightly higher than on MEF, the compound is considered to exert a cardiotoxic effect, which may be masked by a general cytotoxic effect.

As illustrated in FIG. 5, this study shows that PhAc-ALGP-Dox is 40 to 50 times less cytotoxic than Dox on Cor.At® cardiomyocytes.

Example 8. Assessment of PhAc-ALGP-Dox Activation at the Tumor Site after Single iv Bolus Injection in Nude Mice Bearing LoVo Colon Carcinoma Xenograft Method The tumor activation of PhAc-ALGP-Dox was assessed using athymic mice (nude/nude NMRI) carrying ectopic xenograft of human LoVo colon carcinoma. LoVo tumors were established by a subcutaneous implantation of cells ($10^7$ cells) in the right flank of 6 weeks old female NMRI nude mice (Harlan). Drugs or controls were administered four weeks after subcutaneous implantation of the xenograft. On the day of injection, animals were randomly assigned to groups of 4 animals. The PhAc-ALGP-Dox conjugate was dissolved in saline at increasing doses (1.5, 3.5, 5, 10, 20, 30, 46, and 62 mM). The conjugates were delivered by bolus intravenous injection (i.v.) in the lateral tail vein at 10 µl/g. Twenty-four hours after injection, mice were sacrificed by cervical dislocation and tumors were collected, rinsed in phosphate buffer saline and homogenized. An extraction of drugs from tumor homogenates was performed with acetonitrile and Doxorubicin present in tumors was quantified by HPLC analysis.

Results

Results in FIG. 6 show that Dox tumor concentration increases with the injected dose of PhAc-ALGP-Dox to reach a plateau value at 200 µmol/kg. Results of this example indicate that a limited prodrug activation rate and availability at the tumor site could depend on the maximum of enzyme activity available during the duration of the contact with PhAc-ALGP-Dox.

Example 9. Evaluation of the In Vivo Toxicity of PhAc-ALGP-Dox after Single and Multiple Intraperitoneal Injections in Mice Method PhAc-ALGP-Dox was dissolved in saline and administered by single or multiple intraperitoneal (ip) injections in the lateral tail vein of OF-1 mice (10 µl/g). PhAc-ALGP-Dox was administered at similar cumulative doses of 280 and 560 µmol/kg following different injections schedules: single ip injection; 5 consecutive daily ip injections at 56 and 112 µmol/kg or twice a day for five consecutive days at the doses of 28 and 56 µmol/kg. The in vivo toxicity was evaluated by monitoring the body weight.

Results

Whatever the injection schedule, no body weight loss was recorded in animal groups having received the cumulative dose of 280 µmol/kg of PhAc-ALGP-Dox (FIG. 7). The toxicity study of PhAc-ALGP-Dox after single ip injection at 280 µmol/kg was made separately and results are not shown in FIG. 7. The dose of 560 µmol/kg administered by single ip injection was very toxic. Animals lost 25% of body weight in one week and were sacrificed. Results clearly show that fractionation of the dose in multiple injections reduces the toxicity. Five consecutive daily ip injections of PhAc-ALGP-Dox at 112 µmol/kg also induced a significant body weight loss with a maximum of 22.5% at day 11 but followed by a recovery phase. No body weight loss was observed in the group treated with 10 ip injections (twice a day for five consecutive days) of PhAc-ALGP-Dox at 56 µmol/kg. Considering that the maximum tolerated dose of doxorubicin injected according the same regime is 3 µmol/kg, PhAc-ALGP-doxorubicin is, in these conditions, about 15 times less toxic.

Example 10. Pharmacokinetic and Tissue Quantification of PhAc-ALGP-Dox and its Metabolites after Single Intraperitoneal Injection in Mice in Comparison with Doxorubicin at Equimolar Dose Method Pharmacokinetic tissue distribution studies were performed using OF-1 mice. Doxorubicin and PhAc-ALGP-Dox were dissolved in saline at the dose of 9.2 mM and administered to mice by intraperitoneal route (10 µL/g, 6 mice per group). At different time points after drug administration (5 min, 30 min, 1 h, 4 h, and 24 h), blood samples were collected from the lateral tail vein of three mice using EDTA-coated microtubes (Starsted). After 24 h, 3 mice per group were sacrificed by cervical dislocation and hearts were collected. They were incised and rinsed carefully in phosphate buffer saline (to eliminate blood in the cardiac cavities), dried on paper and frozen in liquid nitrogen. They were stored until analysis. The hearts were homogenized with an Ultraturrax homogenizer in 1.5 mL water. The protein concentration was measured using the microBCA protein assay (Pierce). The drug tissue quantification was made by HPLC after extraction: 150 µL of acetonitrile was added to the 50 µL samples. Samples were vortexed and centrifuged for 10 min at 13 000 rpm at room temperature. Supernatant was collected. Samples were buffered by addition of 200 mM formiate buffer pH 4.5 (1 V sample supernatant+3 V buffer) before HPLC analysis (fluo detection ex=235 nm em=560 nm).

Results

The pharmacokinetics of PhAc-ALGP-Dox in blood was evaluated after intraperitoneal (ip) injection to OF-1 mice. A low percentage (about 1%) of the injected dose reached the blood compartment in the first five minutes after ip injection of PhAc-ALGP-Dox at 92 µmol/kg. The blood concentration of the prodrug was stable for one hour and subsequently decreased. The conjugate was no longer detected after 4 hours (FIG. 8A). The AUC values were 44.2 µM·h and 3.6 µM·h for PhAc-ALGP-Dox and Dox respectively. Results in FIG. 8B show the pharmacokinetics in blood of Doxorubicin at equimolar dose. A low percentage (about 2.5%) of the injected dose reached the blood compartment in the first five minutes after injection. The blood concentration of Dox decreased rapidly within one hour to a very low concentration that remained stable up to 24 hours after injection. The AUC value for Doxorubicin was 70.3 µM·h.

The Doxorubicin cardiac tissue concentration was measured 24 h after ip injection of PhAc-ALGP-Dox or Doxorubicin at equimolar dose. Results in Table 7 show that Doxorubicin accumulates 19 times less after intraperitoneal injection of 92 µmol/kg PhAc-ALGP-Dox than after injection of Doxorubicin at equimolar dose.

TABLE 7

In vivo cardiac concentration of Dox after intraperitoneal injection of Dox and PhAc-ALGP-Dox at 92 µmol/kg. Mice were sacrificed 24 hours after drug administration and hearts were collected. Drug concentration was determined by HPLC analysis after extraction from tissue homogenates. Results are expressed in pmol/mg protein ± SD (concentrations of drugs and proteins were corrected taking into account of the blood remaining in the cardiac tissue).

| treatments | Dox concentration in heart after 24 h pmol/mg protein |
|---|---|
| Dox 92 µmol/kg | 253 ± 60 |
| PhAc-ALGP-Dox 92 µmol/kg | 13 ± 3 |

Example 11. Evaluation of the In Vivo Efficacy of PhAc-ALGP-Dox after Repeated Intraperitoneal Injections in Human Xenograft Tumor Models in Nude Mice Method The efficacy of PhAc-ALGP-Dox was assessed using athymic mice (nude/nude NMRI) carrying ectopic xenograft of human LoVo colon carcinoma or of MX-1 mammary carcinoma in comparison with free Doxorubicin. Tumors were established by a subcutaneous implantation of cells ($10^7$ cells) in the right flank of 6 weeks old female NMRI nude mice (Harlan). Treatments were administered when the tumors reached a size of 150-200 $mm^3$ (measured using a caliper and calculated with the following formula: [length× width]/2). Animals were randomly assigned to groups of 4 to-6 animals. Doxorubicin and PhAc-ALGP-Dox were dissolved in saline. Compounds were delivered by bolus intraperitoneal injection (ip) at 10 µl/g. During the course of the experiment, clinical signs, body weight and tumor volume were controlled twice a week. Results are presented as the evolution of mean tumor volume as a function of time. Optimal T/C (ratio of mean tumor volume of treated versus control mice) values and TGD (tumor growth delay in reaching 1000 $mm^3$) were used as a measure of treatment efficacy. The optimal T/C % reflects the maximal tumor growth inhibition (TGI) achieved (TGI=100−(T/C'100)). A statistical analysis was performed at day 22 using the Mann Whitney t test of the Graph Pad Prism 5.0 software.

Results

Mice bearing Lovo xenografts received twice a day (at 5-6 h interval) for 5 consecutive days (2Q1D5; total of 10 injections) intraperitoneal injections of saline, or of Doxorubicin at 0.5, 1 and 2 µmol/kg, or of Phac-ALGP-Dox at 25, 35 and 50 µmol/kg. Their body weight and the tumor size were followed and compared (FIG. 9). Tumor measurements were stopped in NaCl and Doxorubicin treated groups when tumor necrosis occurred. No significant body weight loss was recorded in this experiment. PhAc-ALGP-Dox induced a dose-dependent antitumor efficacy and increase in tumor growth delay (Table 8). A moderate tumor growth inhibition was observed in the group treated with Doxorubicin at 2 µmol/kg whereas no antitumor activity was seen at the doses of 0.5 and 1 µmol/kg. At day 22, antitumor efficacy was statistically higher with 50 µmol/kg PhAc-ALGP-Dox when compared with 2 µmol/kg Dox with TGI values of 65% and 45% respectively. The absolute growth delay induced by each treatment was calculated as the time in days for tumors in treated mice to grow from 190 to 1,000 mm$^3$ minus the time in days for tumors to reach the same size in vehicle-treated mice. The 50 µmol/kg PhAc-ALGP-Dox treatment protocol resulted in a growth delay of 17 days whereas the highest dose of 2 µmol/kg Doxorubicin alone induced a growth delay of only 6 days.

TABLE 8

Tumor Growth Inhibition and Tumor Growth Delay. Drug efficacy is expressed as the percentage tumor growth inhibition (% TGI), calculated using the equation 100-(T/C' 100), where T is the mean Relative Tumor Volume (RTV) of the treated tumor and C is the mean RTV in the control group. The absolute growth delay induced by each treatment is calculated as the time in days for tumors in treated mice to grow from 190 to 1,000 mm$^3$ minus the time in days for tumors to reach the same size in vehicle-treated mice (TGD).

| | compound | | | | | |
|---|---|---|---|---|---|---|
| | PhAc-ALGP-Dox | | | Doxorubicin | | |
| | Dose (µmol/kg) | | | | | |
| | 25 | 35 | 50 | 0.5 | 1 | 2 |
| TGI [% (day)] | 32 (22) | 60 (22) | 65 (22) | 5 (22) | no | 45(22) |
| TGD [days] | 5 | 13 | 17 | 1 | 0 | 6 |

In another similar study (FIG. 10), drugs or controls were administered for 2 consecutive weeks (2Q1D5×2W; total of 20 injections). In this case, results clearly show the better efficacy and lower toxicity of PhAc-ALGP-Dox compared to Doxorubicin. No significant body weight loss was observed in the PhAc-ALGP-Dox treated groups (max 13% at day 9 in the group 50 µmol/kg PhAc-ALGP-Dox). However a dose-dependent toxicity was observed in the Doxorubicin treated groups. The dose of 1.5 and 2 µmol/kg were very toxic and induced severe body weight loss and animal death. The dose of 1 µmol/kg was slightly less toxic but above the MTD since a continuous loss of weight was observed (max 15% at day 29) and one dead mouse was found at day 29. At this dose, Doxorubicin had a very low activity with a TGI value of 44% at day 29. The highest efficacy was obtained with 50 µmol/kg PhAc-ALGP-Dox with a TGI value of 73% at day 29 and a significant TGD of 22 days (Table 9).

TABLE 9

Tumor Growth Inhibition and Tumor Growth Delay. Drug efficacy is expressed as the percentage tumor growth inhibition (% TGI), calculated using the equation 100-(T/C' 100), where T is the mean RTV of the treated tumor and C is the mean RTV in the control group. The absolute growth delay induced by each treatment was calculated as the time in days for tumors in treated mice to grow from 190 to 1,000 mm$^3$ minus the time in days for tumors to reach the same size in vehicle-treated mice (TGD).

| | compound | | | | | |
|---|---|---|---|---|---|---|
| | PhAc-ALGP-Dox | | | Doxorubicin | | |
| | Dose (µmol/kg) | | | | | |
| | 25 | 35 | 50 | 1 | 1.5 | 2 |
| TGI [% (day)] | 54(29), n = 5 | 53(29), n = 5 | 73(29), n = 5 | 44(29), n = 4 | 65(29), n = 1 | — |
| TGD [days] | 9 | 9 | 22 | 5 | 9 | — |

MX-1 xenografted mice received at 72 h interval 2 cycles of 1 week with 2 daily ip injections of PhAc-ALGP-Dox at 50 µmol/kg or of Doxorubicin at 1 µmol/kg or 1.5 µmol/kg (2Q1D5×2W; total of 20 injections). Doxorubicin at 1.5 µmol/Kg was very toxic and induced severe body weight loss and death of animals. No significant body weight loss was recorded for Doxorubicin at 1 µmol/kg (MTD) and for 50 µmol/kg PhAc-ALGP-Dox. Results in FIG. 11 show that 50 µmol/kg PhAc-ALGP-Dox significantly inhibits tumor growth and has improved efficacy as compared with 1 µmol/kg Doxorubicin (MTD). At the end of the study (day 35), percentages of tumor growth inhibition were 76% and 44% for PhAc-ALGP-Dox or for Doxorubicin respectively (Table 10). In this study tumor necrosis was observed in all groups (mice with necrosed tumors were removed from the study).

These experiments confirmed the 25- to 50-times reduced toxicity of PhAc-ALGP-Dox compared to doxorubicin.

TABLE 10

Tumor Growth Inhibition and Tumor Growth Delay. Drug efficacy is expressed as the percentage tumor growth inhibition (% TGI), calculated using the equation 100 − (T/C'100), where T is the mean RTV of the treated tumor and C is the mean RTV in the control group.

| | compound | |
|---|---|---|
| | PhAc-ALGP-Dox | Doxorubicin |
| Dose (µmol/kg) | 50 | 1 | 1.5 |
| TGI [% (day)] | 76 (35), n = 4 | 44 (35), n = 3 | Not determined |

Example 12. Evaluation of PhAc-ALGP-Dox Efficacy after Repeated Intraperitoneal Injections in the B16F10 Melanoma Lung Metastasis Model in Mice Method The efficacy of PhAc-ALGP-Dox was tested in the well described B16-F10 lung metastatic melanoma model. For that purpose, 5×10$^7$ B16-F10 murine melanoma cells were injected in the lateral vein of C57BL6 mice. Treatments started three days after cells injection. Animal received twice a day (at 5-6 h interval) for 5 consecutive days intraperitoneal injections (total 10 injections/mouse) of saline or of Doxorubicin at 2 and 3.5 µmol/kg or of PhAc-ALGP-Dox at 50 µmol/kg. Five mice per group were sacrificed at day 14 after cells injection. Lungs were collected and processed for melanin quantification (Molecular Pharmacology, 74: 1576-1586, 2008). Survival was determined by observation of the remaining mice.

Results

PhAc-ALGP-Dox significantly inhibits the formation of lung metastasis and increases survival of mice as compared with NaCl and Doxorubicin treated groups (FIG. 12). At day 14 the amount of melanin in lung homogenate was 501 mg/mL in the control group, 183 and 53 mg/mL in the 2 and 3.5 µmol/kg Doxorubicin treated groups and 16 mg/mL in the 50 µmol/kg PhAc-ALGP-Dox treated group. The median survival was 20, 24, 28 and 36 days in groups receiving NaCl, 2 and 3.5 µmol/kg Doxorubicin or 50 µmol/kg PhAc-ALGP-Dox, respectively.

Example 13. Evaluation of the In Vivo Efficacy of PhAc-ALGP-Dox after Repeated Intraperitoneal Injections in the Orthotopic HCT116 Colon Carcinoma Tumor Model in Mice Method HCT116 cells were subcutaneously injected into SCID mice. Once xenografts were established, they were excised and orthotopically implanted into the ceacum of other female γ-irradiated SCID mice using microsurgical techniques. On day 12 after the cancer cells injection, the mice were randomized in four groups of 16. They received for 5 consecutive days 2 daily intraperitoneal injections of saline, of Doxorubicin at 2 µmol/kg and of PhAc-ALGP-Dox at 35 and 50 µmol/kg respectively. On day 34 after injection into the caecum of colonic cancer cells the animals were sacrificed, the number of metastases was counted macroscopically and the primary tumors weighted.

Results

Results are depicted in FIGS. 15 and 16. Doxorubicin at 2 µmol/kg proved to be too toxic for SCID mice and all animals died within 10 days. PhAc-ALGP-Dox was also more toxic on these mice compared to the other tested animals tumor xenograft models and 12 mice survived 34 days at the dose of 35 µmol/kg and 9 mice survived in the 50 µmol/kg treated group.

The control group gave a mean primary tumor weight of 0.88 g with a SD of 0.41. The second group at 30 µmol/kg of PhAc-ALGP-Dox had a primary tumor weight of 0.69 g with a SD of 0.25 while the group at 50 µmol/kg PhAc-ALGP-Dox presented a significant tumor weight loss with 0.44 g with a SD of 0.10.

The number of hepatic metastases were respectively of 20 (SD of 33) and of 24 (SD of 26) for the controls and the group treated at 30 µmol/kg PhAc-ALGP-Dox. The effect of 50 µmol/kg PhAc-ALGP-Dox was very significant with a mean number of metastases of 1.78 with a SD of 2.9.

Although PhAc-ALGP-Dox was not totally devoid of toxicicty, this prodrug could at least be retained for treating/preventing metastases (e.g. hepatic metastases of colon carcinoma) if it would not be effective against the primary tumor itself (e.g. colon carcinoma) at non-toxic levels.

Example 14. Evaluation of PhAc-ALGP-Dox Leucopenia in Comparison with Doxorubicin The leucopenic effects of PhAc-ALGP-Dox (35 µmol/kg ip) and of Doxorubicin (3.5 µmol/kg ip) were compared in two independent experiments. CD1 mice received two daily intraperitoneal injections of drugs for five consecutive days (total 10 injections/mouse; 2×5 animals per group). The mice body weight evolution was recorded. Blood was collected from the tail vein in EDTA-coated Microvettes tubes (Starsted) at day 4, 11 and 15 after treatment initiation. White blood cells (WBC) were counted using the SCILvet abc hematologic analyzer. The increase or decrease in WBC was expressed as a percentage of WBC on day 0 (100%) for each mouse. FIG. 13 shows combined results of the two studies.

FIG. 13 A gives the mean and SD of the body weight variation of the two groups and 13 B the white blood cells variations as a percentage of WBC on day 0 for each mouse. These results clearly indicate the absence of toxicity of 35 µmol/kg PhAc-ALGP-Dox ip as compared to Doxorubicin administered at a 10 times lower dose. No leucopenic effect and body weight loss were observed in the PhAc-ALGP-Dox treated group. On the other hand, in the doxorubicin treated group, one mouse was found dead at day 11 as well as 3 mice at day 15. Doxorubicin induced a moderate to severe leukopenia (on average—43% WBC at day 15) and body weight loss (on average −15% at day 15).

Example 15. Evaluation of PhAc-ALGP-Dox Chronic Cardiotoxicity Method

Chronic cardiac toxicity of PhAc-ALGP-Dox in mice was morphologically evaluated as previously described by Bertazzoli et al. 1979 (Cancer Treat Rep 63, 1877-1883). CD1 female white mice were treated by bolus intravenous injection in the tail vein at 10 µL/g (6 mice per group). Compounds were injected twice a week, ten times. Animals were not treated for 2 weeks between the first four injections and the last six injections to allow recovery of the bone marrow depression. The treatment dose-levels of PhAc-ALGP-Dox were: 13.8; 27.6; 55.2; and 82.8 µmol/kg. Doxorubicin 6.9 µmol/kg was used as a reference. Three weeks after the last injection, animals were deeply anaesthetized by intraperitoneal injection of nembutal (50 mg/kg) and exsanguinated. The hearts were carefully collected, rinsed in NaCl 9°/oo and fixed in a 10% formaldehyde solution. Samples were processed for histopathological analysis (CITox Lab, France). The heart was trimmed, embedded in paraffin wax, sectioned at a thickness of 4 microns and stained with hematoxylin-eosin before microscopic evaluation. During the course of the experiment, body weight was controlled before each injection or once a week.

Results

No body weight loss was observed in the groups treated with PhAc-ALGP-Dox (FIG. 14). At the end of the treatment, doxorubicin treated animals showed signs of weakness and decreased locomotor activity. A moderate decrease in body weight was recorded in the Doxorubicin treated group with a maximum of 8% at the time of sacrifice.

Results of microscopic evaluation of cardiotoxicity are shown in Table 11. One mouse of the Doxorubicin treated group was not submitted for microscopic examination because of premature death (at day 17). In all mice given 6.9 µmol/kg Doxorubicin, there were microscopic cardiac changes. There was minimal or slight vacuolation of the myocardium characterized by the presence of small clear cytoplasmic vacuoles in myofibers scattered in the ventricles, septum and atria. The nuclei of myofibers in the ventricles and septum were enlarged in 3 mice out of 5. In addition, there were atrophy and or lesions in the atrial myocardium, particularly on the left side. Atrial myofiber atrophy and inflammatory infiltrate were seen in 4 mice out of 5, along with fibrin thrombi in 3 mice out of 5. In one of these mice, there was also degeneration/necrosis of myofibers. The administration of PhAc-ALGP-Dox did not induce any pathologic microscopic findings in the heart at any dose levels (i.e. up to a 12 times higher dose as compared with Doxorubicin).

TABLE 11

Microscopic evaluation of PhAc-ALGP-Dox chronic cardiotoxicity in mice in comparison with Doxorubicin

|  | NaCl | Doxorubicin | PhAc-ALGP-Dox | | | |
|---|---|---|---|---|---|---|
|  | \multicolumn{6}{c}{Dose (µmol/kg)} | | | | | |
|  | 0 | 6.9 | 13.8 | 27.6 | 55.2 | 82.8 |
| Number of mice | 6 | 5 | 6 | 6 | 6 | 6 |
| Vacuolation; myofib. | 0 | 5 | 0 | 0 | 0 | 0 |
| Grade 1 | 0 | 4 | 0 | 0 | 0 | 0 |
| Grade 2 | 0 | 1 | 0 | 0 | 0 | 0 |
| Thrombus; atrium | 0 | 3 | 0 | 0 | 0 | 0 |
| Grade 1 | 0 | 3 | 0 | 0 | 0 | 0 |
| Atrophy; myofiber | 0 | 4 | 0 | 0 | 0 | 0 |
| Grade 1 | 0 | 1 | 0 | 0 | 0 | 0 |
| Grade 2 | 0 | 3 | 0 | 0 | 0 | 0 |
| Degeneration/necrosis; myocardium | 0 | 1 | 0 | 0 | 0 | 0 |
| Grade 1 | 0 | 1 | 0 | 0 | 0 | 0 |
| Infiltration; mix. Cells | 0 | 4 | 0 | 0 | 0 | 0 |
| Grade 1 | 0 | 4 | 0 | 0 | 0 | 0 |
| Enlarg. Nuclei; myofib. | 0 | 3 | 0 | 0 | 0 | 0 |
| Grade 1 | 0 | 3 | 0 | 0 | 0 | 0 |

General conclusion: the maximal tolerated dose of PhAc-ALGP-Dox is, depending on different schedules and mode of administration between 6 to 16 times less toxic than Dox and significantly more active on three experimental tumor models (LS174T and MX-1 xenografts and the lung metastasis B16 melanoma model). PhAc-ALGP-Dox does not induce leukopenia at active doses and does not present cumulative cardiotoxicity in a mouse model at a dose equivalent to 12 times that of Doxorubicin at its MTD level.

Example 16. Synthesis and Evaluation of Other Cytotoxic Compounds Conjugated to PhAc-ALGP 1. PhAc-ALGP-Maytansine Maytansine is a potent microtubule-targeted compound that induces mitotic arrest and kills tumor cells at subnanomolar concentrations. However, its side effects and lack of tumor specificity have prevented successful clinical use. It inhibits microtubule assembly, inducing microtubule disassembly, and disrupts mitosis. Maytansine exhibits cytotoxicity against many tumor cell lines and displays about 100-fold higher cytotoxicity than the Vinca alkaloids and about 1000-fold higher toxicity than doxorubicin.

In clinical trials gastrointestinal and central neurologic toxicity were dose limiting whereas myelosuppression was infrequent. When evaluated as a single agent, maytansine failed to show any significant response in patients with different types of cancers.

The figure below depicts maytansine:

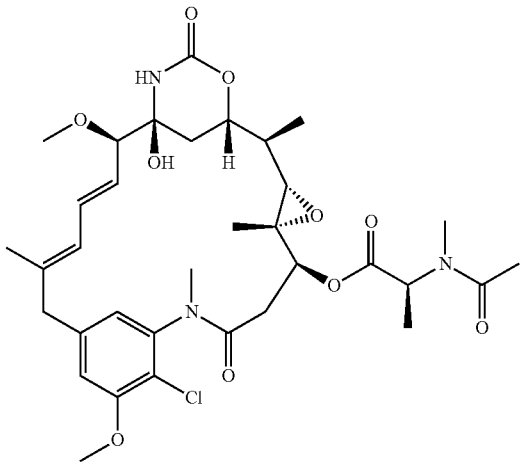 [SMILES: COc1cc2cc(c1Cl)N(C)C(=O)C[C@H](OC(=O)[C@H](C)N(C)C(C)=O)[C@]1(C)O[C@H]1[C@H](C)[C@@H]1C[C@@](O)(NC(=O)O1)[C@H](OC)/C=C/C=C(\C)C2]

Maytansine can be conjugated to PhAc-ALGP via a self-immolating spacer reacting with its free —NH or OH group. Maytansine is commercially available (e.g. Medkoo Biosciences; Xuzkou Kaiyide Chemical Co).

2. PhAc-ALGP-Geldanamycin

Geldanamycin and derivates thereof are a family of a benzoquinone ansamycins, antibiotics originally isolated on the basis of their weak antibiotic activity that were subsequently shown to display potent antitumor activity. Geldanamycin induces, compared to their normal cellular counterparts, preferential degradation of proteins that are mutated in tumor cells such as v-src, bcr-abl and p53. This effect is mediated via Hsp90. Despite its potent antitumor potential, geldanamycin has several major disadvantages as antitumor agent which has led to the development of geldanamycin analogues, in particular analogues containing a substitution on the 17 position.

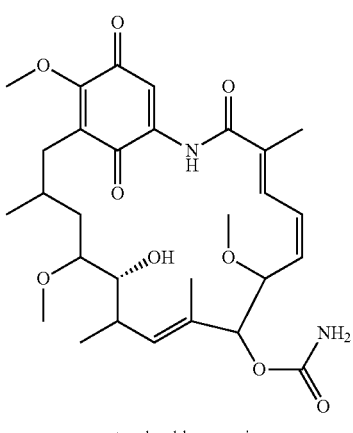

natural geldanamycin

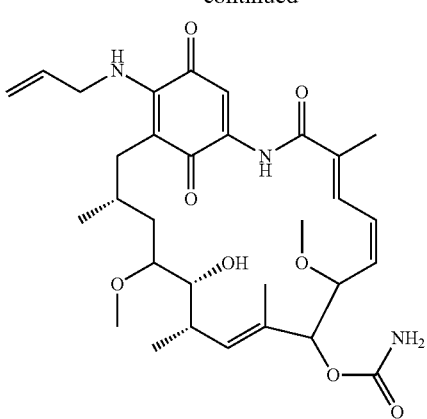

geldanamycin derivated at the 17$^{th}$ position to yield 17AAG

Derivatization of geldanamycin at the position leads to 17AAG (17-(allylamino)-17-demethoxygeldanamycin) hat has lower in vivo toxicity than geldanamycin. Even though Hsp90 affinity to 17AAG is less than to geldanamycin, 17AAG and geldanamycin gave biologic effects in malignant cells at similar or same concentrations. Geldanamycin binds with high affinity to the ATP binding pocket of Hsp90. Hsp90 is a ubiquitous molecular chaperone critical for the folding, assembly and activity of multiple mutated and overexpressed signaling proteins that promote the growth and/or survival of tumor cells. Binding of geldanamycin to Hsp90 causes the destabilization and degradation of its target. Burke et al. 2009 (Bioorg Med Chem Lett 19, 2650-2653) described a technique to link geladanamycin to antibodies with a linker cleavable by lysosomal enzymes. This linker incorporates a (self-immolating) valine-alanine-p-aminobenzyl-amino moiety to allow attachment with the amino-group of geldanamycin on one hand and with a free amino-group of the antibody on the other hand. The same linking technique can be used to obtain PhAc-ALGP-geldanamycin but after substitution in the linker of the valine-alanine dipeptide by the alanine-leucine-glycine-proline tetrapeptide. Geldanamycin is commercially available (e.g. Calbiochem, Fermentec Biosciences, AG Scientific-Paclitaxel).

3. PhAc-ALGP-Paclitaxel and PhAc-Docetaxel

Taxanes are diterpenes produced by the Taxus plants. They include paclitaxel (Taxol) and docetaxel (taxotere; see Figure below)

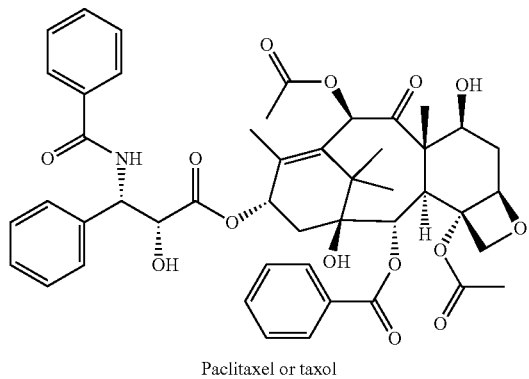 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Paclitaxel or taxol

Paclitaxel is one of several cytoskeletal drugs that target tubulin. Paclitaxel-treated cells have defects in mitotic spindle assembly, chromosome segregation, and cell division. Paclitaxel stabilizes the microtubule polymer, protecting it from depolymerisation, and thereby blocks mitosis. Recent studies have demonstrated that suppression of dynamics occurs at concentrations lower than those needed to block mitosis. At the higher therapeutic concentrations, paclitaxel appears to suppress microtubule detachment from centrosomes, a process normally activated during mitosis. Paclitaxel is approved for treatment of ovarian, breast and lung cancers and Kaposi's sarcoma. Common side effects include nausea and vomiting, loss of appetite and haematological toxicity such as neutropenia, anemia and thrombocytopenia, although some side effects are associated with the excipient used, Cremophor EL, a polyoxyethylated castor oil.

Docetaxel or taxotere differs from paclitaxel at two positions in its chemical structure. It has a hydroxyl functional group on carbon 10 (where paclitaxel has an acetate ester), and a tert-butyl carbamate ester exists on the phenylpropionate side chain instead of the benzylamide in paclitaxel. The carbon 10 functional group change causes docetaxel to be more water soluble than paclitaxel. The hydroxyl group on carbon 2 remains unmodified.

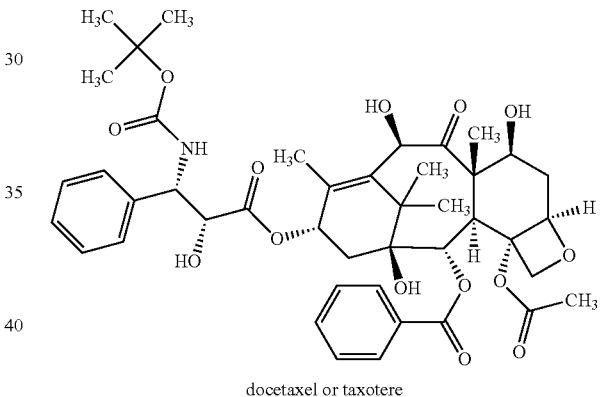

docetaxel or taxotere

Paclitaxel was linked to antibodies by a simple reaction (Guillemard & Saragovi 2001; Cancer Res 61, 694-699). Paclitaxel was derivatized by reacting glutaric aldehyde to give 2'-glutaryl-paclitaxel containing a cleavable ester bond. 2'-glutaryl-paclitaxel was then activated by removal of a hydroxyl group with carbodiimide and bound to an antibody directly via its amino-group to form a peptide linkage. This technique was used recently (Garcia et al Oncogene 2012; doi: 10.1038/onc.2012.283) to link taxol to an antiherceptin monoclonal antibody. Experimental results indicate that the conjugate is active in experimental tumors indicating that the drug is released in vivo.

Paclitaxel was also conjugated to antibodies after succinylation of paclitaxel at the 2'position and coupling to antibodies via an amide bound (Safavy et al. 2003; Bioconj Chem 14, 302-310). Similar methods of conjugating activated 2'-glutaryl or 2'-succinyl paclitaxel to the PhAc-ALGP-tetrapeptide; alternatively a self-immolating spacer linked on the carboxyl group of the succinyl-paclitaxel is used. And it is reasonable to expect release in vivo of taxol from the PhAc-ALGP-paclitaxel conjugate, certainly taking into account that a tetrapeptide exerts a much smaller steric hindrance than antibodies do. Stability of the succinyl-linked prodrug conjugate in blood may be a problem given the ester nature of the succinyl group on paclitaxel. Therefore it may be preferable to use a self-immolating group between the 2' carbon and the tetrapeptide. These conjugates methods could also be applied to docetaxel in view of unchanged 2' carbon. Paclitaxel is commercially available (e.g. Hulang Pharmaceutical, TradeIndia).

4. PhAc-ALGP-Camptothecin

Camptothecin (CPT; structure depicted below) is a cytotoxic quinoline alkaloid that inhibits the DNA enzyme topoisomerase I (TopoI). CPT showed remarkable anticancer activity in preliminary clinical trials but suffers from low solubility and (high) adverse drug reaction. Because of these disadvantages synthetic and medicinal chemists have developed numerous syntheses of camptothecin and various derivatives. Two CPT analogues have been approved and are used in cancer chemotherapy today: topotecan and irinotecan.

Studies have shown that substitution at position 7, 9, 10 and 11 can have positive effect on CPT activity and physical properties, e.g. potency and metabolic stability. Enlargement of the lactone ring by one methylene unit also enhances its abilities, as in homocamptothecin. Substitution at position 12 and 14 leads to an inactive derivative.

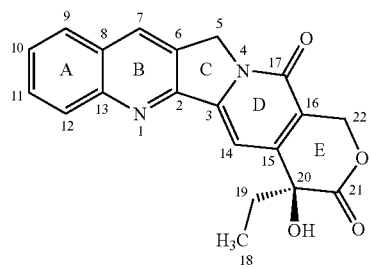

Burke et al. 2009 (Bioconjug Chem 20, 1242-1250) described the design and the synthesis of conjugates between antibodies and camptothecin analogues. 7-butyl-1O-aminocamptothecin and 7-butyl-9-amino-10,11-methylenedioxy-camptothecine are 10- to 1000-times more potent than campthothecin and can be linked to antibodies via a dipeptide linker with a selfimmolative spacer releasing the drugs in presence of lysosomal enzymes. A similar technique is feasible to arrive at a conjugate of camptothecin or a derivative thereof with PhAc-ALGP. Camptothecin is commercially available (e.g. Calbiochem, Seeboo Dhakhwa).

5. PhAc-ALGP-vinblastine and PhAc-ALGP-vincristine

Vinblastine (structure depicted below) is an anti-microtubule drug used to treat certain kinds of cancer, including Hodgkin's lymphoma, non-small cell lung cancer, breast cancer, head and neck cancer, and testicular cancer. It is also used to treat Langerhans cell histiocytosis. Vinblastine was traditionally obtained from *Catharanthus roseus*, also known as *Vinca rosea*, a Madagascar periwinkle. It is generated in the plant by the joining of the alkaloids catharanthine and vindoline.

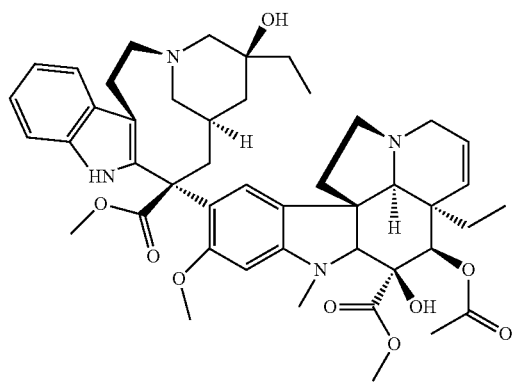

At very low concentrations it suppresses microtubule dynamics and at higher concentrations it reduces microtubule polymer mass. Common side effects are low blood count of white and red blood cells, and platelets may temporarily decrease.

Vincristine is a close analog differing from vinblastine only by CHO instead of CH3 on $N_1$. Although very similar to vinblastine in structure it has other therapeutic indications and a very severe side effect. Its main indications are non-Hodgkin's lymphoma, in acute lymphoblastic leukemia, and in treatment for nephroblastoma (Wilms' tumor, a kidney tumor most common in young children). The main side-effects of vincristine are peripheral neuropathy, hyponatremia, constipation, and hair loss. Peripheral neuropathy can be severe, and be a reason to avoid, reduce, or stop the use of vincristine.

PhAc-ALGP-vinblastine or -vincristine conjugates can be obtained by linking a desacetyl vinblastine or -vincristine via a self-immolative spacer bound on their carbon $C_4$.

Kandukuri et al. 1985 (J Med Chem 28, 1079-1088) developed a synthesis method of amino acid derivatives of vinblastine involving an amide linkage with the carboxylic end side chain of the amino acid. The linkage was obtained by a mixed anhydride condensation between the $C_4$ deacetylvinblastine and N-maleoyl amino acids; vinblastine-C4 amino acid maleoyls were also conjugated to lactosaminated serum albumin and shown to be active against HepG2 carcinoma (Rao et al. 1989; Anticancer Res 9, 973-979). Logically the same procedure is applicable to vincristine. Conjugation of vinblastine or vincristine to PhAc-ALGP is likewise achievable with this method. The latter conjugates have a better safety profile than unconjugated vinblastine or vincristine while retaining the anticancer activity. Vinblastine is commercially available (e.g. Medkoo Biosciences), as well as vincristine (e.g. Tocris Bioscience, Medkoo Biosciences).

6. PhAc-ALGP-Methotrexate and PhAc-ALGPAminopterin

Methotrexate, is an antimetabolite and antifolate drug. It is used in treatment of cancer and of autoimmune diseases.

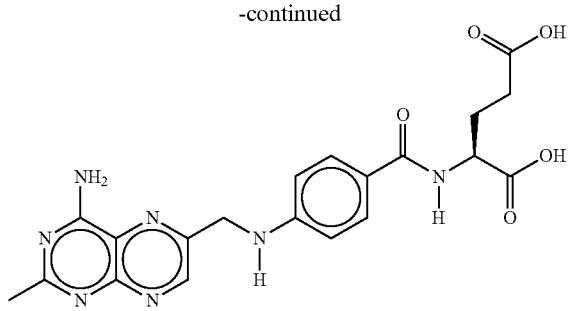

The similarity in structure of dihydrofolic acid (top) and methotrexate (bottom) suggests that methotrexate is a competitive inhibitor of dihydrofolic acid.

Methotrexate was originally developed and continues to be used for chemotherapy either alone or in combination with other agents. It is effective for the treatment of a number of cancers including: breast, head and neck, leukemia, lymphoma, lung, osteosarcoma, bladder, and trophoblastic neoplasms. The most common adverse effects include: ulcerative stomatitis, low white blood cell count and thus predisposition to infection, nausea, abdominal pain, fatigue, fever, dizziness, and acute pneumonitis.

Methotrexate is thought to affect cancer and rheumatoid arthritis by two different pathways. For cancer, methotrexate allosterically inhibits dihydrofolate reductase (DHFR), an enzyme that participates in the tetrahydrofolate synthesis. The affinity of methotrexate for DHFR is about one 1000-fold that of folate. DHFR catalyses the conversion of dihydrofolate to the active tetrahydrofolate. Methotrexate, therefore, inhibits the synthesis of DNA, RNA, thymidylates, and proteins. For the treatment of rheumatoid arthritis, inhibition of DHFR is not thought to be the main mechanism, but rather the inhibition of enzymes involved in purine metabolism, leading to accumulation of adenosine, or the inhibition of T cell activation and suppression of intercellular adhesion molecule expression by T cells.

Umemoto et al. 1989 (Int J Cancer 43, 677-684) described a method to link methotrexate via free carboxyl group to antibodies with a of Ala-Leu-Ala-Leu linker This method can likewise be applied to link methotrexate to PhAcALGP peptide and will restore the free carboxyl group after enzymatic cleavage. Derivatives of the alpha-carboxylate group are relatively non-active and non-toxic in vitro since a free alpha-carboxylate group is necessary for the binding of methotrexate to DHFR Potential prodrugs of methotrexate were also produced in which the 2-aminogroup was acylated with alpha-amino acids (Smal et al. 1995; Biochemical Pharmacology 49, 567-574). These aminoacyl derivatives are substituted at the 2-$NH_2$ pteridine ring of methotrexate. Importantly, the 2-leucyl-methotrexate derivative is rapidly cleaved and activated in presence of serum illustrating its sensitivity to serum exoproteases. This makes it plausible for a PhAc-ALGP-methotrexate conjugate to display tumor cell specific anticancer activity Linking methotrexate to PhAc-ALGP is performed via the above-described technique. Methotrexate is commercially available (e.g. CF Pharma Ltd, Yaskika Pharmaceuticals).

Aminopterin (4-aminopteroic acid), a 4-amino analog of folic acid, is an antineoplastic drug with immunosuppressive properties. Aminopterin is a synthetic derivative of pterin. Aminopterin works as an enzyme inhibitor by competing for the folate binding site of the enzyme dihydrofolate reductase. Its structure is very similar to that of methotrexate and it has also a 2-$NH_2$ on its pteridine moiety. Developed before methotrexate, it was superseded by the latter early in the 1950's because of its greater toxicity that could result from a greater activity. Greater effectiveness was confirmed recently in the treatment of acute leukemia (Cole et al. 2005; Clin Cancer Res 11, 8089-8096). A PhAc-ALGP-aminopterin conjugate can be synthesized by the methods described for PhAc-ALGP-methotrexate and enhanced specificity of the anticancer activity for tumor cells is likewise plausible. Aminopterin is commercially available (e.g. Cameo Chemicals, Sigma Aldrich).

7. PhAc-ALGP-Amrubicin

Amrubicin (structure depicted below) is a third-generation, synthetic anthracycline analogue that has demonstrated substantial clinical efficacy in the treatment of small cell lung cancer. Amrubicin is a potent topoisomerase II inhibitor and is being studied as a single agent and in combination with anti-cancer therapies for a variety of solid tumors, including lung and breast. It has been granted the orphan drug classification by the FDA.

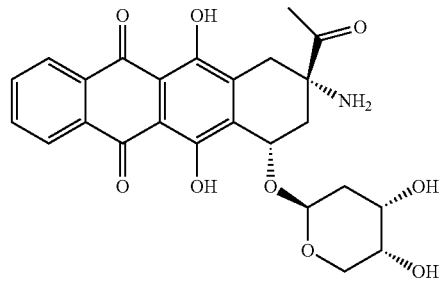 [SMILES: CC(=O)[C@]1(N)Cc2c(O)c3c(c(O)c2[C@@H](O[C@H]2C[C@H](O)[C@H](O)CO2)C1)C(=O)c1ccccc1C3=O]

It is an anthracycline that is structurally different from that of doxorubicin. However it possesses an $NH_2$ group on its tetracycline ring. Side effects are similar to that of doxorubicin such as neutropenia and thrombocytopenia. Nothing is known about chronic cardiotoxicity as possible side-effect.

As outlined for doxorubicin, conjugation of PhAc-ALGP to this anthracycline is applied. The presence of the PhAc-ALGP increases tumor cell selectivity of the anticancer activity of amrubicin. Amrubicin is commercially available (e.g. Medkoo Biosciences, Santa Cruz Biotech).

8. Common Steps for the In Vitro and In Vivo Testing of PhAc-ALGP-Cytotoxic Compound Conjugates The synthesis of the derivatives will be based on the methods described summarily hereinabove and more detailed in the referenced publications mentioned for each cytotoxic compound.

In a first step, a GP-dipeptide is conjugated to the cytotoxic compound and analytical methodology is developed for detecting and/or quantifying the GP-cytotoxic compound conjugate, the cytotoxic compound, and intermediates between the two. Such methodology may include one or more of spectrophotometry, high performance liquid chromatography (HPLC), mass spectrometry (MS), combined HPLC and MS, NMR and MALDI-TOF (matrix-assisted laser desorption/ionization—Time-of-flight), or even UPLC-MS/MS (ultra-high performance liquid chromatography with tandem mass-spectrometry).

The purified GP-cytotoxic compound conjugate is tested in vitro in a biological system to confirm its cytotoxicity. For GP-cytotoxic compound conjugates confirmed to be cytotoxic, synthesis of the complete PhAc-ALGP-cytotoxic compound conjugate is performed and analytical methodology is developed for detecting and/or quantifying the PhAc-ALGP-cytoyoxic compound conjugate, the cytotoxic compound, and intermediates between the two.

Although chemical synthesis and analytical method development are expected to be routine, it may be desired to study possible modifications in the initially envisaged synthesis method or to develop of a new synthesis method such as to e.g. increase yield and/or purity of the peptide-drug conjugate.

9. In Vitro Testing Steps 9.1. Biological In Vitro Testing of the GP-Cytotoxic Compound Conjugate The cytotoxic activity of the starting compound (unconjugated, the "parent" drug) and of its conjugated derivative (the "GP-drug") will be tested on in vitro cell lines. The cell lines will be at least some of those mentioned in the referenced publications mentioned hereinabove for each of the cytotoxic compounds. It will be necessary to do tests as a function of drug concentration and time of incubation. The GP-drug should be much less active than the parent drug after short incubation times. With increasing incubation time, this difference could become less significant due to increased hydrolysis of the GP-drug by exoproteases present in serum that is part of the incubation media. In such case, the presence of exoproteases in serum could be confirmed, if possible, by incubation of the GP-drug in serum-free incubation media.

More crucial, however, is the analysis of cytotoxicity of the GP-drug before and after preincubation with purified FAP and/or DPIV prolyl-peptidases. In analogy with GP-doxorubicin, action of FAP and/or DPIV prolyl-peptidases on the GP-drug should significantly increase the cytotoxicity through release of the free drug. If the results of this analysis are positive, synthesis of the PhAc-ALGP-drug is performed. If the results are negative, this could result from the inaccessibility to the enzymes of the proline-drug bond. A solution to this problem could be to intercalate a spacer with an available $NH_2$-terminal between proline and the drug provided that such derivative retains its original cytotoxic effect. Another possible solution would be to intercalate a self-immolating spacer that restores the original drug after hydrolysis of the drug-spacer and proline bound. One possible spacer of this type is PABC or PAB (para-aminobenzyloxycarbonyl), attaching the drug moiety to the ligand in the conjugate. The linker moiety comprises a peptide sequence that is a substrate for an extracellular enzyme, for example FAP, that cleaves the peptide at an amide bond. The peptide further contains a self-immolating moiety which connects the drug and the protein peptide sequence. Upon cleavage of the peptide sequence by an intracellular enzyme the self-immolating moiety cleaves itself from the drug moiety such that the drug moiety is in an underivatized and active form.

9.2. Biological In Vitro Testing of the PhAc-ALGP-Cytotoxic Conjugate

When a satisfactory GP-prodrug is obtained, biological in vitro characteristics of the corresponding the PhAc-ALGP-cytotoxic compound conjugate are analyzed. This analysis includes assessing the in vitro cell cytotoxic effects of the original, unconjugated, parent drug and of its conjugated prodrug counterpart. Dose-response curves for drug and prodrug are compared. The prodrug is expected to exert comparable cytotoxicitcy as the unconjugated drug.

An alternative experiment consists of incubating the PhAc-ALGP prodrug with purified CD10 and TOP, and analyze conversion to GP-prodrug; after simultaneous incubation of the PhAc-ALGP prodrug with CD10, TOP, FAP and DPIV, the extent of conversion of PhAc-ALGP prodrug to free drug can be analyzed. Significantly high levels of conversion to GP-prodrug and free drug, respectively, are indicative of cytotoxic efficacy of the PhAc-ALGP prodrug in a cellular/tumor environment.

Both above described methodologies can also be combined: the cytotoxicity to in vitro cultured cells of the reaction product of PhAc-ALGP prodrug with purified CD10 and TOP, or of PhAc-ALGP prodrug with CD10, TOP, FAP and DPIV, or of both, can be compared to that of the free drug.

9.3. In Vitro Pharmacodynamics of GP-Cytotoxic Compound Conjugates and PhAc-ALGP-Cytotoxic Compound Conjugates The intracellular uptake (rate) of a prodrug before and after preincubation with proteases as described above is studied. In order to achieve this, adequate labeling of drug and prodrug may be required (see further).

10. In Vivo Testing Steps on the PhAc-ALGP-Cytotoxic Compound Conjugate 10.1. Determination of the Maximum Tolerated Dose (MTD)

In vivo testing first determines the MTD of the prodrug conjugate by measuring the weight loss of mice injected with increasing doses of the prodrug. This is compared with the MTD of the free cytotoxic drug. The MTD will be determined as the dose not inducing a weight loss exceeding 20% of the original weight of the animals.

Initially, the prodrug and the free drug will be administered IV 2 times with a weekly interval, possibly repeated one or more times. Based on the herein described experience with the doxorubicin prodrug, in vivo activation of the prodrug could be very (s)low. In such case, the MTD is determined in normal mice and in mice xenografted with a human tumor, after twice daily IP injections for 2 times 5 days. Alternatively slow infusion of the prodrugs is possible using osmotic or other programmable minipumps.

The effect of the prodrugs on the blood white cells count will be compared with the free drug.

10.2. Chemotherapeutic Activity on Immunodeficient Mice Grafted with Human Tumors One or two different human xenograft tumor models are selected on the basis of published data obtained with the unconjugated/free cytotoxic compound. Prodrug and free drug are injected IP at the MTD determined as described above. Body weight and tumor volume are measured every two days and compared with results obtained with the free starting drug at its MTD.

This can be repeated on other human tumor types such as human leukemias on orthotopic human xenografted tumors in SCID mice. Besides follow-up of the cytotoxic effect of the prodrug and drug on the primary tumor, the effect on metastases can be determined.

10.3. Pharmacokinetics, Tumor- and Tissue Distribution of PhAc-ALGP-Cytotoxic Compound Conjugates Except perhaps for a fluorescent drug such as amrubicin, pharmacokinetic tissue distribution studies of drug and prodrug may require adequate labeling of drug and prodrug too yield sufficient sensitivity in chemical analytical determination methods. One type of labeling is radiolabeling, the compounds could e.g. be radiolabeled by tritium exchange or by neosynthesis with $C_{-14}$ labeled precursors. Labeling should be such that the label, or a label is maintained in metabolites of the prodrug. Plasma pharmacokinetics are explored as well as tumor accumulation of the conjugated drug and its metabolites, combined with organ and tissue distribution.

Example 17. In Vivo Efficacy of PhAc-ALGP-Doxorubicin in UZLX-STS3 Soft Tissue Sarcoma Xenograft Model From the results of the experiment presented in FIGS. 16 to 19, several interesting properties of PhAc-ALGP-dox can be derived.

Tumor Volume.

In this experiment the effect of linking doxorubicin to the ALGP peptide has been assessed by testing its activity in doxorubicin resistant liposarcoma. The present results demonstrate that linking of doxorubicin to ALGP results in a higher tolerated experimental dose. As such, even in the experimental chemotherapy of a doxorubicin resistant sarcoma xenograft, PhAc-ALGP-dox is capable to limit xenograft growth of said doxorubicin resistant liposarcoma. In this study groups of mice (n=4 in both groups), with each mice bearing two tumors were respectively treated with saline (control group), treated with doxorubicin (doxorubicin-treated group) and treated with PhAc-ALGP-dox (PhAc-ALGP-dox-treated group) Between day 0 and day 21 of treatment in both control (n=7) and doxorubicin-treated tumors (n=8) there was a steady increase of tumor volume to 258% (p=0.018) and 246% (p=0.012), respectively. On the other hand tumors treated with PhAc-ALGP-dox revealed stabilization of tumor volume at 105% (FIG. 16). The delay in tumor volume growth in PhAc-ALGP-dox treated mice (n=6) was statistically significant on day 21 when compared with the control group (p=0.003) or with the doxorubicin-treated group (p=0.002).

The observed effect of PhAc-ALGP-dox may in part be explained by the 7-d continuous administration of the drug via a minipump.

A second and more fascinating explanation resides in a probably much higher release of doxorubicin in the tumor stroma than after administration of free doxorubicin (which can only be administered at a much lower dose). The cytostatic and cytotoxic effect of the released doxorubicin on stromal cells may in turn strongly affect the growth of the cancerous cells. This stromal effect may also explain the stabilizing effect on the tumor volume for 21 days without a reduction in their volume. Extended observation beyond 21 days, possibly in combination with repeated administration, using for example different vehicles with effect on active drug release, could synergistically result in a reduced tumor volume (after the destruction of all tumoral stromal cells).

Body Weight.

During the whole experiment, mice body weight and general well-being were monitored. A detailed graph depicting body weight evolution is presented in FIG. 17 (control group: n=4; PhAc-ALGP-dox-treated group: n=3; doxorubicin-treated group: n=4). No major side effects were observed and in general the animals' body weight did not drop below the acceptable value (20% of the starting body weight loss during the treatment). One mouse was sacrificed for ethical reasons on day 13 in the PhAc-ALGP-dox group (body weight 79.8%, animal getting skinny from day 11, limited intraperitoneal ascites fluid found during the necropsy probably due to infection as consequence of the surgical implantation of the minipump).

Total White Blood Cell Count and Total Neutrophil Count

No major changes in total white blood cells and neutrophils were observed in mice treated with PhAc-ALGP-dox in comparison with control or doxorubicin-treated animals (FIGS. 18 and 19, respectively; control group: n=4; PhAc-ALGP-dox-treated group: n=3; doxorubicin-treated group: n=4). Neutropenia is one of the most important toxic side effects of free doxorubicin-treatment. Therefore, unchanged netrophil count 21 days after administration of PhAc-ALGP-doxorubicin at 40-times higher dose than free doxorubicin is from a clinical point of view a very promising, novel experimental result.

---

The invention claimed is:

1. A prodrug having the general structure:

[$C_x$-OP]$_y$-D, wherein C is a phosphonoacetyl group;
OP is a tetrapeptide with the sequence ALGP (SEQ ID NO: 1), TSGP (SEQ ID NO: 4), or KLGP (SEQ ID NO: 6), and amino acids of the tetrapeptide are naturally occurring amino acids;
D is a therapeutic drug;
x is an integer of at least 1;
x is 1 when y=1;
y is an integer being at least 1, if y is greater than 1, then at least 1 OP is carrying a capping group; and
wherein the linkage between C and OP and the linkage between OP and D is direct, and wherein, if y is greater than 1, the multiple OP moieties are individually linked to each other directly and one of the multiple OP moieties is linked to D directly;
or a pharmaceutically acceptable salt thereof.

2. A prodrug having the general structure:

[$C_x$-OP]$_y$-D, wherein C is a succinyl group;
OP is a tetrapeptide with the sequence ALGP (SEQ ID NO: 1) or KLGP (SEQ ID NO: 6), and amino acids of the tetrapeptide are naturally occurring amino acids;
D is a therapeutic drug;
x is an integer of at least 1;
x is 1 when y=1;
y is an integer being at least 1, if y is greater than 1, then at least 1 OP is carrying a capping group; and
wherein the linkage between C and OP and the linkage between OP and D is direct, and wherein, if y is greater than 1, the multiple OP moieties are individually linked to each other directly and one of the multiple OP moieties is linked to D directly;
or a pharmaceutically acceptable salt thereof.

3. The prodrug or salt thereof according to claim 1 wherein said drug D is doxorubicin.

4. The prodrug or salt thereof according to claim 1 wherein said drug D is pegylated.

5. The prodrug or salt thereof according to claim 1 wherein said prodrug is Compound I:

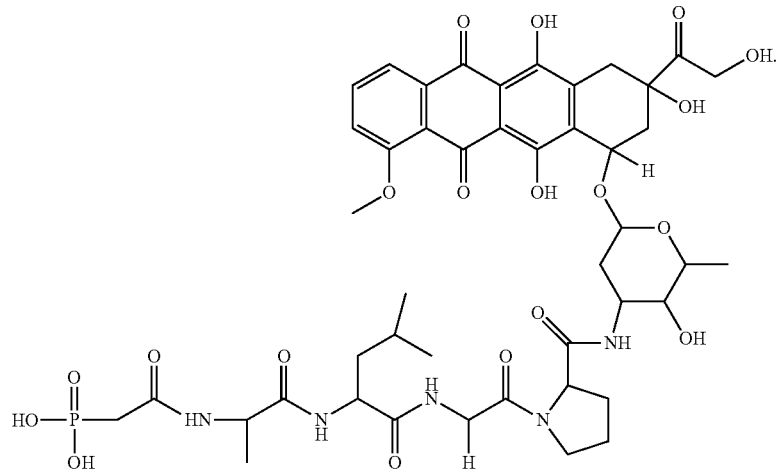 [SMILES: COc1cccc2c1C(=O)c1c(O)c3c(c(O)c1C2=O)CC(O)(C(=O)CO)CC3OC1CC(NC(=O)C2CCCN2C(=O)CNC(=O)C(CC(C)C)NC(=O)C(C)NC(=O)CP(=O)(O)O)C(O)C(C)O1]

6. A composition comprising the prodrug or salt thereof according to claim 1.

7. The composition according to claim 6 further comprising at least one of a pharmaceutically acceptable solvent, diluents or carrier.

8. A method for treating a tumor or cancer in a subject, said method comprising administering to a subject having cancer an amount of prodrug or salt thereof according to claim 1 sufficient to provide a therapeutically effective amount of drug in the vicinity of the tumor or cancer, said administering resulting in the treatment of said tumor or cancer.

9. The method according to claim 8 wherein the therapeutically effective amount of said prodrug or salt thereof, or of said composition is not causing leukopenia or cardiac toxicity.

10. The method according to claim 8 which is part of a combination chemotherapy treatment or a combined modality chemotherapy treatment.

11. The method according to claim 8 which is combined with a treatment including administering a drug resistance reverting agent to the subject.

12. A method for producing the prodrug according to claim 1, said method comprising the steps of:
(i) obtaining the drug;
(ii) linking the drug to a capped oligopeptidic moiety, resulting in the prodrug; or, alternatively,
(ii') linking the drug to an oligopeptidic moiety followed by linking the capping group to the oligopeptidic moiety, resulting in the prodrug; and
(iii) purifying the prodrug obtained in step (ii) or (ii');
wherein the oligopeptidic moiety is a tetrapeptide with the sequence ALGP (SEQ ID No 1), TSGP (SEQ ID NO: 4), or KLGP (SEQ ID NO: 6).

13. The method according to claim 12 wherein said capping group C is a phosphonoacetyl group.

14. The method according to claim 12 wherein said drug D is selected from the group consisting of maytansine, geldanamycin, paclitaxel, docetaxel, campthothecin, vinblastine, vincristine, methothrexate, aminopterin, amrubicin, or a derivative of any thereof.

15. The method according to claim 12 wherein, when present, said linker or spacing group is a self-eliminating linker or spacing group.

16. The prodrug or salt thereof according to claim 2 wherein said drug D is doxorubicin.

17. The prodrug or salt thereof according to claim 2 wherein said drug D is pegylated.

18. A composition comprising the prodrug or salt thereof according to claim 2.

19. A method for treating a tumor or cancer in a subject, said method comprising administering to a subject having cancer an amount of prodrug or salt thereof according to claim 2 sufficient to provide a therapeutically effective amount of drug in the vicinity of the tumor or cancer, said administering resulting in the treatment of said tumor or cancer.

20. A method for producing the prodrug according to claim 2, said method comprising the steps of:
(i) obtaining the drug;
(ii) linking the drug to a capped oligopeptidic moiety, resulting in the prodrug; or, alternatively,
(ii') linking the drug to an oligopeptidic moiety followed by linking the capping group to the oligopeptidic moiety, resulting in the prodrug; and
(iii) purifying the prodrug obtained in step (ii) or (ii');
wherein the oligopeptidic moiety is a tetrapeptide with the sequence ALGP (SEQ ID No 1) or KLGP (SEQ ID NO: 6).

* * * * *

SEQUENCE LISTING

```
<160> NUMBER OF SEQ ID NOS: 10

<210> SEQ ID NO 1
<211> LENGTH: 4
<212> TYPE: PRT
<213> ORGANISM: artificial sequence
<220> FEATURE:
<223> OTHER INFORMATION: synthetic oligopeptide

<400> SEQUENCE: 1

Ala Leu Gly Pro
1

<210> SEQ ID NO 2
<211> LENGTH: 4
<212> TYPE: PRT
<213> ORGANISM: artificial sequence
<220> FEATURE:
<223> OTHER INFORMATION: synthetic oligopeptide

<400> SEQUENCE: 2

Ala Leu Ala Leu
1

<210> SEQ ID NO 3
<211> LENGTH: 4
<212> TYPE: PRT
```

```
<213> ORGANISM: artificial sequence
<220> FEATURE:
<223> OTHER INFORMATION: synthetic oligopeptide

<400> SEQUENCE: 3

Ala Leu Ala Pro
1

<210> SEQ ID NO 4
<211> LENGTH: 4
<212> TYPE: PRT
<213> ORGANISM: artificial sequence
<220> FEATURE:
<223> OTHER INFORMATION: synthetic oligopeptide

<400> SEQUENCE: 4

Thr Ser Gly Pro
1

<210> SEQ ID NO 5
<211> LENGTH: 4
<212> TYPE: PRT
<213> ORGANISM: artificial sequence
<220> FEATURE:
<223> OTHER INFORMATION: synthetic oligopeptide

<400> SEQUENCE: 5

Thr Ser Ala Pro
1

<210> SEQ ID NO 6
<211> LENGTH: 4
<212> TYPE: PRT
<213> ORGANISM: artificial sequence
<220> FEATURE:
<223> OTHER INFORMATION: synthetic oligopeptide

<400> SEQUENCE: 6

Lys Leu Gly Pro
1

<210> SEQ ID NO 7
<211> LENGTH: 4
<212> TYPE: PRT
<213> ORGANISM: artificial sequence
<220> FEATURE:
<223> OTHER INFORMATION: synthetic oligopeptide

<400> SEQUENCE: 7

Lys Leu Ala Pro
1

<210> SEQ ID NO 8
<211> LENGTH: 4
<212> TYPE: PRT
<213> ORGANISM: artificial sequence
<220> FEATURE:
<223> OTHER INFORMATION: synthetic oligopeptide

<400> SEQUENCE: 8

Ala Leu Lys Pro
1

<210> SEQ ID NO 9
<211> LENGTH: 4
<212> TYPE: PRT
```

```
<213> ORGANISM: artificial sequence
<220> FEATURE:
<223> OTHER INFORMATION: synthetic oligopeptide

<400> SEQUENCE: 9

Thr Ser Lys Pro
1

<210> SEQ ID NO 10
<211> LENGTH: 4
<212> TYPE: PRT
<213> ORGANISM: artificial sequence
<220> FEATURE:
<223> OTHER INFORMATION: synthetic oligopeptide

<400> SEQUENCE: 10

Lys Leu Lys Pro
1
```